US008519107B2

(12) United States Patent
Almagro et al.

(10) Patent No.: US 8,519,107 B2
(45) Date of Patent: Aug. 27, 2013

(54) IL-17A ANTIBODIES

(75) Inventors: Juan Carlos Almagro, Brookline, MA (US); Daniela Della Ducata, Martinsried/Planegg (DE); Merle Elloso, Spring House, PA (US); Jinquan Luo, Spring House, PA (US); Thomas Malia, Spring House, PA (US); Michael Naso, Spring House, PA (US); Galina Obmolova, Spring House, PA (US); Robert Rauchenberger, Martinsried/Planegg (DE); Mark Rutz, Lena-Christ-Strasse (DE); Raymond Sweet, Spring House, PA (US); Susann Taudte, Spring House, PA (US); Bingyuan Wu, Spring House, PA (US); Sheng-Jiun Wu, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 12/915,445

(22) Filed: Oct. 29, 2010

(65) Prior Publication Data

US 2011/0236390 A1    Sep. 29, 2011

Related U.S. Application Data

(60) Provisional application No. 61/256,862, filed on Oct. 30, 2009, provisional application No. 61/310,919, filed on Mar. 5, 2010.

(51) Int. Cl.
*C07K 16/24* (2006.01)
*C12P 21/08* (2006.01)

(52) U.S. Cl.
USPC ............. 530/388.23; 530/388.1; 530/387.1; 530/351; 424/133.1; 424/141.1; 435/69.6

(58) Field of Classification Search
None
See application file for complete search history.

(56) References Cited

U.S. PATENT DOCUMENTS

| | | | |
|---|---|---|---|
| 5,223,409 A | 6/1993 | Ladner et al. | |
| 6,649,055 B1 | 11/2003 | Whitton et al. | |
| 7,776,540 B2 | 8/2010 | Kastelein et al. | |
| 7,943,744 B2 * | 5/2011 | Frendeus et al. | 530/388.15 |
| 2008/0095775 A1 | 4/2008 | Lewis et al. | |
| 2009/0105461 A1 | 4/2009 | Kunz et al. | |
| 2010/0021477 A1 * | 1/2010 | Tsui et al. | 424/164.1 |

FOREIGN PATENT DOCUMENTS

| | | |
|---|---|---|
| WO | WO2006/013107 A1 | 2/2006 |
| WO | WO2006/054059 A1 | 5/2006 |
| WO | WO2007/070750 A1 | 6/2007 |
| WO | WO2008/021156 A2 | 8/2007 |
| WO | WO2007/106769 A2 | 9/2007 |
| WO | WO2007/149032 A1 | 12/2007 |
| WO | WO2008/001063 A1 | 1/2008 |
| WO | WO2009/003096 A2 | 12/2008 |
| WO | WO2009/130459 A2 | 4/2009 |
| WO | WO 2009/068649 A3 | 6/2009 |
| WO | WO2010/034443 A1 | 4/2010 |

OTHER PUBLICATIONS

"Ulcerative colitis—Introduction", University of Maryland Medical Center, http:// www.umm.edu/patiented/articles/ (2011).
Adams, et al., "Recent developments in the PHENIX software for automated crystallographic structure determination," Journal of Synchrotron Rad., 11: 53-55 (2004).
Aggarwal, et al., "Interkeukin-23 Promotes a Distinct CD4T Cell Activation State Characterized by the Production of Interleukin-17," The Journal of Biological Chemistry, 278(3): 1910-1914 (2003).
Alcorn, et al., "$T_H17$ Cells in Asthma and COPD," Annual Review of Physiology, 72: 495-516 (2010).
Al-Lazikani, et al., "Standard Conformations for the Canonical Structures of Immunoglobulins," Journal of Molecular Biology, 273: 927-948 (1997).
Juan C. Almagro, et al., "Identification of differences in the specificity-determining residues of antibodies that recognize antigens of different size: implications for the rational design of antibody repertoires," Journal of Molecular Recognition, 17: 132-143 (2004).
Barbas, et al., "In vitro evolution of a neutralizing human antibody to human immunodeficiency virus type 1 to enhance affinity and broaden strain cross-reactivity," Proceedings of the National Academy of Science USA, 91: 3809-3813 (1994).
Chothia, et al., "Canonical Structure for the Hypervariable Regions of Immunoglobulins," Journal of Molecular Biology, 196: 901-917 (1987).
Curtis, et al., "The Immunopathogenesis of Chronic Obstructive Pulmonary Disease," Proceedings of the American Thoracic Society, 4: 512-521 (2007).
Ely, et al., "Structural basis of receptor sharing by interleukin 17 cytokines," Nature Immunology, 10(12): 1245-1252 (2009).
Emsley, et al., "Coot: model-building tools for molecular graphics," Acta Crystallography, D60: 2126-2132 (2004).
Freese, et al., "Chronic allograft nephropathy-biopsy findings and outcome," Nephrology Dialysis Transplantation, 16: 2401-2406 (2001).
Fujimoto, et al., "Clinical association of serum interleukin-17 levels in systemic sclerosis: Is systemic sclerosis a TH17 disease?" Journal of Dermatological Science, 50: 240-242 (2008).
Gao, et al., "Making artificial antibodies: A format for phage display of combinatorial heterodimeric arrays," Proceedings of the National Academy of Science USA, 96: 6025-6030 (1999).
Genovese, et al., "LY2439821, a Humanized Anti-Interleukin-17 Monoclonal Antibody, in the Treatment of Patients with Rheumatoid Arthritis," Arthritis & Rheumatism, 62(4): 929-939 (2010).

(Continued)

Primary Examiner — Dong Jiang
(74) Attorney, Agent, or Firm — Kirk Baumeister

(57) ABSTRACT

Interleukin-17A (IL-17A) antibody antagonists, polynucleotides encoding IL-17A antibody antagonists or fragments thereof, and methods of making and using the foregoing are disclosed.

16 Claims, 22 Drawing Sheets

(56) References Cited

OTHER PUBLICATIONS

Gerhardt, et al., "Structure of IL-17A in Complex with a Potent, Fully Human Neutralizing Antibody," Journal of Molecular Biology, 394: 905-921 (2009).
Gudjonsson, et al., "Immunopathogenic mechanisms in psoriasis," Clinical and Experimental Immunology, 135: 1-8 (2004).
Hessel, et al., "Bronchoconstriction and airway hyperresponsiveness after ovalbumin inhalation in sensitized mice," European Journal of Pharmacology, 293: 401-412 (1995).
Holtt, et al., "IL-23/IL-17 Immunity as a Hallmark of Crohn's Disease," Inflammatory Bowel Diseases, 14(9): 1175-1184 (2008).
Hueber, et al., "Effects of AIN457, a Fully Human Antibody to Interleukin-17A, on Psoriasis, Rheumatoid Arthritis, and Uveitis," Science Translational Medicine, 2, 52ra72: 1-9 (2010).
Hymowitz, et al., "IL-17s adopt a cystine knot fold: structure and activity of a novel cytokine, IL-17F, and implications for receptor binding," The EMBO Journal, 20(19): 5332-5341 (2001).
Ivanov, et al., "Interleukin-17 as a drug target in human disease," Trends in Pharmacological Sciences, 30(2): 95-103(2009).
Johansen, et al., "Characterization of the interleukin-17 isoforms and receptors in lesional psoriatic skin," British Journal of Dermatology, 160: 319-324 (2009).
Kawaguchi, et al., "IL-17 cytokine family," Journal of Allergy and Clinical Immunology, 114: 1265-1273 (2004).
Kolls, et al., "Interleukin-17 Family Members and Inflammation," Immunity, 21: 467-476 (2004).
Kuestner, et al., "Identification of the IL-17 Receptor Related Molecule IL-17RC as the Receptor for IL-17F," The Journal of Immunology, 179: 5462-5473 (2007).
Lefranc, et al., "IMGT unique numbering for immunoglobulin and T cell receptor variable domains and Ig superfamily V-like domains," Developmental & Comparative Immunology, 27: 55-77 (2003).
Anders Linden, "Rationale for targeting interleukin-17 in the lungs," Current Opinion in Investigational Drugs, 4(11): 1304-1312 (2003).
Youhua Liu, "Renal fibrosis: New insights into the pathogenesis and therapeutics," Kidney International, 69: 213-217 (2006).
Loong, et al., "Evidence for the early involvement of interleukin 17 in human and experimental renal allograft rejection," Journal of Pathology, 197: 322-332 (2002).
Eric Lubberts, "IL-17/TH17 targeting: On the road to prevent chronic destructive arthritis," Cytokine, 41: 84-91 (2008).
Mangan, et al., "Transforming growth factor-β induces development of the $T_H17$ lineage," Nature, 441: 231-234 (2006).
R.B. Mannon, "Therapeutic Targets in the Treatment of Allograft Fibrosis," American Journal of Transplantation, 6: 667-675 (2006).
Maclennan, et al., "Structure-Function Relationships in the $Ca^{2+}$-Binding and Translocation Domain of SERCA1: physiological correlates in Brody disease," Acta Physiologica Scandinavica, 163(643): 55-67 (1998).
McAllister, et al., Role of IL-17A, IL-17F, and the IL-17 Receptor in Regulating Growth-Related Oncogene-α and Granulocyte Colony-Stimulating Factor in Bronchial Epithelium: Implications for Airway Inflammation in Cystic Fibrosis, The Journal of Immunology, 175:404-412 (2005).
Moseley, et al., "Interleukin-17 family and IL-17 receptors," Cytokine & Growth Factor Reviews, 14: 155-174 (2003).
Murata, et al., "Clinical association of serum interleukin-17 levels in systemic sclerosis: Is systemic sclerosis of TH17 disease?" Journal of Dermatological Science, 50: 240-242 (2008).
Phillips, et al., "Diabetic nephropathy: The central role of renal proximal tubular cells in tubulointerstitial injury," Histology and Histopathology, 17: 247-252 (2002).
Aled Phillips, "The Role of Proximal Tubular Cells in Interstitial Fibrosis: Understanding TGFβ1," Chang Gung Medical Journal, 30: 2-6 (2007).
Racusen, et al., "The Banff 97 working classification of renal allograft pathology," Kidney International, 55: 713-723 (1999).
Read, et al., "Induction of Inflammatory Bowel Disease in Immunodeficient Mice by Depletion of Regulatory T. Cells," Current Protocols in Immunology, Chapter 15, 15.13 (2001).
Randy J. Read, "Pushing the boundaries of molecular replacement with maximum likelihood," Biological Crystallography, D57: 1373-1382 (2001).
Ritz, et al., "Nephropathy of type II diabetes," Nephrology DialysisTransplantation, 11(Suppl. 9): 38-44 (1996).
Shi, et al., "De Novo Selection of High-Affinity Antibodies from Synthetic Fab Libraries Displayed on Phage as pIX Fusion Proteins," Journal of Molecular Biology, 397: 385-396 (2010).
Simonson, et al., "Phenotypic transitions and fibrosis in diabetic nephropathy," Kidney International, 71: 846-854 (2007).
Strong, et al., "Three-Dimensional Structure of Murine Anti-p-azophenylarsonate Fab 36-71. X-ray Crystallography, Site-Directed Mutagenesis, and Modeling of the Complex with Hapten," Biochemistry, 30: 3739-3748 (1991).
Teplyakov, et al., "Epitope Mapping of Anti-Interleukin-13 Neutralizing Antibody CNTO607," Journal of Molecular Biology, 389: 115-123 (2009).
Toda, et al., "Polarized in vivo expression of IL-11 and IL-17 between acute and chronic skin lesions," Journal of Allergy and Clinical Immunology, 111: 875-881 (2003).
Tornetta, et al., "Antibody Fab display and selection through fusion to the pIX coat protein of filamentous phage," Journal of Immunological Methods, 360: 39-46 (2010).
Toy, et al., "Cutting Edge: Interleukin 17 Signals through a Heterodimeric Receptor Complex," The Journal of Immunology, 177: 36-39 (2006).
Van Kooten, et al., "Interleukin-17 Activates Human Renal Epithelial Cells in Vitro and Is Expressed during Renal Allograft Rejection," Journal of the American Society of Nephrology, 9: 1526-1534 (1998).
Woltman, et al., "Interkeukin-17 and CD40-Ligand Synergistically Enhance Cytokine and chemokine Production by Renal Epithelial Cells," Journal of the American Society of Nephrology, 11: 2044-2055 (2000).
Weaver, et al., "IL-17 Family Cytokines and the Expanding Diversity of Effector T Cell Lineages," Annual Review of Immunology, 25: 821-852 (2007).
Wright, et al., "Identification of an Interleukin 17F/17A Heterodimer in Activated Human CD4+TCells," The Journal of Biological Chemistry, 282(18): 13447-13455 (2007).
Zhang, et al., "Critical Role of IL-17 Receptor Signaling in Acute TNBS-induced Colitis," Inflammatory Bowel Diseases, 12(5): 382-388 (2006).
GenBank Accession No. NP_002181 (May 1, 2011).
GenBank Accession No. NP_055154 (May 14, 2011).
GenBank Accession No. NP_703191 (Apr. 10, 2011).

* cited by examiner

Figure 1A.

Family 2 HCDR2

| MOR# | mAb# | Family 2 HCDR2 consensus | | | | | | | | | | | | | | | | | SEQ ID NO |
|---|---|---|---|---|---|---|---|---|---|---|---|---|---|---|---|---|---|---|
| | | H | I | I | P | W | F | G | W | T | Y | Y | A | Q | K | F | Q | G | |
| 7702 | | | | | | | | | | | | | | | | | | | |
| 7701 | | M | | | | | | | T | | F | | | | | | | | |
| 7708 | 624 | R | | | | | | | | | S | | | | | | | | |
| 8297 | | R | | | | | | | T | | S | | | | | | | | |
| 8298 | | R | | | | | | | Y | | S | | | | | | | | |
| 7785 | 3077 | S | | | | | | | | | N | | | | | | | | |
| 8104 | 7024 | S | | | | | | | T | | N | | | | | | | | |
| 8105 | | S | | | | | | | Y | | N | | | | | | | | |
| 7786 | | Y | | | | | | | | | N | | | | | | | | |
| Consensus | | HMRSY | | | | | | | WTY | | YFSD | | | | | | | | |
| Formula I | | Xaa$_1$ | I | I | P | W | F | G | Xaa$_2$ | T | Xaa$_3$ | Y | A | Q | K | F | Q | G | 35 |

Xaa$_1$ may be His, Met, Arg, Ser or Tyr;
Xaa$_2$ may be Trp, Thr or Tyr; and
Xaa$_3$ may be Tyr, Phe, Ser or Asp.

Figure 1B.

Family 6a LCDR3

| MOR# | mAb# | Family 6a LCDR3 consensus | | | | | | | | SEQ ID NO |
|---|---|---|---|---|---|---|---|---|---|---|
| Clone 10 | | H | Q | F | T | I | P | S | H | |
| Clone 11 | | Q | | V | T | | | F | | |
| Clone 12 | | Q | | G | N | Y | R | P | L | |
| Consensus | | HQ | | FG | TVN | ITY | PR | SP | HFL | |
| Formula II | | Xaa4 | Q | Xaa5 | Xaa6 | Xaa7 | Xaa8 | Xaa9 | Xaa10 | 11 |

Xaa4 may be His or Gln;
Xaa5 may be Phe or Gly;
Xaa6 may be Thr, Val or Asn;
Xaa7 may be Ile, Thr or Tyr;
Xaa8 may be Pro or Arg;
Xaa9 may be Ser or Pro; and
Xaa10 may be His, Phe or Leu.

Figure 1C.

Family 6b LCDR3

| MOR# | mAb# | Family 6B LCDR3 consensus | | | | | | | | | | SEQ ID NO |
|---|---|---|---|---|---|---|---|---|---|---|---|---|
| | | Q | Q | S | N | H | I | P | P | A | T | |
| Clone 13 | | | | | | | | | | | | |
| | 7706 | | | Y | R | S | T | L | S | L | | |
| | 8299 | | | Y | R | S | T | L | S | L | | |
| | 8300 | | | Y | R | S | T | L | S | L | | |
| | 8301 | | | Y | R | S | T | L | S | L | | |
| Clone 15 | | | | Y | V | S | L | S | F | D | | |
| Clone 16 | | | | Y | Y | S | A | | L | L | | |
| | 7775 | T | | Y | Y | S | S | | S | L | | |
| | 732 | T | | Y | Y | S | S | | S | L | | |
| | 8101 | T | | Y | Y | S | S | | S | L | | |
| | 8102 | T | | Y | Y | S | S | | S | L | | |
| | 8103 | T | | Y | Y | S | S | | S | L | | |
| | 4168 | | | | | | | | | | | |
| Consensus | | QT | Q | SY | NRVY | HS | ITLAS | PLS | PSFL | ALD | T | |
| Formula III | | Xaa11 | Q | Xaa12 | Xaa13 | Xaa14 | Xaa15 | Xaa16 | Xaa17 | Xaa18 | T | 17 |

Xaa11 may be Gln or Thr;
Xaa12 may be Ser or Tyr;
Xaa13 may be Asn, Arg, Val or Tyr;
Xaa14 may be His or Ser;
Xaa15 may be Ile, Thr, Leu, Ala or Ser;
Xaa16 may be Pro, Leu or Ser;
Xaa17 may be Pro, Ser, Phe or Leu; and
Xaa18 may be Ala, Leu or Asp.

Figure 1D.

Family 6b HCDR3

| MOR# | mAb# | Family 6b HCDR3 consensus | | | | | | | | | | | | SEQ ID NO |
|---|---|---|---|---|---|---|---|---|---|---|---|---|---|---|
| | | E | V | D | S | M | Y | Y | S | Y | F | D | I | |
| Clone 13 | | | | | | | | | | | | | | |
| 7706 | 4538 | | | | | | | | | | | | | |
| 8299 | 3584 | | | | | | | | | | | | | |
| 8300 | | | | | | I | | | | | | | | |
| 8301 | | | | | | L | | | | | | | | |
| Clone 15 | | | | | | T | | | | | | | | |
| Clone 16 | | | | | | | | | | | | | | |
| 7775 | 732 | | | | | I | | | | | | | | |
| 8101 | | | | | | L | | | | | | | | |
| 8102 | | | | | | T | | | | | | | | |
| 8103 | 4168 | | | | | | | | | | | | | |
| Consensus | | E | V | D | S | MILT | Y | Y | S | Y | F | D | I | |
| Formula IV | | E | V | D | S | Xaa19 | Y | Y | S | Y | F | D | I | 57 |

Xaa19 is Met, Ile, Leu or Thr.

Figure 1E.

Family 19a LCDR3

| Clone | MOR # | mAb # | Family 19A consensus sequence LCDR3 | | | | | | | | | | SEQ ID NO |
|---|---|---|---|---|---|---|---|---|---|---|---|---|---|
| 179 | | | G | S | Y | D | F | F | L | G | M | I | V | |
| 180 | | | | | | | | | | | | | | |
| 181 | 7709 | | | | | | | | | | | | | |
| 182 | | | | | | | | | | | | | | |
| 183 | 7700 | 1926 | | | | | | | | | | | | |
| | | 8095 | | | | | | | | | | | | |
| | | 8096 | | | | | | | | | | | | |
| | | 8097 | | | | | | | | | | | | |
| | | 8098 | | | | | | | | | | | | |
| | | 8141 | | | | | | | | | L | | | |
| | | 8142 | | | | | | | | | T | | | |
| | | 8143 | | | | | | | | | Y | | | |
| | | 8160 | 7146 | | | | | | | | L | | | |
| | | 8161 | | | | | | | | | T | | | |
| | | 8162 | | | | | | | | | Y | | | |
| | | 8302 | 6785 | | | | | | | | | | | |
| | | 8303 | | | | | | | | | T | | | |
| | | | 5548 | | | | | | | | L | | | |
| 184 | 7768 | | | | | | | | | | | | | |
| 185 | Clone 185 | | | | | | | | | | | | | |
| Consensus | | | G | S | Y | D | F | F | L | G | MLTY | I | V | |
| Formula V | | | G | S | Y | D | F | F | L | G | Xaa20 | I | V | 22 |

Xaa20 is Met, Leu, Thr or Tyr.

Figure 1F.

Family 19a HCDR2

| MOR# | mAb# | Family 19a consensus sequence HCDR2 | | | | | | | | | | | | | | | | SEQ ID |
|---|---|---|---|---|---|---|---|---|---|---|---|---|---|---|---|---|---|---|
| Clone 179 | | A | I | N | G | L | G | T | H | K | Y | Y | A | D | S | V | K | G | |
| Clone 180 | | | | S | M | D | | G | W | T | | | | | | | | | |
| 7709 | | G | | | K | A | | Y | Y | T | | | | | | | | | |
| Clone 182 | | G | | S | | H | | G | Y | | F | | | | | | | | |
| 7700 | 1926 | T | | S | M | T | S | G | F | T | | | | | | | | | |
| 8095 | | T | | S | I | T | S | G | F | T | | | | | | | | | |
| 8096 | | T | | S | L | T | S | G | F | T | | | | | | | | | |
| 8097 | | T | | S | M | T | S | G | F | T | | | | | | | | | |
| 8098 | | T | | S | M | T | S | G | F | T | | | | | | | | | |
| 8141 | | T | | S | M | T | S | G | F | T | | | | | | | | | |
| 8142 | | T | | S | M | T | S | G | F | T | | | | | | | | | |
| 8143 | | T | | S | M | T | S | G | F | T | | | | | | | | | |
| 8160 | 7146 | T | | S | M | T | S | G | F | T | | | | | | | | | |
| 8161 | | T | | S | M | T | S | G | F | T | | | | | | | | | |
| 8162 | | T | | S | M | T | S | G | F | T | | | | | | | | | |
| 8302 | 6785 | T | | S | L | T | S | G | F | T | | | | | | | | | |
| 8303 | | T | | S | L | T | S | G | F | T | | | | | | | | | |
| | 5548 | T | | S | L | T | S | G | F | T | | | | | | | | | |
| 7768 | | V | | | K | G | | D | F | | | | | | | | | | |
| Clone 185 | | V | | S | H | S | | G | W | I | N | | | | | | | | |
| Consensus | | AGTV | I | NS | GMKILH | LDAHTGS | GS | TGYD | HWYF | KTI | YFN | Y | A | D | S | V | K | G | |
| Formula VI | | Xaa21 | I | Xaa22 | Xaa23 | Xaa24 | Xaa25 | Xaa26 | Xaa27 | Xaa28 | Xaa29 | Y | A | D | S | V | K | G | 46 |

Xaa21 may be Ala, Gly, Thr or Val;
Xaa22 may be Asn or Ser;
Xaa23 may be Gly, Met, Lys, Ile, Leu or His;
Xaa24 may be Leu, Asp, Ala, His, Thr, Gly or Ser;
Xaa25 may be Gly or Ser;
Xaa26 may be Thr, Gly, Tyr or Asp;
Xaa27 may be His, Trp, Tyr or Phe;
Xaa28 may be Lys, Thr or Ile; and
Xaa29 may be Tyr, Phe or Asn.

Figure 1G.

Family 19a HCDR3

| MOR # | mAb # | Family 19a consensus sequence HCDR3 | | | | | | SEQ ID NO |
|---|---|---|---|---|---|---|---|---|
| Clone 179 | | Q | L | M | L | D | V | |
| Clone 180 | | | | | | | | |
| 7709 | | | | | | | | |
| Clone 182 | | | | | | | | |
| 7700 | 1926 | | | | | | | |
| 8095 | | | | | | | | |
| 8096 | | | | | | | | |
| 8097 | | | | L | | | | |
| 8098 | | | | T | | | | |
| 8141 | | | | | | | | |
| 8142 | | | | | | | | |
| 8143 | | | | | | | | |
| 8160 | 7146 | | | T | | | | |
| 8161 | | | | T | | | | |
| 8162 | | | | T | | | | |
| 8302 | 6785 | | | T | | | | |
| 8303 | | | | T | | | | |
| | 5548 | | | T | | | | |
| 7768 | | | | | | | | |
| Clone 185 | | | | | | | | |
| Consensus | | Q | L | MLT | L | D | V | |
| Formula VII | | Q | L | Xaa30 | L | D | V | 61 |

Xaa30 may be Met, Leu or Thr.

Figure 1H.

Family 19b HCDR2

| MOR# | mAb# | Family 19b consensus sequence HCDR2 | | | | | | | | | | | | | | | SEQ ID NO |
|---|---|---|---|---|---|---|---|---|---|---|---|---|---|---|---|---|---|
| Clone 186 | | V | T | S | A | N | G | R | T | Y | Y | A | D | S | V | K | G | |
| Clone 187 | | | | | K | M | | H | | | | | | | | | | |
| Clone 188 | | | | | M | T | | N | | | | | | | | | | |
| Clone 189 | | | | | H | R | D | N | | | | | G | | | | | |
| Consensus | | V | T | S | AKMH | NMTR | GD | RHN | T | Y | Y | A | DG | S | V | K | G | |
| Formula VIII | | V | T | S | Xaa31 | Xaa32 | Xaa3 | Xaa34 | T | Y | Y | A | Xaa35 | S | V | K | G | 51 |

Xaa31 may be Ala, Lys, Met or His;
Xaa32 may be Asn, Met, Thr or Arg;
Xaa33 may be Gly or Asp;
Xaa34 may be Arg, His or Asn; and
Xaa35 may be Asp or Gly.

Figure 2A.

```
            1                        *              *        60
6785        QSVLTQPPSVSVAPGQTARISCSGDNLGDKYANWYQQKPGQAPVLVIYDDIDRPSGIPER

IGLV3-1     SYELTQPPSVSVSPGQTASITCSGDKLGDKYACWYQQKPGQSPVLVIYQDSKRPSGIPER
IGLV3-9     SYELTQPLSVSVALGQTARITCGGNNIGSKNVHWYQQKPGQAPVLVIYRDSNRPSGIPER
IGLV3-10    SYELTQPPSVSVSPGQTARITCSGDALPKKYAYWYQQKSGQAPVLVIYEDSKRPSGIPER
IGLV3-12    SYELTQPHSVSVATAQMARITCGGNNIGSKAVHWYQQKPGQDPVLVIYSDSNRPSGIPER
IGLV3-16    SYELTQPPSVSVSLGQMARITCSGEALPKKYAYWYQQKPGQFPVLVIYKDSERPSGIPER
IGLV3-19    SSELTQDPAVSVALGQTVRITCQGDSLRSYYASWYQQKPGQAPVLVIYGKNNRPSGIPDR
IGLV3-21    SYVLTQPPSVSVAPGKTARITCGGNNIGSKSVHWYQQKPGQAPVLVIYYDSDRPSGIPER
IGLV3-22    SYELTQLPSVSVSPGQTARITCSGDVLGENYADWYQQKPGQAPELVIYEDSERYPGIPER
IGLV3-25    SYELMQPPSVSVSPGQTARITCSGDALPKQYAYWYQQKPGQAPVLVIYKDSERPSGIPER
IGLV3-27    SYELTQPSSVSVSPGQTARITCSGDVLAKKYARWFQQKPGQAPVLVIYKDSERPSGIPER
IGLV3-32    SSGPTQVPAVSVALGQMARITCQGDSMEGSYEHWYQQKPGQAPVLVIYDSSDRPSRIPER

61               * **       108
6785        FSGSNSGNTATLTISGTQAEDEADYYCGSYDFFLGMIVFGGGTKLTVL

IGLV3-1     FSGSNSGNTATLTISGTQAMDEADYYCQAWDSSTA
IGLV3-9     FSGSNSGNTATLTISRAQAGDEADYYCQVWDSSTA
IGLV3-10    FSGSSSGTMATLTISGAQVEDEADYYCYSTDSSGNH
IGLV3-12    FSGSNPGNTTTLTISRIEAGDEADYYCQVWDSSSDH
IGLV3-16    FSGSSSGTIVTLTISGVQAEDEADYYCLSADSSGTY
IGLV3-19    FSGSSSGNTASLTITGAQAEDEADYYCNSRDSSGNH
IGLV3-21    FSGSNSGNTATLTISRVEAGDEADYYCQVWDSSSDH
IGLV3-22    FSGSTSGNTTTLTISRVLTEDEADYYCLSGDEDN
IGLV3-25    FSGSSSGTTVTLTISGVQAEDEADYYCQSADSSGTY
IGLV3-27    FSGSSSGTTVTLTISGAQVEDEADYYCYSAADNN
IGLV3-32    FSGSKSGNTTTLTITGAQAEDEADYYYQLIDNHA

IGLJ1                                    YVFGTGTKVTVL
IGLJ2                                    VVFGGGTKLTVL
IGLJ3                                    VVFGGGTKLTVL
IGLJ4                                    FVFGGGTQLIIL
IGLJ5                                    WVFGEGTELTVL
IGLJ6                                    NVFGSGTKVTVL
IGLJ7                                    AVFGGGTQLTVL
```

Figure 2B.

```
              1                                                         *  *    *  *        70
6785          QVQLLESGGGLVQPGGSLRLSCAASGFTFSSYAMSWVRQAPGKGLEWVSTISLTSGFTYYADSVKGRFTI

IGHV3-7       EVQLVESGGGLVQPGGSLRLSCAASGFTFSSYWMSWVRQAPGKGLEWVANIKQDGSEKYYVDSVKGRFTI
IGHV3-9       EVQLVESGGGLVQPGRSLRLSCAASGFTFDDYAMHWVRQAPGKGLEWVSGISWNSGSIGYADSVKGRFTI
IGHV3-11      QVQLVESGGGLVKPGGSLRLSCAASGFTFSDYYMSWIRQAPGKGLEWVSYISSSGSTIYYADSVKGRFTI
IGHV3-16      EVQLVESGGGLVQPGGSLRLSCAASGFTFSNSDMNWARKAPGKGLEWVSGVSWNGSRTHYVDSVKRRFII
IGHV3-19      TVQLVESGGGLVEPGGSLRLSCAASGFTFSNSDMNWVRQAPGKGLEWVSGVSWNGSRTHYADSVKGRFII
IGHV3-20      EVQLVESGGGVVRPGGSLRLSCAASGFTFDDYGMSWVRQAPGKGLEWVSGINWNGGSTGYADSVKGRFTI
IGHV3-21      EVQLVESGGGLVKPGGSLRLSCAASGFTFSSYSMNWVRQAPGKGLEWVSSISSSSSYIYYADSVKGRFTI
IGHV3-23      EVQLLESGGGLVQPGGSLRLSCAASGFTFSSYAMSWVRQAPGKGLEWVSAISGSGGSTYYADSVKGRFTI
IGHV3-30      QVQLVESGGGVVQPGRSLRLSCAASGFTFSSYAMHWVRQAPGKGLEWVAVISYDGSNKYYADSVKGRFTI
IGHV3-30-3    QVQLVESGGGVVQPGRSLRLSCAASGFTFSSYAMHWVRQAPGKGLEWVAVISYDGSNKYYADSVKGRFTI
IGHV3-33      QVQLVESGGGVVQPGRSLRLSCAASGFTFSSYGMHWVRQAPGKGLEWVAVIWYDGSNKYYADSVKGRFTI
IGHV3-35      EVQLVESGGGLVQPGGSLRLSCAASGFTFSNSDMNWVHQAPGKGLEWVSGVSWNGSRTHYADSVKGRFII
IGHV3-43      EVQLVESGGVVVQPGGSLRLSCAASGFTFDDYTMHWVRQAPGKGLEWVSLISWDGGSTYYADSVKGRFTI
IGHV3-48      EVQLVESGGGLVQPGGSLRLSCAASGFTFSSYSMNWVRQAPGKGLEWVSYISSSSSTIYYADSVKGRFTI
IGHV3-64      EVQLVESGGGLVQPGGSLRLSCAASGFTFSSYAMHWVRQAPGKGLEYVSAISSNGGSTYYANSVKGRFTI
IGHV3-74      EVQLVESGGGLVQPGGSLRLSCAASGFTFSSYWMHWVRQAPGKGLVWVSRINSDGSSTSYADSVKGRFTI

71                        ***            115
6785          SRDNSKNTLYLQMNSLRAEDTAVYYCARQLTLDVWGQGTLVTVSS
IGHV3-7       SRDNAKNSLYLQMNSLRAEDTAVYYCAR
IGHV3-9       SRDNAKNSLYLQMNSLRAEDTALYYCAKD
IGHV3-11      SRDNAKNSLYLQMNSLRAEDTAVYYCAR
IGHV3-16      SRDNSRNSLYLQKNRRRAEDMAVYYCVR
IGHV3-19      SRDNSRNFLYQQMNSLRPEDMAVYYCVR
IGHV3-20      SRDNAKNSLYLQMNSLRAEDTALYHCAR
IGHV3-21      SRDNAKNSLYLQMNSLRAEDTAVYYCAR
IGHV3-23      SRDNSKNTLYLQMNSLRAEDTAVYYCAK
IGHV3-30      SRDNSKNTLYLQMNSLRAEDTAVYYCAR
IGHV3-30-3    SRDNSKNTLYLQMNSLRAEDTAVYYCAR
IGHV3-33      SRDNSKNTLYLQMNSLRAEDTAVYYCAR
IGHV3-35      SRDNSRNTLYLQTNSLRAEDTAVYYCVR
IGHV3-35      SRDNSRNTLYLQTNSLRAEDTAVYYCVR
IGHV3-43      SRDNSKNSLYLQMNSLRTEDTALYYCAKD
IGHV3-48      SRDNAKNSLYLQMNSLRAEDTAVYYCAR
IGHV3-64      SRDNSKNTLYLQMGSLRAEDMAVYYCAR
IGHV3-74      SRDNAKNTLYLQMNSLRAEDTAVYYCAR

IGHJ1                                   ...AEYFQHWGQGTLVTVSS
IGHJ2                                   ...YWYFDLWGRGTLVTVSS
IGHJ3                                   .....AFDVWGQGTMVTVSS
IGHJ4                                   .....YFDYWGQGTLVTVSS
IGHJ5                                   ....NWFDSWGQGTLVTVSS
IGHJ6                                   YYYYYGMDVWGQGTTVTVSS
```

Figure 3A-1

| MORmAb 8141 | MORmAb 8142 | MORmAb 8143 | mAb 6785 | Numbering | | | Kabat | Chothia |
|---|---|---|---|---|---|---|---|---|
| VL | VL | VL | VL | Sequential | Kabat | Chothia | CDR | HV |
| Q | Q | Q | Q | 1 | 1 | 1 | | |
| S | S | S | S | 2 | 2 | 2 | | |
| V | V | V | V | 3 | 3 | 3 | | |
| L | L | L | L | 4 | 4 | 4 | | |
| T | T | T | T | 5 | 5 | 5 | | |
| Q | Q | Q | Q | 6 | 6 | 6 | | |
| P | P | P | P | 7 | 7 | 7 | | |
| P | P | P | P | 8 | 8 | 8 | | |
| S | S | S | S | 9 | 9 | 9 | | |
| V | V | V | V | 10 | 11 | 11 | | |
| S | S | S | S | 11 | 12 | 12 | | |
| V | V | V | V | 12 | 13 | 13 | | |
| A | A | A | A | 13 | 14 | 14 | | |
| P | P | P | P | 14 | 15 | 15 | | |
| G | G | G | G | 15 | 16 | 16 | | |
| Q | Q | Q | Q | 16 | 17 | 17 | | |
| T | T | T | T | 17 | 18 | 18 | | |
| A | A | A | A | 18 | 19 | 19 | | |
| R | R | R | R | 19 | 20 | 20 | | |
| I | I | I | I | 20 | 21 | 21 | | |
| S | S | S | S | 21 | 22 | 22 | | |
| C | C | C | C | 22 | 23 | 23 | | |
| S | S | S | S | 23 | 24 | 24 | ▓ | |
| G | G | G | G | 24 | 25 | 25 | ▓ | ▓ |
| D | D | D | D | 25 | 26 | 26 | ▓ | ▓ |
| N | N | N | N | 26 | 27 | 27 | ▓ | ▓ |
| L | L | L | L | 27 | 28 | 28 | ▓ | ▓ |
| G | G | G | G | 28 | 29 | 29 | ▓ | ▓ |
| D | D | D | D | 29 | 30 | 30 | ▓ | ▓ |
| K | K | K | K | 30 | 31 | 31 | ▓ | ▓ |
| Y | Y | Y | Y | 31 | 32 | 32 | ▓ | ▓ |
| A | A | A | A | 32 | 33 | 33 | ▓ | |
| N | N | N | N | 33 | 34 | 34 | ▓ | |
| W | W | W | W | 34 | 35 | 35 | | |
| Y | Y | Y | Y | 35 | 36 | 36 | | |
| Q | Q | Q | Q | 36 | 37 | 37 | | |
| Q | Q | Q | Q | 37 | 38 | 38 | | |
| K | K | K | K | 38 | 39 | 39 | | |
| P | P | P | P | 39 | 40 | 40 | | |
| G | G | G | G | 40 | 41 | 41 | | |
| Q | Q | Q | Q | 41 | 42 | 42 | | |
| A | A | A | A | 42 | 43 | 43 | | |
| P | P | P | P | 43 | 44 | 44 | | |
| V | V | V | V | 44 | 45 | 45 | | |
| L | L | L | L | 45 | 46 | 46 | | |
| V | V | V | V | 46 | 47 | 47 | | |
| I | I | I | I | 47 | 48 | 48 | | |
| Y | Y | Y | Y | 48 | 49 | 49 | | |
| D | D | D | D | 49 | 50 | 50 | ▓ | ▓ |
| D | D | D | D | 50 | 51 | 51 | ▓ | |
| I | I | I | I | 51 | 52 | 52 | ▓ | |
| D | D | D | D | 52 | 53 | 53 | ▓ | |
| R | R | R | R | 53 | 54 | 54 | ▓ | |
| P | P | P | P | 54 | 55 | 55 | ▓ | |
| S | S | S | S | 55 | 56 | 56 | ▓ | |
| G | G | G | G | 56 | 57 | 57 | | |

Figure 3A-2

| | | | | | | | | |
|---|---|---|---|---|---|---|---|---|
| I | I | I | I | 57 | 58 | 58 | | |
| P | P | P | P | 58 | 59 | 59 | | |
| E | E | E | E | 59 | 60 | 60 | | |
| R | R | R | R | 60 | 61 | 61 | | |
| F | F | F | F | 61 | 62 | 62 | | |
| S | S | S | S | 62 | 63 | 63 | | |
| G | G | G | G | 63 | 64 | 64 | | |
| S | S | S | S | 64 | 65 | 65 | | |
| N | N | N | N | 65 | 66 | 66 | | |
| S | S | S | S | 66 | 67 | 67 | | |
| G | G | G | G | 67 | 68 | 68 | | |
| N | N | N | N | 68 | 69 | 69 | | |
| T | T | T | T | 69 | 70 | 70 | | |
| A | A | A | A | 70 | 71 | 71 | | |
| T | T | T | T | 71 | 72 | 72 | | |
| L | L | L | L | 72 | 73 | 73 | | |
| T | T | T | T | 73 | 74 | 74 | | |
| I | I | I | I | 74 | 75 | 75 | | |
| S | S | S | S | 75 | 76 | 76 | | |
| G | G | G | G | 76 | 77 | 77 | | |
| T | T | T | T | 77 | 78 | 78 | | |
| Q | Q | Q | Q | 78 | 79 | 79 | | |
| A | A | A | A | 79 | 80 | 80 | | |
| E | E | E | E | 80 | 81 | 81 | | |
| D | D | D | D | 81 | 82 | 82 | | |
| E | E | E | E | 82 | 83 | 83 | | |
| A | A | A | A | 83 | 84 | 84 | | |
| D | D | D | D | 84 | 85 | 85 | | |
| Y | Y | Y | Y | 85 | 86 | 86 | | |
| Y | Y | Y | Y | 86 | 87 | 87 | | |
| C | C | C | C | 87 | 88 | 88 | | |
| G | G | G | G | 88 | 89 | 89 | ▓ | |
| S | S | S | S | 89 | 90 | 90 | ▓ | |
| Y | Y | Y | Y | 90 | 91 | 91 | ▓ | ▓ |
| D | D | D | D | 91 | 92 | 92 | ▓ | ▓ |
| F | F | F | F | 92 | 93 | 93 | ▓ | ▓ |
| F | F | F | F | 93 | 94 | 94 | ▓ | ▓ |
| L | L | L | L | 94 | 95 | 95 | ▓ | ▓ |
| G | G | G | G | 95 | a | a | ▓ | ▓ |
| L | T | Y | M | 96 | b | b | ▓ | ▓ |
| I | I | I | I | 97 | 96 | 96 | ▓ | ▓ |
| V | V | V | V | 98 | 97 | 97 | | ▓ |
| F | F | F | F | 99 | 98 | 98 | | |
| G | G | G | G | 100 | 99 | 99 | | |
| G | G | G | G | 101 | 100 | 100 | | |
| G | G | G | G | 102 | 101 | 101 | | |
| T | T | T | T | 103 | 102 | 102 | | |
| K | K | K | K | 104 | 103 | 103 | | |
| L | L | L | L | 105 | 104 | 104 | | |
| T | T | T | T | 106 | 105 | 105 | | |
| V | V | V | V | 107 | 106 | 106 | | |
| L | L | L | L | 108 | a | a | | |

Figure 3B-1

| MORmAb 7709 VH | MORmAB 7700 VH | MORmAb 8096 VH | mAb 6785 VH | Numbering | | | Kabat CDR | Chothia HV |
|---|---|---|---|---|---|---|---|---|
| | | | | Sequential | Kabat | Chothia | | |
| Q | Q | Q | Q | 1 | 1 | 1 | | |
| V | V | V | V | 2 | 2 | 2 | | |
| Q | Q | Q | Q | 3 | 3 | 3 | | |
| L | L | L | L | 4 | 4 | 4 | | |
| L | L | L | L | 5 | 5 | 5 | | |
| E | E | E | E | 6 | 6 | 6 | | |
| S | S | S | S | 7 | 7 | 7 | | |
| G | G | G | G | 8 | 8 | 8 | | |
| G | G | G | G | 9 | 9 | 9 | | |
| G | G | G | G | 10 | 10 | 10 | | |
| L | L | L | L | 11 | 11 | 11 | | |
| V | V | V | V | 12 | 12 | 12 | | |
| Q | Q | Q | Q | 13 | 13 | 13 | | |
| P | P | P | P | 14 | 14 | 14 | | |
| G | G | G | G | 15 | 15 | 15 | | |
| G | G | G | G | 16 | 16 | 16 | | |
| S | S | S | S | 17 | 17 | 17 | | |
| L | L | L | L | 18 | 18 | 18 | | |
| R | R | R | R | 19 | 19 | 19 | | |
| L | L | L | L | 20 | 20 | 20 | | |
| S | S | S | S | 21 | 21 | 21 | | |
| C | C | C | C | 22 | 22 | 22 | | |
| A | A | A | A | 23 | 23 | 23 | | |
| A | A | A | A | 24 | 24 | 24 | | |
| S | S | S | S | 25 | 25 | 25 | | |
| G | G | G | G | 26 | 26 | 26 | | ▓ |
| F | F | F | F | 27 | 27 | 27 | | ▓ |
| T | T | T | T | 28 | 28 | 28 | | ▓ |
| F | F | F | F | 29 | 29 | 29 | | ▓ |
| S | S | S | S | 30 | 30 | 30 | | ▓ |
| S | S | S | S | 31 | 31 | 31 | ▓ | ▓ |
| Y | Y | Y | Y | 32 | 32 | 32 | ▓ | |
| A | A | A | A | 33 | 33 | 33 | ▓ | |
| M | M | M | M | 34 | 34 | 34 | ▓ | |
| S | S | S | S | 35 | 35 | 35 | ▓ | |
| W | W | W | W | 36 | 36 | a | | |
| V | V | V | V | 37 | 37 | 36 | | |
| R | R | R | R | 38 | 38 | 37 | | |
| Q | Q | Q | Q | 39 | 39 | 38 | | |
| A | A | A | A | 40 | 40 | 39 | | |
| P | P | P | P | 41 | 41 | 40 | | |
| G | G | G | G | 42 | 42 | 41 | | |
| K | K | K | K | 43 | 43 | 42 | | |
| G | G | G | G | 44 | 44 | 43 | | |
| L | L | L | L | 45 | 45 | 44 | | |
| E | E | E | E | 46 | 46 | 45 | | |
| W | W | W | W | 47 | 47 | 46 | | |
| V | V | V | V | 48 | 48 | 47 | | |
| S | S | S | S | 49 | 49 | 48 | | |
| G | T | T | T | 50 | 50 | 49 | | ▓ |
| I | I | I | I | 51 | 51 | 50 | | ▓ |
| N | S | S | S | 52 | 52 | 51 | ▓ | ▓ |
| K | M | L | L | 53 | a | 52 | ▓ | ▓ |
| A | T | T | T | 54 | 53 | 53 | ▓ | ▓ |
| G | S | S | S | 55 | 54 | 54 | ▓ | ▓ |
| Y | G | G | G | 56 | 55 | 55 | ▓ | ▓ |
| Y | F | F | F | 57 | 56 | 56 | ▓ | ▓ |
| T | T | T | T | 58 | 57 | 57 | ▓ | ▓ |

Figure 3B-2

| | | | | | | | | |
|---|---|---|---|---|---|---|---|---|
| Y | Y | Y | Y | 59 | 58 | 58 | | |
| Y | Y | Y | Y | 60 | 59 | 59 | | |
| A | A | A | A | 61 | 60 | 60 | | |
| D | D | D | D | 62 | 61 | 61 | | |
| S | S | S | S | 63 | 62 | 62 | | |
| V | V | V | V | 64 | 63 | 63 | | |
| K | K | K | K | 65 | 64 | 64 | | |
| G | G | G | G | 66 | 65 | 65 | | |
| R | R | R | R | 67 | 66 | 66 | | |
| F | F | F | F | 68 | 67 | 67 | | |
| T | T | T | T | 69 | 68 | 68 | | |
| I | I | I | I | 70 | 69 | 69 | | |
| S | S | S | S | 71 | 70 | 70 | | |
| R | R | R | R | 72 | 71 | 71 | | |
| D | D | D | D | 73 | 72 | 72 | | |
| N | N | N | N | 74 | 73 | 73 | | |
| S | S | S | S | 75 | 74 | 74 | | |
| K | K | K | K | 76 | 75 | 75 | | |
| N | N | N | N | 77 | 76 | 76 | | |
| T | T | T | T | 78 | 77 | 77 | | |
| L | L | L | L | 79 | 78 | 78 | | |
| Y | Y | Y | Y | 80 | 79 | 79 | | |
| L | L | L | L | 81 | 80 | 80 | | |
| Q | Q | Q | Q | 82 | 81 | 81 | | |
| M | M | M | M | 83 | 82 | 82 | | |
| N | N | N | N | 84 | a | a | | |
| S | S | S | S | 85 | b | b | | |
| L | L | L | L | 86 | c | c | | |
| R | R | R | R | 87 | 83 | 83 | | |
| A | A | A | A | 88 | 84 | 84 | | |
| E | E | E | E | 89 | 85 | 85 | | |
| D | D | D | D | 90 | 86 | 86 | | |
| T | T | T | T | 91 | 87 | 87 | | |
| A | A | A | A | 92 | 88 | 88 | | |
| V | V | V | V | 93 | 89 | 89 | | |
| Y | Y | Y | Y | 94 | 90 | 90 | | |
| Y | Y | Y | Y | 95 | 91 | 91 | | |
| C | C | C | C | 96 | 92 | 92 | | |
| A | A | A | A | 97 | 93 | 93 | | |
| R | R | R | R | 98 | 94 | 94 | | |
| Q | Q | Q | Q | 99 | 95 | 95 | | |
| L | L | L | L | 100 | 96 | 96 | | |
| M | M | M | T | 101 | 97 | 97 | | |
| L | L | L | L | 102 | 98 | 98 | | |
| D | D | D | D | 103 | 101 | 101 | | |
| V | V | V | V | 104 | 102 | 102 | | |
| W | W | W | W | 105 | 103 | 103 | | |
| G | G | G | G | 106 | 104 | 104 | | |
| Q | Q | Q | Q | 107 | 105 | 105 | | |
| G | G | G | G | 108 | 106 | 106 | | |
| T | T | T | T | 109 | 107 | 107 | | |
| L | L | L | L | 110 | 108 | 108 | | |
| V | V | V | V | 111 | 109 | 109 | | |
| T | T | T | T | 112 | 110 | 110 | | |
| V | V | V | V | 113 | 111 | 111 | | |
| S | S | S | S | 114 | 112 | 112 | | |
| S | S | S | S | 115 | 113 | 113 | | |

Figure 6A.
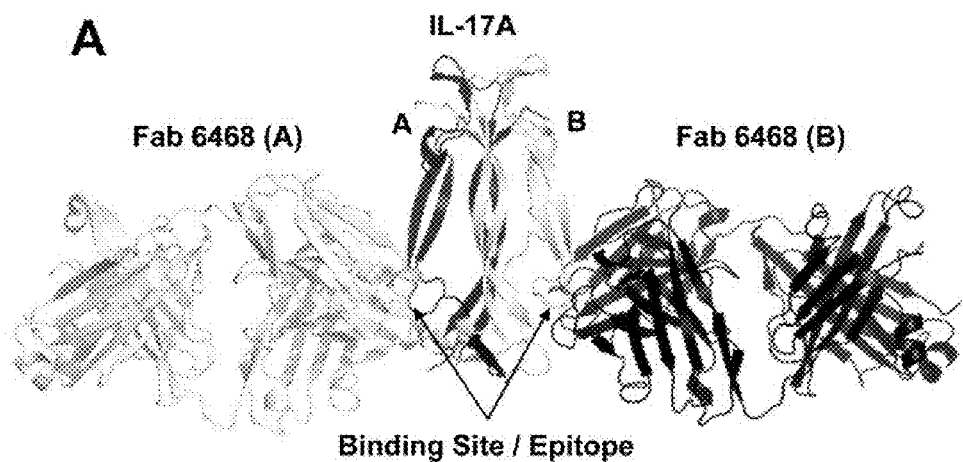
| Figure 6B. | Figure 6C. | Figure 6D. |
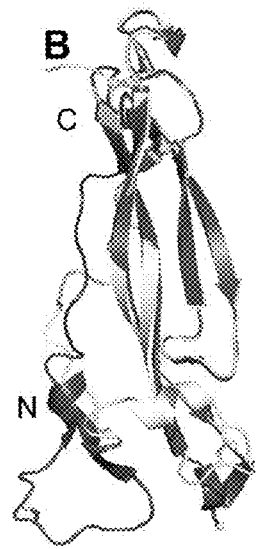  

Figure 8A.

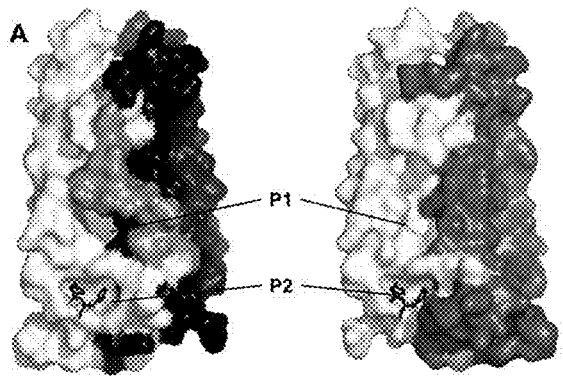

Figure 8B.

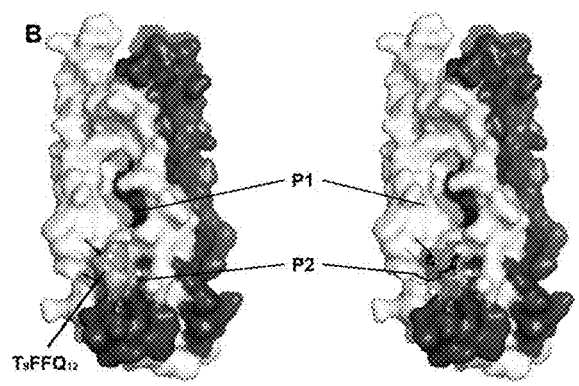

◊♦ Pocket P1 residues
△▲ Pocket P2 residues
Full and filled symbols indicate residues from the two monomers of the IL-17A dimer

```
IL-17A  (1)  --IVRAGITIPRNP-GCPNSEDKNFPRTVMVNLNIHNRNTNTNPKRSSDY
IL-17F  (1)  RKIPKVGHTFFQKPESCPPVPGG------SMKLDIGIINENQRVSMSRNI
                                            ▲ ▲

♦  ♦♦ ♦♦♦
IL-17A (48)  YNRSTSPWNLHRNEDPERYPSVIWEAQCRHLGCINADGNVDYHMNSVPIQ
IL-17F (45)  ESRSTSPWNYTVTWDPNRYPSEVVQAQCRNLGCINAQGKEDISMNSVPIQ
                                       ▲

◊◊♦◊                          ♦ ♦
IL-17A (98)  QEILVLRREPPHCPNSFRLEKILVSVGCTCVTPIVHHVQ
IL-17F (95)  QETLVVRRKHQGCSVSFQLEKVLVTVGCTCVTPVIHHVQ
                △ ▲▲         ▲ △
```

IL-17A ANTIBODIES

This application claims the benefit of U.S. Provisional Application No. 61/256,862, filed 30 Oct. 2009 and U.S. Provisional Application No. 61/310,919, filed 5 Mar. 2010, the entire contents of which are incorporated herein by reference.

FIELD OF THE INVENTION

The present invention relates to interleukin-17A (IL-17A) antibody antagonists, polynucleotides encoding IL-17A antibody antagonists or fragments thereof, and methods of making and using the foregoing.

BACKGROUND OF THE INVENTION

Interleukin-17A (IL-17A, CTLA-8, IL-17) is a cytokine secreted by activated Th17 cells, CD8⁺ T cells, γδ T cells and NK cells in response to cytokines such as IL-23 and TGF-β, and regulates production of mediators such as antimicrobial peptides (defensins), proinflamatory cytokines and chemokines from multiple cell types such as fibroblasts and synoviocytes that are involved in neutrophil biology, inflammation, organ destruction and host defense (reviewed in Weaver et al., Annu. Rev. Immunol. 25:821-52, 2007; Aggarwal et al., J. Biol. Chem. 278:1910-4, 2003; Mangan et al., Nature 441: 231-4, 2006). IL-17A synergizes with other cytokines, such as TNF-α and IL-1β to potentiate the pro-inflammatory environment.

The IL-17A cytokine family consists of six homologs designated IL-17A, B, C, D, E and F, each with divergent and distinct biological roles (Kawaguchi et al., J. Allergy Clin. Immunol. 114:1265-73, 2004; Kolls and Linden, Immunity 21:467-76, 2004; Moseley et al., Cytokine Growth Factor Rev. 14:155-74, 2003). Of the family members, IL-17F is most homologous to IL-17A and shares many similar functional properties such as induction of neutrophilia in the lung and induction of pro-inflammatory cytokines; however, in man, IL-17F is about 10-fold less potent than IL-17A (Moseley et al., Cytokine Growth Factor Rev. 14:155-74, 2003; Kolls et al., Immunity, 21: 467-76, 2004; McAllister et al., J. Immunol. 175:404-12, 2005). IL-17A and IL-17F can also form heterodimers, which have intermediate bioactivity in vitro (Wright et al., J. Biol. Chem. 282:13447-55, 2007).

IL-17A mediates it effects by interacting with the Interleukin-17 receptor A (IL-17RA) and receptor C (IL-17RC) (Moseley et al., Cytokine Growth Factor Rev. 14:155-74, 2003; Toy et al., J. Immunol. 177:36-9, 2006). IL-17F signals through the same receptors, although IL-17F affinity to the receptors is significantly lower (Kuestner et al., J. Immunol. 179:5462-73, 2007). Crystal structures of human IL-17F and human IL-17F/IL-17RA complex identified a putative receptor-binding cavity in the IL-17F homodimer (Hymowitz et al., EMBO J. 20:5332-41, 2001; Ely et al., Nat. Immunology 10:1245-51, 2009). A similar cavity was identified in the crystal structure of human IL-17A in complex with a neutralizing Fab, although the cavity was partially occupied (Gerhardt et al., J. Mol. Biol. 394:905-21, 2009).

Inappropriate or excessive production of IL-17A is associated with the pathology of various diseases and disorders, including rheumatoid arthritis (Lubberts, Cytokine 41:84-91, 2008), airway hypersensitivity including allergic airway disease such as asthma (reviewed in Linden, Curr. Opin. Investig. Drugs. 4:1304-12, 2003; Ivanov, Trends Pharmacol. Sci. 30:95-103, 2009), psoriasis (Johansen et al., Br. J. Dermatol. 160:319-24, 2009), dermal hypersensitivity including atopic dermatitis (Toda et al., J. Allergy Clin. Immunol. 111:875-81, 2003), systemic sclerosis (Fujimoto et al., J. Dermatolog. Sci. 50:240-42, 2008), inflammatory bowel diseases including ulcerative colitis and Crohn's disease (Holtta et al., Inflamm. Bowel Dis. 14:1175-84, 2008; Zhang et al., Inflamm. Bowel Dis. 12:382-88, 2006), and pulmonary diseases including chronic obstructive pulmonary disease (Curtis et al., Proc. Am. Thorac. Soc. 4:512-21, 2007).

Antibodies to IL-17A have been proposed for use in the treatment of IL-17A mediated diseases and disorders (PCT Publ. Nos: WO08/021156, WO07/070750, WO07/149032, WO06/054059, WO06/013107, WO08/001063, WO10/034443; US Pat. Appl. Nos. US2008/095775, US2009/0175881;). As the pharmacokinetic, efficacy and safety profiles of antibody therapeutics will be dependent on specific compositions, there is a need for improved antibodies to human IL-17A that are suitable for use in the treatment of IL-17A mediated diseases and disorders.

BRIEF DESCRIPTION OF THE DRAWINGS

FIG. 1. A-H. CDR sequences of Family 2, 6a, 6b, 19a, and 19b IL-17A antibody antagonists.

FIG. 2. Exemplary A) IGLV3 and IGLJ; and B) IGHV3 and IGHJ germline genes as scaffolds for grafting paratope residues. mAb6785 sequence is shown above. CDR regions are underlined and core contact sites in mAb6785 light chain (Y31, D49, Y90, F92, F93) and heavy chain (S52, T54, F57, Y59, Q99, L100 and T101) are denoted by an asterix "*". Framework 4 regions in B) are double underlined. Sequence shown are *01 alleles unless specifically indicated otherwise.

FIG. 3. Kabat and Chotia numbering for select antibody A) light and B) heavy chains. Locations of Kabat CDRs and Chothia HVs are highlighted in gray.

FIG. 6. A) The overall molecular structure of IL-17A/Fab6468 complex. The dimer of IL-17A is shown dark gray and light gray. The two Fab molecules are shown in dark gray and light gray, repectively; B) Comparison of monomer of IL-17A (light gray) and IL-17F (dark gray); C) Dimer of IL-17A (light and dark gray); D) Dimer of IL-17F (light and dark gray).

FIG. 8. Comparison of IL-17A and IL-17F putative receptor binding pockets. A) Front and Back views of the the P1 and P2 pockets of IL-17A. The FF motif of mAb6468 light chain CDR3 is shown in the P2 pocket. B) IL-17F with N-terminal FF motif in the P2 pocket. C) Sequence alignment of IL-17A and IL-17F and the conservation of P1 and P2 pockets.

SUMMARY OF THE INVENTION

Figure 4A:
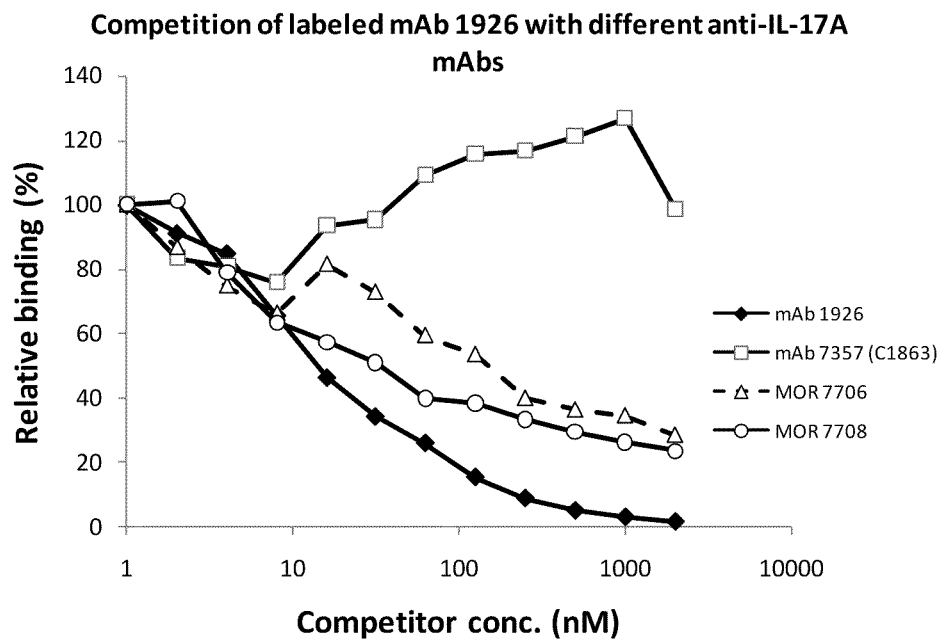
FIG. 4. Competitive binding assays of labeled A) and B) mAb1926; C) mAb317; D) mAb3171; E) and F) mAb7357 with IL-17A in an ELISA format.
Figure 4B:
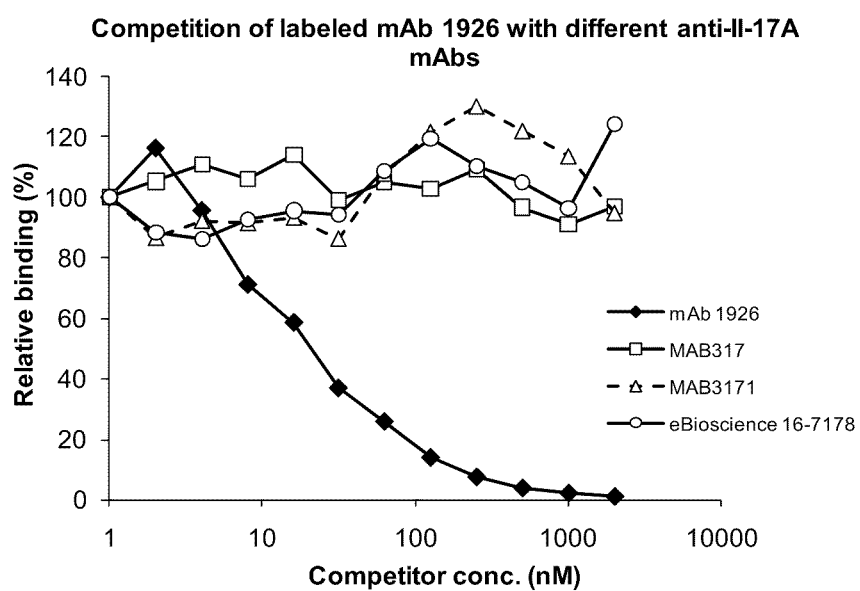
Figure 4C:
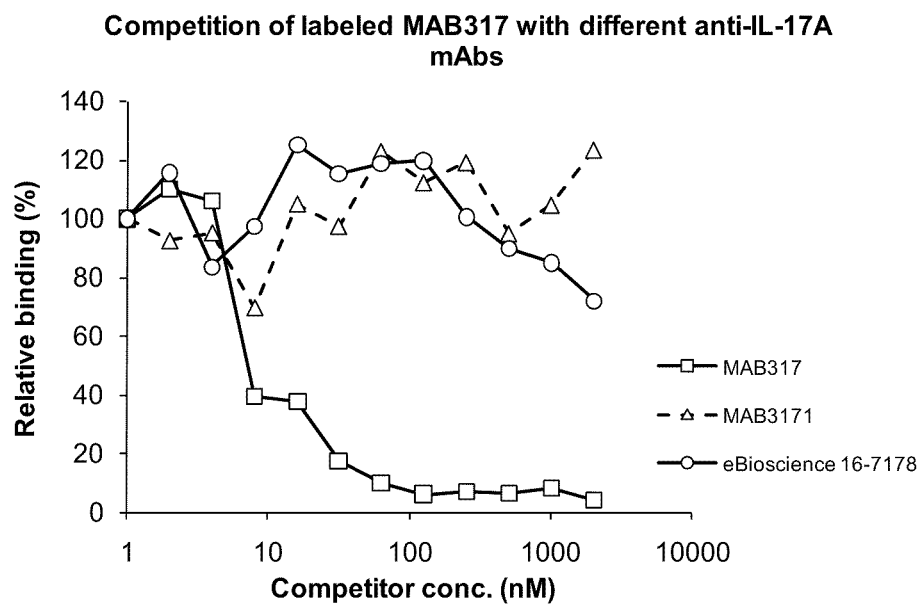
Figure 4D:
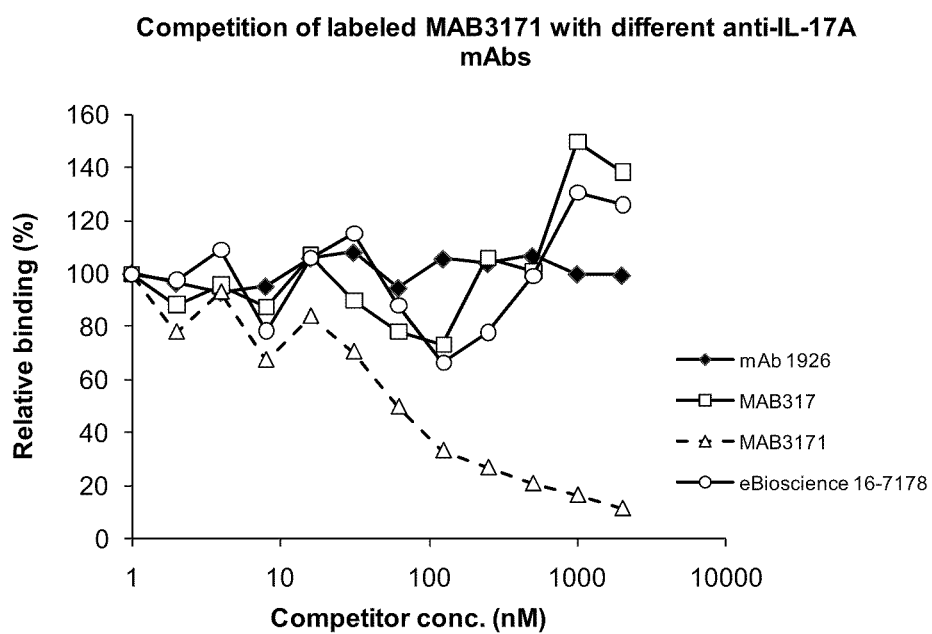
Figure 4E:
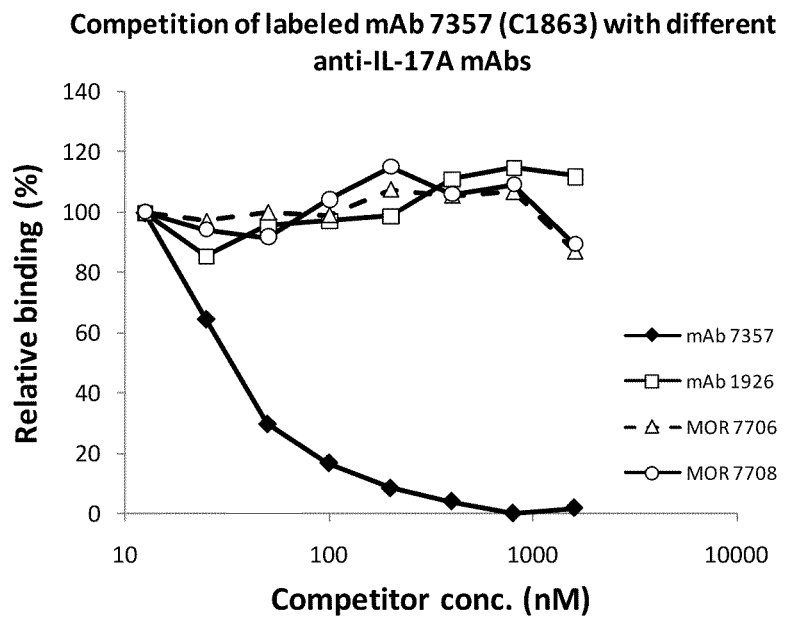
Figure 4F:
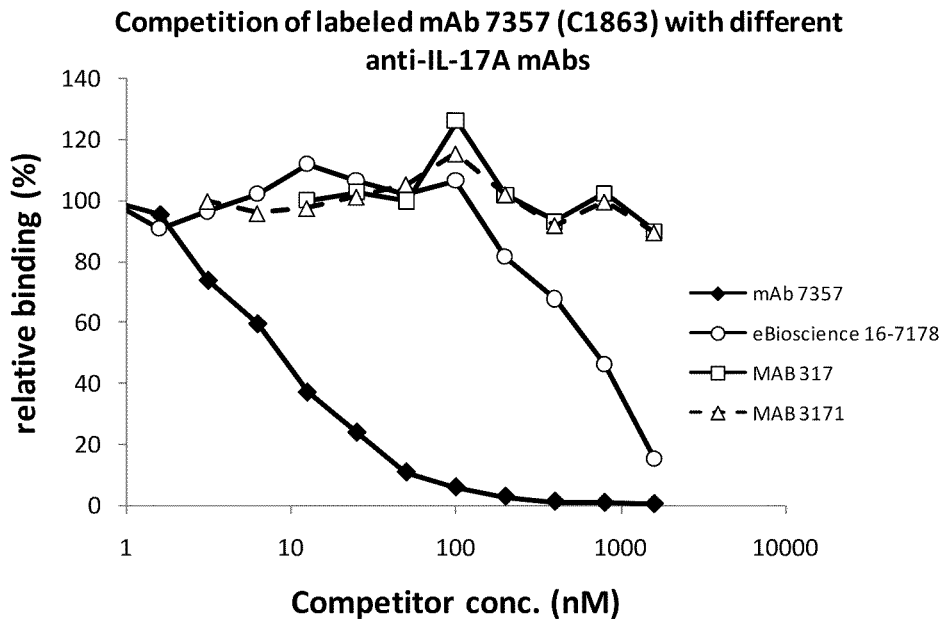

One aspect of the invention is an isolated antibody or fragment thereof, wherein the antibody binds specifically to human IL-17A having the sequence shown in SEQ ID NO:

105 at amino acid residues 56-68 (SEQ ID NO: 157) and 100-116 (SEQ ID NO: 158); or at residues L26, R55, E57, P59, E60, R61, Y62, S64, V65, W67, R101, E102, P103 and F110.

Another aspect of the invention is an isolated antibody or fragment thereof, wherein the antibody binds specifically to a P2 pocket cavity on human IL-17A, the P2 pocket cavity comprising amino acid residues V22, V24, L26, I28, Y62, L99, R101, F110, and L112 of SEQ ID NO: 105.

Another aspect of the invention is an isolated antibody or fragment that binds specifically to human IL-17A that competes for human IL-17A binding with a monoclonal antibody comprising the amino acid sequences of certain heavy chain complementarity determining regions (CDR) 1, 2 and 3 (HCDR1, HCDR2, HCDR3), the amino acid sequences of certain light chain complementarity determining reigons (CDR) 1, 2 and 3 (LCDR1, LCDR2, LCDR3), the amino acid sequences of certain heavy chain variable regions (VH) or the amino acid sequences of certain light chain variable regions (VL).

Another aspect of the invention is an isolated antibody or fragment that binds specifically to human IL-17A, comprising certain heavy chain variable region paratope amino acid residues and certain light chain variable region paratope amino acid residues that interact with certain residues of human IL-17A having the amino acid sequence shown in SEQ ID NO: 105.

Another aspect of the invention is an isolated antibody or fragment that binds specifically to human IL-17A, comprising a heavy chain variable region and a light chain variable region, wherein the antibody comprises a heavy chain variable region paratope selected from Chothia residues F56 and Y58; and a light chain variable region paratope selected from Chothia residues Y91, F93 and F94.

Another aspect of the invention is an isolated antibody or fragment that binds specifically human IL-17A, comprising a heavy chain variable region (VH) and a light chain variable region (VL), wherein the antibody comprises the amino acid sequences of certain heavy chain complementarity determining regions (CDR) 1, 2 and 3 (HCDR1, HCDR2, HCDR3), the amino acid sequences of certain light chain complementarity determining reigons (CDR) 1, 2 and 3 (LCDR1, LCDR2, LCDR3), the amino acid sequences of certain heavy chain variable regions (VH) or the amino acid sequences of certain light chain variable regions (VL).

Another aspect of the invention is an isolated antibody or fragment that specifically binds human IL-17A, wherein the antibody comprises the amino acid sequences of certain heavy chains and the amino acid sequences of certain light chains.

Another aspect of the invention is a pharmaceutical composition comprising the isolated antibody or fragment of the invention and a pharmaceutically acceptable carrier.

Another aspect of the invention is an isolated antibody heavy chain comprising the amino acid sequence shown in SEQ ID NOs: 67, 68, 69, 81, 82, 83, 84, 85, 86, 92, 93, 94, 95, 96, 97, 98, 99, or 100.

Another aspect of the invention is an isolated antibody light chain comprising the amino acid sequence shown in SEQ ID NOs: 76, 77, 78, 79, 80, 87, 88, 89, 90, or 91.

Another aspect of the invention is an isolated polynucleotide encoding an antibody heavy chain comprising the amino acid sequence shown in SEQ ID NO: 67, 68, 69, 81, 82, 83, 84, 85, 86, 92, 93, 94, 95, 96, 97, 98, 99, or 100.

Another aspect of the invention is an isolated polynucleotide encoding an antibody light chain comprising the amino acid sequence shown in SEQ ID NO: 76, 77, 78, 79, 80, 87, 88, 89, 90, or 91.

Another aspect of the invention is a vector comprising at least one polynucleotide of the invention.

Another aspect of the invention is a host cell comprising the vector of the invention.

Another aspect of the invention is a method of inhibiting interaction of human IL-17A with IL-17RA comprising: providing a human IL-17A and IL-17RA; and contacting the human IL-17A with an antagonist that binds the human IL-17A at least one amino acid residue selected from the group consisting of V22, V24, L26, I28, Y62, L99, R101, F110, and L112.

Another aspect of the invention si a method of inhibiting IL-17A biological activity, comprising: providing a human IL17-A and IL-17RA; and contacting the human IL-17A with an antagonist that binds the human IL-17A at at least one amino acid residue selected from the group consisting of V22, V24, L26, I28, Y62, L99, R101, F110, and L112.

Another aspect of the invention is a method of treating an inflammatory condition comprising administering a therapeutically effective amount of the isolated antibody of claim 3 or 7 to a patient in need thereof for a time sufficient to treat the inflammatory condition.

DETAILED DESCRIPTION OF THE INVENTION

All publications, including but not limited to patents and patent applications, cited in this specification are herein incorporated by reference as though fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein can be used in the practice for testing of the present invention, exemplary materials and methods are described herein. In describing and claiming the present invention, the following terminology will be used.

The term "antagonist" as used herein means a molecule that partially or completely inhibits, by any mechanism, IL-17A activity. Exemplary antagonists are antibodies, fusion proteins, peptides, peptidomimetics, nucleic acids, oligonucleotides and small molecules. The agent can be identified using well known assays for IL-17A activity described below.

The term "IL-17A antibody antagonist" or an "antibody reactive with IL-17A" as used herein refers to an antibody that is capable of, directly or indirectly, reducing or inhibiting IL-17A biological activity, blocking binding of IL-17A to its receptor, or inhibiting IL-17A receptor activation. For example, an antibody reactive with IL-17A can bind directly to IL-17A and neutralize IL-17A activity, i.e, block IL-17A signaling to reduce cytokine and chemokine release.

The term "IL-17A" (CTLA-8, IL-17, interleukin-17A) refers to a human IL-17A polypeptide having an amino acid sequence shown in GenBank Acc. No. NP_002181. SEQ ID NO: 105 shows the amino acid sequence of the mature human IL-17A. IL-17A in vivo forms homodimers of two monomers, which are designated monomer A and monomer B, or protomer A and protomer B, or protomer 1 and protomer 2, or chain A and chain B. IL-17A can also form a heterodimer with IL-17F. The term "IL-17A" comprises the monomer, the homodimer, and the heterodimer forms. The term "IL-17Amut6" refers to a variant of IL-17A having A70Q and A132Q substitutions. The amino acid sequence of the mature IL-17Amut6 is shown in SEQ ID NO: 106, and the cDNA sequence in SEQ ID NO: 112. IL-17A and IL-17Amut6 have comparable activities (PCT. Pat. Appl. No. WO09/003096).

The term "IL-17A receptor" as used herein comprises both receptor polypeptides, IL-17RA (GenBank Acc no: NP_055154, SEQ ID NO: 107) and IL-17RC (GenBank Acc No NP_703191, SEQ ID NO: 113), and homodimers or heterodimers of the two polypeptides.

The term "antibodies" as used herein is meant in a broad sense and includes immunoglobulin molecules including polyclonal antibodies, monoclonal antibodies including murine, human, human-adapted, humanized and chimeric monoclonal antibodies, antibody fragments, multispecific antibodies formed from at least two intact antibodies, dimeric, tetrameric or multimeric antibodies.

The term "monoclonal antibody" (mAb) as used herein means an antibody (or antibody fragment) obtained from a population of substantially homogeneous antibodies. Monoclonal antibodies are highly specific, typically being directed against a single epitope. The modifier "monoclonal" indicates the substantially homogeneous character of the antibody and does not require production of the antibody by any particular method.

Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$. Antibody light chains of any vertebrate species can be assigned to one of two clearly distinct types, namely kappa (κ) and lambda (λ), based on the amino acid sequences of their constant domains.

The term "antibody fragments" comprise at least a portion of an immunoglobulin molecule, such as a heavy chain complementarity determining region (HCDR), a light chain complementarity determining region (LCDR), a heavy chain variable region (VH), a light chain variable region (VL), a heavy chain constant region (CH), a light chain constant region (CL), or a framework region (FR) from either antibody heavy or light chain. An antibody may be a Fab, F(ab'), $F(ab')_2$, scFv, dsFv, or diabody. Structures of the above mentioned antibody fragments, and techniques for the preparation and use of the antibodies and fragments thereof are well known in the art.

An antibody variable region consists of a "framework" region interrupted by three "antigen-binding sites". The antigen-binding sites are defined using various terms: (i) Complementarity Determining Regions (CDRs), three in the VH (HCDR1, HCDR2, HCDR3), and three in the VL (LCDR1, LCDR2, LCDR3), are based on sequence variability (Wu and Kabat, J. Exp. Med. 132:211-250, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3), refer to the regions of an antibody variable domains which are hypervariable in structure as defined by Chothia and Lesk (Chothia and Lesk, Mol. Biol. 196:901-917, 1987). Other terms include "IMGT-CDRs" (Lefranc et al., Dev. Comparat. Immunol. 27:55-77, 2003) and "Specificity Determining Residue Usage" (SDRU) (Almagro, Mol. Recognit. 17:132-143, 2004). The International ImMunoGeneTics (IMGT) database (http://www_imgt_org) provides a standardized numbering and definition of antigen-binding sites. The correspondence between CDRs, HVs and IMGT delineations is described in Lefranc et al., Dev. Comparat. Immunol. 27:55-77, 2003.

"Chothia residues" as used herein are the antibody VL and VH residues numbered according to Al-Lazikani (Al-Lazikani et al., J. Mol. Biol. 273:927-48, 1997). Correspondence between the two most used numbering systems, Kabat (Kabat et al., Sequences of Immunological Interest, $5^{th}$ Ed. Public Health Service, NIH, Bethesda, Md., 1991) and Chothia (Chothia and Lesk, Mol. Biol. 196:901-17, 1987) in relation to sequential polypeptide numbering is shown in FIG. 3 for exemplary antibodies of the invention.

"Framework" or "framework sequences" are the remaining sequences of a variable region other than those defined to be antigen-binding site. Because the antigen-binding site can be defined by various terms as described above, the exact amino acid sequence of a framework depends on how the antigen-binding site was defined.

The term "substantially identical" as used herein means that the two antibody or antibody fragment amino acid sequences being compared are identical or have "insubstantial differences." Insubstantial differences are substitutions of 1, 2, 3, 4, 5, 6, 7, 8, 9, 10, 11, 12, 13, 14, or 15 amino acids in an antibody or antibody fragment amino acid sequence that do not adversely affect antibody properties. Amino acid sequences substantially identical to the sequences disclosed herein are also part of this application. In some embodiments, the sequence identity can be about 90%, 91%, 92%, 93%, 94%, 95%, 96%, 97%, 98%, 99% or higher. Percent identity can be determined for example by pairwise alignment using the default settings of the AlignX module of Vector NTI v.9.0.0 (Invitrogen, Carslbad, Calif.). The protein sequences of the present invention can be used as a query sequence to perform a search against public or patent databases to, for example, identify related sequences. Exemplary programs used to perform such searches are the XBLAST or BLASTP programs (http_//www_ncbi_nlm/nih_gov), or the GenomeQuest™ (GenomeQuest, Westborough, Mass.) suite using the default settings.

The term "in combination with" as used herein means that the described agents can be administered to an animal together in a mixture, concurrently as single agents or sequentially as single agents in any order.

The term "inflammatory condition" as used herein refers to acute or chronic localized or systemic responses to harmful stimuli, such as pathogens, damaged cells, physical injury or irritants, that are mediated in part by the activity of cytokines, chemokines, or inflammatory cells (e.g., neutrophils, monocytes, lymphocytes, macrophages) and is characterized in most instances by pain, redness, swelling, and impairment of tissue function.

The term "IL-17A-mediated inflammatory condition" as used herein refers to an inflammatory condition resulting at least partially from IL-17A biological activity, or caused by IL-17A activity. Exemplary IL-17A-mediated inflammatory conditions are psoriasis and rheumatoid arthritis.

The term "IL-17A-mediated condition" as used herein encompasses all diseases and medical conditions in which IL-17A plays a role, whether directly or indirectly, in the disease or medical condition, including the causation, development, progress, persistence or pathology of the disease or condition.

The term "epitope" as used herein means a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be composed of either or both contiguous or discontiguous amino acids that form a conformational spatial unit. For a discontiguous epitope, amino acids from differing portions of the linear sequence of the antigen come in close proximity in 3-dimensional space through the folding of the protein molecule.

The term "paratope" as used herein means a portion of an antibody to which an antigen specifically binds. A paratope can be linear in nature or can be discontinuous, formed by a spatial relationship between non-contiguous amino acids of an antibody rather than a linear series of amino acids. A "light chain paratope" and a "heavy chain paratope" or "light chain paratope amino acid residues" and "heavy chain paratope amino acid residues" refer to antibody light chain and heavy chain residues in contact with an antigen, respectively.

The term "specific binding" as used herein refers to antibody binding to a predetermined antigen with greater affinity than for other antigens or proteins. Typically, the antibody binds with a dissociation constant ($K_D$) of $10^{-7}$ M or less, and binds to the predetermined antigen with a $K_D$ that is at least ten fold less than its $K_D$ for binding to a non-specific antigen (e.g., BSA, casein, or any other specified polypeptide) other than the predetermined antigen. The phrases "an antibody recognizing an antigen" and "an antibody specific for an antigen" are used interchangeably herein with the term "an antibody specifically binding to an antigen" or "an antigen specific antibody" e.g. an IL-17A specific antibody. The dissociation constant can be measured using standard procedures.

The term "IL-17A biological activity" or "IL-17A activation" as used herein refers to any activity occurring as a result of IL-17A binding to the IL-17A receptor. Exemplary IL-17A biological activities result in increased secretion of IL-6 or IL-8, NF-κB activation, or regulation of downstream kinases sucn as ERK1, ERK2 and p38 upon binding to the IL-17A receptor. The release of cytokines and chemokines from cells, tissues or in circulation, NF-κB activation, or kinase phosporylation events can be measured using well known methods, for example immunoassays, immunoblotting, or reporter gene systems (Yao et al., Immunity 3:811-21, 1995; Awane et al., J. Immunol. 162:5337-44, 1999).

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "polypeptide" or "protein" means a molecule that comprises at least two amino acid residues linked by a peptide bond to form a polypeptide. Small polypeptides of less than 50 amino acids may be referred to as "peptides".

Conventional one and three-letter amino acid codes are used herein as follows:

| Amino acid | Three-letter code | One-letter code |
|---|---|---|
| Alanine | ala | A |
| Arginine | arg | R |
| Asparagine | asn | N |
| Aspartate | asp | D |
| Cysteine | cys | C |
| Glutamate | glu | E |
| Glutamine | gln | Q |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |
| Tyrosine | tyr | Y |
| Valine | val | V |

Compositions of Matter

The present invention provides IL-17A antibody antagonists capable of inhibiting IL-17A biological activity and uses of such antibodies. Exemplary mechanisms by which IL-17A activation may be inhibited by such antibodies include in vitro, in vivo or in situ inhibition of IL-17A homo-or heterodimerization, and blocking binding of IL-17A to the IL-17A receptor, inhibition of receptor dimerization, inhibition of kinase activity of downstream signaling pathways, or inhibition of IL-17A mRNA transcription. Other antibody antagonists capable of inhibiting IL-17A activation by other mechanisms are also within the scope of the various aspects and embodiments of the invention. These antagonists are useful as research reagents, diagnostic reagents and therapeutic agents.

The invention provides novel antigen-binding sites derived from human immunoglobulin gene libraries. The structure for carrying an antigen-binding site is generally an antibody heavy or light chain or portion thereof.

The invention provides an isolated antibody or fragment thereof that binds specifically to human IL-17A, comprising a heavy chain variable region (VH) and a light chain variable region (VL), wherein the antibody comprises the heavy chain complementarity determining region (CDR) 1, 2 and 3 (HCDR1, HCDR2 and HCDR3) amino acid sequences and the light chain complementarity determining region (CDR) 1, 2 and 3 (LCDR1, LCDR2 and LCDR3) amino acid sequences as shown in Table 1a.

TABLE 1a

| Family | MORmAb# | mAb# | LCDR1 | LCDR2 | LCDR3 | HCDR1 | HCDR2 | HCDR3 |
|---|---|---|---|---|---|---|---|---|
| 2 | 7702 | | 1 | 4 | 7 | 23 | 26 | 52 |
| | 7701 | | 1 | 4 | 7 | 23 | 27 | 52 |
| | 7708 | 624 | 1 | 4 | 7 | 23 | 28 | 52 |
| | 8297 | | 1 | 4 | 7 | 23 | 29 | 52 |
| | 8298 | | 1 | 4 | 7 | 23 | 30 | 52 |
| | 7785 | 3077 | 1 | 4 | 7 | 23 | 31 | 52 |
| | 8104 | 7024 | 1 | 4 | 7 | 23 | 32 | 52 |
| | 8105 | | 1 | 4 | 7 | 23 | 33 | 52 |
| | 7786 | | 1 | 4 | 7 | 23 | 34 | 52 |
| | Consensus sequence | | 1 | 4 | 7 | 23 | 35 | 52 |
| 6a | Clone 10 | | 2 | 5 | 8 | 24 | 36 | 53 |
| | Clone 11 | | 2 | 5 | 9 | 24 | 36 | 53 |
| | Clone 12 | | 2 | 5 | 10 | 24 | 36 | 53 |
| | Consensus sequence | | 2 | 5 | 11 | 24 | 36 | 53 |
| 6b | Clone 13 | | 2 | 5 | 12 | 24 | 36 | 53 |
| | 7706 | 4538 | 2 | 5 | 13 | 24 | 36 | 53 |
| | 8299 | 3584 | 2 | 5 | 13 | 24 | 36 | 54 |
| | 8300 | | 2 | 5 | 13 | 24 | 36 | 55 |
| | 8301 | | 2 | 5 | 13 | 24 | 36 | 56 |
| | Clone 15 | | 2 | 5 | 14 | 24 | 36 | 53 |
| | Clone 16 | | 2 | 5 | 15 | 24 | 36 | 53 |
| | 7775 | 732 | 2 | 5 | 16 | 24 | 36 | 53 |
| | 8101 | | 2 | 5 | 16 | 24 | 36 | 54 |
| | 8102 | | 2 | 5 | 16 | 24 | 36 | 55 |
| | 8103 | 4168 | 2 | 5 | 16 | 24 | 36 | 56 |
| | Consensus sequence | | 2 | 5 | 17 | 24 | 36 | 57 |
| 19a | Clone 179 | | 3 | 6 | 18 | 25 | 37 | 58 |
| | Clone 180 | | 3 | 6 | 18 | 25 | 38 | 58 |
| | 7709 | | 3 | 6 | 18 | 25 | 39 | 58 |
| | Clone 182 | | 3 | 6 | 18 | 25 | 40 | 58 |
| | 7700 | 1926 | 3 | 6 | 18 | 25 | 41 | 58 |
| | 8095 | | 3 | 6 | 18 | 25 | 42 | 58 |
| | 8096 | | 3 | 6 | 18 | 25 | 43 | 58 |
| | 8097 | | 3 | 6 | 18 | 25 | 41 | 59 |
| | 8098 | | 3 | 6 | 18 | 25 | 41 | 60 |
| | 8141 | | 3 | 6 | 19 | 25 | 41 | 58 |
| | 8142 | | 3 | 6 | 20 | 25 | 41 | 58 |
| | 8143 | | 3 | 6 | 21 | 25 | 41 | 58 |
| | 8160 | 7146 | 3 | 6 | 19 | 25 | 41 | 60 |
| | 8161 | | 3 | 6 | 20 | 25 | 41 | 60 |
| | 8162 | | 3 | 6 | 21 | 25 | 41 | 60 |
| | 8302 | 6785 | 3 | 6 | 18 | 25 | 43 | 60 |
| | 8303 | | 3 | 6 | 20 | 25 | 43 | 60 |
| | | 5548 | 3 | 6 | 19 | 25 | 43 | 60 |
| | 7768 | | 3 | 6 | 18 | 25 | 44 | 58 |
| | Clone 185 | | 3 | 6 | 18 | 25 | 45 | 58 |
| | Consensus sequence | | 3 | 6 | 22 | 25 | 46 | 61 |
| 19b | Clone 186 | | 3 | 6 | 18 | 25 | 47 | 58 |
| | Clone 187 | | 3 | 6 | 18 | 25 | 48 | 58 |
| | Clone 188 | | 3 | 6 | 18 | 25 | 49 | 58 |
| | Clone 189 | | 3 | 6 | 18 | 25 | 50 | 58 |
| | Consensus sequence | | 3 | 6 | 18 | 25 | 51 | 58 |

In certain embodiments, the invention provides an isolated antibody or fragment that binds specifically to human IL-17A, comprising a VH and a VL, wherein the antibody comprises the HCDR1, HCDR2 and HCDR3 amino acid sequences as shown in SEQ ID NOs: 23, 35 and 52, wherein the HCDR2 of SEQ ID NO: 35 is further defined as shown in Formula (I):

$$Xaa_1\text{-I-I-P-W-F-G-}Xaa_2\text{-T-}Xaa_3\text{-Y-A-Q-K-F-Q-G}, \quad (I)$$

wherein
Xaa$_1$ may be His, Met, Arg, Ser or Tyr;
Xaa$_2$ may be Trp, Thr or Tyr; and
Xaa$_3$ may be Tyr, Phe, Ser or Asp.

In other embodiments, the invention provides an isolated antibody or fragment that binds specifically to human IL-17A, comprising a VH and a VL, wherein the antibody comprises the LCDR1, LCDR2 and LCDR3 amino acid sequences as shown in SEQ ID NOs: 2, 5 and 11, wherein the LCDR3 of SEQ ID NO: 11 is further defined as shown in Formula (II):

$$Xaa_4\text{-Q-}Xaa_5\text{-}Xaa_6\text{-}Xaa_7\text{-}Xaa_8\text{-}Xaa_9\text{-}Xaa_{10}, \quad (II)$$

wherein
Xaa$_4$ may be His or Gln;
Xaa$_5$ may be Phe or Gly;
Xaa$_6$ may be Thr, Val or Asn;
Xaa$_7$ may be Ile, Thr or Tyr;
Xaa$_8$ may be Pro or Arg;
Xaa$_9$ may be Ser or Pro; and
Xaa$_{10}$ may be His, Phe or Leu.

In other embodiments, the invention provides an isolated antibody or fragment that binds specifically to binding human IL-17A, comprising a VH and a VL, wherein the antibody comprises the LCDR1, LCDR2, and LCDR3 amino acid sequences as shown in SEQ ID NOs: 2, 5 and 17, wherein the LCDR3 of SEQ ID NO: 17 is further defined as shown in Formula (III):

$$Xaa_{11}\text{-}Q\text{-}Xaa_{12}\text{-}Xaa_{13}\text{-}Xaa_{14}\text{-}Xaa_{15}\text{-}Xaa_{16}\text{-}Xaa_{17}\text{-}Xaa_{18}\text{-}T, \quad (III)$$

wherein
Xaa$_{11}$ may be Gln or Thr;
Xaa$_{12}$ may be Ser or Tyr;
Xaa$_{13}$ may be Asn, Arg, Val or Tyr;
Xaa$_{14}$ may be His or Ser;
Xaa$_{15}$ may be Ile, Thr, Leu, Ala or Ser;
Xaa$_{16}$ may be Pro, Leu or Ser;
Xaa$_{17}$ may be Pro, Ser, Phe or Leu; and
Xaa$_{18}$ may be Ala, Leu or Asp.

In other embodiments, the invention provides an isolated antibody or fragment that binds specifically to human IL-17A, comprising a VH and a VL, wherein the antibody comprises the HCDR1, HCDR2 and HCDR3 amino acid sequences as shown in SEQ ID NOs: 24, 36 and 57, wherein the HCDR3 of SEQ ID NO: 57 is further defined as shown in Formula (IV):

$$E\text{-}V\text{-}D\text{-}S\text{-}Xaa_{19}\text{-}Y\text{-}Y\text{-}S\text{-}Y\text{-}F\text{-}D\text{-}I, \quad (IV)$$

wherein
Xaa$_{19}$ is Met, Ile, Leu or Thr.

In other embodiments, the invention provides an isolated antibody or fragment that binds specifically to human IL-17A, comprising a VH and a VL, wherein the antibody comprises the LCDR1, LCDR2 and LCDR3 amino acid sequences as shown in SEQ ID NOs: 3, 6 and 22, wherein the LCDR3 of SEQ ID NO: 22 is further defined as shown in Formula (V):

$$G\text{-}S\text{-}Y\text{-}D\text{-}F\text{-}F\text{-}L\text{-}G\text{-}Xaa_{20}\text{-}I\text{-}V, \quad (V)$$

wherein
Xaa$_{20}$ is Met, Leu, Thr or Tyr.

In other embodiments, the invention provides an isolated antibody or fragment that binds specifically to human IL-17A, comprising a VH and a VL, wherein the antibody comprises the HCDR1, HCDR2 and HCDR3 amino acid sequences as shown in SEQ ID NOs: 25, 46 and 61, wherein the HCDR2 of SEQ ID NO: 46 is further defined as shown in Formula (VI):

$$Xaa_{21}\text{-}I\text{-}Xaa_{22}\text{-}Xaa_{23}\text{-}Xaa_{24}\text{-}Xaa_{25}\text{-}Xaa_{26}\text{-}Xaa_{27}\text{-}Xaa_{28}\text{-}Xaa_{29}\text{-}Y\text{-}A\text{-}D\text{-}S\text{-}V\text{-}K\text{-}G, \quad (VI)$$

wherein
Xaa$_{21}$ may be Ala, Gly, Thr or Val;
Xaa$_{22}$ may be Asn or Ser;
Xaa$_{23}$ may be Gly, Met, Lys, Ile, Leu or His;
Xaa$_{24}$ may be Leu, Asp, Ala, His, Thr, Gly or Ser;
Xaa$_{25}$ may be Gly or Ser;
Xaa$_{26}$ may be Thr, Gly, Tyr or Asp;
Xaa$_{27}$ may be His, Trp, Tyr or Phe;
Xaa$_{28}$ may be Lys, Thr or Ile; and
Xaa$_{29}$ may be Tyr, Phe or Asn, and
the HCDR3 of SEQ ID NO: 61 is defined as shown in Formula (VII):

$$Q\text{-}L\text{-}Xaa_{30}\text{-}L\text{-}D\text{-}V, \quad (VII)$$

wherein
Xaa$_{30}$ may be Met, Leu or Thr.

In other embodiments, the invention provides an isolated antibody or fragment that binds specifically to human IL-17A, comprising a VH and a VL, wherein the antibody comprises the HCDR1, HCDR2 and HCDR3 amino acid sequences as shown in SEQ ID NOs: 25, 51 and 58, wherein the HCDR2 of SEQ ID NO: 51 is further defined as shown in Formula (VIII):

$$V\text{-}T\text{-}S\text{-}Xaa_{31}\text{-}Xaa_{32}\text{-}Xaa_{33}\text{-}Xaa_{34}\text{-}T\text{-}Y\text{-}Y\text{-}A\text{-}Xaa_{35}\text{-}S\text{-}V\text{-}K\text{-}G, \quad (VIII)$$

wherein
Xaa$_{31}$ may be Ala, Lys, Met or His;
Xaa$_{32}$ may be Asn, Met, Thr or Arg;
Xaa$_{33}$ may be Gly or Asp;
Xaa$_{34}$ may be Arg, His or Asn; and
Xaa$_{35}$ may be Asp or Gly.

Antibodies whose antigen-binding site amino acid sequences are substantially identical to those shown in Table 1a (SEQ ID NOs: 1-61) are encompassed within the scope of the invention. Typically, this involves one or more amino acid substitutions with an amino acid having similar charge or hydrophobic or stereochemical characteristics, and are made to improve antibody properties, for example stability or affinity. For example, a conservative substitution may involve a substitution of a native amino acid residue with a nonnative residue such that there is little or no effect on the polarity or charge of the amino acid residue at that position. Furthermore, any native residue in the polypeptide may also be substituted with alanine, as has been previously described for alanine scanning mutagenesis (MacLennan et al., Acta Physiol. Scand. Suppl. 643:55-67, 1998; Sasaki et al., Adv. Biophys. 35:1-24, 1998). Conservative substitutions will produce molecules having functional and chemical characteristics similar to those of the molecule from which such modifications are made. Non-conservative substitutions in the functional and/or chemical characteristics of the molecules may be accomplished by selecting substitutions in the amino acid sequence that differ significantly in their effect on maintaining (1) the structure of the molecular backbone in the area of the substitution, for example, as a sheet or helical conformation, (2) the charge or hydrophobicity of the molecule at the target site, or (3) the size of the molecule. Desired amino acid substitutions (whether conservative or non-conservative) can be determined by those skilled in the art at the time such substitutions are desired. For example, amino acid substitutions can be used to identify residues important for the function of the antibodies, such as residues affecting affinity, or residues that impart undesireable properties such as aggregation. Exemplary amino acid substitutions are shown in Table 1b, and FIG. 1.

Substitutions in the framework regions, in contrast to antigen-binding sites may also be made as long as they do not adversely affect the properties of the antibody. Framework substitutions can be made for example at the Vernier Zone residues (U.S. Pat. No. 6,649,055) to improve antibody affinity or stability. Substitutions can also be made at those framework positions in the antibody that differ in sequence when compared to the homologous human germline gene sequences to reduce possible immunogeneicity. These modifications can be done for example to antibodies derived from de novo antibody libraries, such as pIX libraries.

TABLE 1b

| Original residue | Exemplary substitutions | More conservative substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |

TABLE 1b-continued

| Original residue | Exemplary substitutions | More conservative substitutions |
|---|---|---|
| Gln | Asn | Asn |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser, Ala | Ser |
| Trp | Tyr, Phe | Tyr |
| Tyr | Trp, Phe, Thr, Ser | Phe |
| Val | Ile, Met, Leu, Phe, Ala, Norleucine | Leu |

Conservative amino acid substitutions also encompass non-naturally occurring amino acid residues which are typically incorporated by chemical peptide synthesis rather than by synthesis in biological systems. Amino acid substitutions can be done for example by PCR mutagenesis (U.S. Pat. No. 4,683,195). Libraries of variants can be generated using well known methods, for example using random (NNK) or non-random codons, for example DVK codons, which encode 11 amino acids (ACDEGKNRSYW), and screening the libraries or variants with desired properties, as shown in Example 1. FIG. 1 shows substitutions made to five parent IL-17A antibody antagonists within the LCDR3, HCDR2 and HCDR3 regions to improve antibody properties. Improved properties, such as affinity or stability can be measured by well known methods.

In other embodiments, the invention provides an isolated antibody or fragment that binds specifically to human IL-17A, comprising a VH and a VL, wherein the antibody comprises certain VH and VL sequences, and also provides for each isolated VH and VL as shown in Table 2.

TABLE 2

| SEQ ID NO: | | | | SEQ ID NO: | | | |
|---|---|---|---|---|---|---|---|
| MOR# | VL | VH | mAb# | VL | VH | Light chain | Heavy chain |
| Family 2 | | | | | | | |
| 7708 | 62 | 67 | 624 | 76 | 67 | 87 | 92 |
| 7785 | 62 | 68 | 3077 | 76 | 68 | 87 | 93 |
| 8104 | 62 | 69 | 7024 | 76 | 69 | 87 | 94 |
| Family 6b | | | | | | | |
| 7706 | 63 | 70 | 4538 | 77 | 81 | 88 | 95 |
| 8299 | 63 | 71 | 3584 | 77 | 82 | 88 | 96 |
| 7775 | 64 | 70 | 732 | 78 | 81 | 89 | 95 |
| 8103 | 64 | 72 | 4168 | 78 | 83 | 89 | 97 |
| Family 19a | | | | | | | |
| 7700 | 65 | 73 | 1926 | 79 | 84 | 90 | 98 |
| 8160 | 66 | 74 | 7146 | 80 | 85 | 91 | 99 |
| 8302 | 65 | 75 | 6785 | 79 | 86 | 90 | 100 |
|  |  |  | 5548 | 80 | 86 | 91 | 100 |

Although the embodiments illustrated in the Examples comprise pairs of variable regions, pairs of full length antibody chains, or pairs of CDR1, CDR2 and CDR3 regions, one from a heavy chain and one from a light chain, a skilled artisan will recognize that alternative embodiments may comprise single heavy chain variable regions or single light chain variable regions, single full length antibody chains, or CDR1, CDR2 and CDR3 regions from one antibody chain, either heavy or light. The single variable region, full length antibody chain or CDR1, CDR2 and CDR3 region of one chain can be used to screen for corresponding domains in another chain, the two chains capable of forming an antibody that specifically binds IL-17A. The screening may be accomplished by phage display screening methods using, e.g., a hierarchical dual combinatorial approach disclosed in PCT Publ. No. WO92/01047. In this approach, an individual colony containing either a H or L chain clone is used to infect a complete library of clones encoding the other chain (L or H), and the resulting two-chain specific antigen-binding domain is selected in accordance with phage display techniques as described.

In other embodiments, the invention provides an isolated antibody or fragment that binds specifically to human IL-17A, comprising a VH and a VL having amino acid sequences at least 90% identical to the VH and VL amino acid sequences shown in Table 2.

In other embodiments, the invention provides an isolated antibody or fragment that binds specifically to human IL-17A, comprising a VH and a VL having amino acid sequences at least 95% identical to the VH and VL amino acid sequences shown in Table 2.

In another aspect, the invention provides an isolated antibody or fragment having certain heavy chain and light chain amino acid sequences as shown in Table 2. In addition to numbering antibody residues sequentially, polypeptides encoding antibody chains can be numbered based on Kabat's or Chothia's numbering (Kabat et al., sequences of Proteins of Immunological Interest, 5th Ed. Public Health Service, National Institutes of Health, Bethesda, Md., 1991; Chothia and Lesk, Mol. Biol. 196:901-917, 1987). Examples of correspondence between sequential, Kabat and Chotia numbering for a select antibody chains are shown in FIG. 3. The positions highlighted in gray indicate antibody CDR regions.

In other embodiments, the invention provides an isolated antibody or fragment that binds specifically to human IL-17A, comprising a VH and a VL, wherein the antibody comprises a heavy chain variable region paratope selected from Chothia residues S51, T53, F56, Y58, Q95, L96 and T97 and a light chain variable region paratope selected from Chothia residues Y32, D50, Y91, F93 and F94. The heavy chain paratope and the light chain paratope Chothia residues correspond to heavy chain residues S52, T54, F57, Y59, Q99, L100 and T101 of SEQ ID NO: 86 and light chain residues Y31, D49, Y90, F92 and F93 of SEQ ID NO: 79.

In other embodiments, the invention provides an isolated antibody or fragment that binds specifically to human IL-17A, comprising heavy chain variable region paratope amino acid residues that interact with residues of human IL-17A having the amino acid sequence shown in SEQ ID NO: 105, comprising:

a first threonine residue that interacts with R55 or E57 of human IL-17A;

a glutamine residue that interacts with R55 or E57 of human IL-17A;

a lysine residue that interacts with E57 of human IL-17A;

a tyrosine residue that interacts with P59, E60 or R101 of human IL-17A;

a phenylalanene residue that interacts with E60, R101, E102 or P103 of human IL-17A;

a serine residue that interacts with E60 of human IL-17A; and a second threonine residue that interacts with E60 of human IL-17A.

In other embodiments, the invention provides an isolated antibody or fragment that binds specifically to human IL-17A, comprising light chain variable region paratope amino acid residues that interact with residues of human IL-17A having the amino acid sequence shown in SEQ ID NO: 105, comprising:

a first phenylalanine residue that interacts with L26 of human IL-17A;

an aspartic acid residue that interacts with R55 or W67 of human IL-17A;

a first tyrosine residue that interacts with P59, S64 or R101 of human IL-17A;

a second phenylalanine residue that interacts with P59, E60, R61, Y62, R101 or F110 of human IL-17A; and a second tyrosine residue that interacts with V65 of human IL-17A.

In another embodiment, the invention provides an isolated antibody or fragment that binds specifically to human IL-17A, comprising heavy chain variable region paratope amino acid residues and light chain variable region paratope amino acid residues that interact with residues of human IL-17A having the amino acid sequence shown in SEQ ID NO: 105, comprising:

a tyrosine residue in the heavy chain variable region that interacts with R101 of human IL-17A;

a phenylalanine residue in the heavy chain variable region that interacts with R101, of human IL-17A;

a first phenylalanine residue in the light chain variable region that interacts with Y62 and R101 of human IL-17A;

a second phenylalanine residue in the light chain variable region that interacts with L26 and F110 of human IL-17A; and a tyrosine residue in the light chain variable region that interacts with R101 of human IL-17A.

In another embodiment, the invention provides an isolated antibody or fragment that binds specifically to human IL-17A, comprising a heavy chain variable region and a light chain variable region, wherein the antibody comprises:

a heavy chain variable region paratope selected from Chothia residues F56 and Y58; and a light chain variable region paratope selected from Chothia residues Y91, F93 and F94.

The heavy chain paratope Chothia residues F56 and Y58 and the light chain paratope Chothia residues Y91, F92 and F94 are residues in direct contact with IL-17A residues L26, Y62, R101 and F110. These IL-17A residues are part of both the Fab6468 epitope and the P2 pocket cavity (see below). While not wishing to be bound to any particular theory, it is believed that interaction between the Fab6468 and IL-17A at these select residues may be sufficient for the antibody to block IL-17A activity.

Fully human mAbs lacking any non-human sequences can be prepared and optimized from phage display libraries by techniques referenced in, e.g., Knappik et al., J. Mol. Biol. 296:57-86, 2000; and Krebs et al., J. Immunol. Meth. 254: 67-84 2001. In an exemplary method, the antibodies of the invention are isolated from libraries expressing antibody heavy and light chain variable regions as fusion proteins with bacteriophage pIX coat protein. The antibody libraries are screened for bining to human IL-17mut6 (SEQ ID NO: 105), and the obtained positive clones are further characterized, the Fabs isolated from the clone lysates, and expressed as full length IgGs. Exemplary antibody libraries and screening methods are described in Shi et al., J. Mol. Biol. 397:385-96, 2010; PCT Pat. Appl. No. WO09/085462, and U.S. Ser. No. 12/546,850; U.S. Pat. Nos. 5,223,409, 5,969,108, and 5,885,793).

The resulting mAbs can further be modified in their framework regions to change certain framework residues to those present in a matching human germline, as exemplified within.

Antibodies of the invention binding specific IL-17A epitopes can be made by immunizing humanized mice expressing human immunoglobulin loci (Lonberg et al., Nature 368:856-9, 1994; Fishwild et al., Nature Biotechnology 14:845-51, 1996; Mendez et al., Nature Genetics 15:146-56, 1997, U.S. Pat. Nos. 5,770,429, 7,041,870, and 5,939, 598) or Balb/c mice with the peptides encoding the epitopes, for example peptide $_{56}$NEDPERYPSVIWE$_{68}$ (SEQ ID NO: 157) or $_{100}$RREPPHCPNSFRLEKIL$_{116}$ (SEQ ID NO: 158) and using the hybrodima method of Kohler et al., Nature 256:495-97. The resulting antibodies are tested for their binding to the epitope using standard methods. The identified mAbs can further be modified by incorporating altered framework support residues to preserve binding affinity by techniques such as those disclosed in Queen et al., Proc. Natl. Acad. Sci. (USA), 86:10029-32, 1989 and Hodgson et al., Bio/Technology, 9:421, 1991.

Isolated antibodies having certain paratope residues (eg., the core paratope residues defined in Table 10) that bind specifically to human IL-17A can be made, for example, by grafting the paratope residues into a suitable scaffold, assembling the engineered scaffolds into full antibodies, expressing the resulting antibodies, and testing the antibodies for binding to IL-17A or for an effect on IL-17A biological activity. Exemplary scaffolds are amino acid sequences of human antibody variable regions encoded by human germline genes. The scaffolds can be selected based on for example overall sequence homology, % identity between the paratope residues, or canonical structure class identity between the scaffold and an exemplary antibody, such as mAb6785. Human antibody germline genes are disclosed in, for example, Tomlinson et al., J. Mol. Biol 227:776-798, and at the International ImMunoGeneTics (IMGT) database (http_://_www_imgt_org). Consensus human framework regions can also be used, e.g., as described in U.S. Pat. No. 6,054,297. Selection of suitable scaffold can be done for example according to methods described in PCT Publ. No. WO10/045340.

Exemplary human germline genes that can be used as scaffolds onto which the paratope residues are grafted are the genes encoded by the Vλ3, Vh3, Jλ, and the Jh frameworks. Exemplary Vκ3 genes are IGLV3-1, IGLV3-9, IGLV3-10, IGLV3-12, IGLV3-16, IGLV3-19, IGLV3-21, IGLV3-22, IGLV3-25, IGLV3-27, and IGLV3-32 (IMGT nomenclature, *01 alleles), (SEQ ID NOs: 117-127, respectively). Exemplary Jλ genes are IGLJ1, IGLJ2, IGLJ3, IGLJ4, IGLJ5, IGLJ6, and IGLJ7 (SEQ ID NOs: 128-134, respectively). Exemplary Vh3 genes are IGHV3-7, IGHV3-9, IGHV3-11, IGHV3-16, IGHV3-19, IGHV3-20, IGHV3-21, IGHV3-23, IGHV3-30, IGHV3-30*03, IGHV3-33, IGHV3-45, IGHV3-48, IGHV3-64, and IGHV3-74 (IMGT nomenclature, *01 alleles except when different allele is specified) (SEQ ID NO:s 135-150, respectively). Exemplary Jh genes are IGHJ1, IGHJ2, IGHJ3, IGHJ4, IGHJ5, and IGHJ6 (SEQ ID NO:s 151-156, respectively). The germline J-regions are used in their entirety or in part to select FR4 sequences. For example, the mAb6785 light chain paratope residues can be grafted into a Vλ3 protein framework encoded by IGLV3-1 (SEQ ID NO: 117) that is joined to the J region sequence encoded by IGLJ2 (SEQ ID NO: 129) with insertion of a single amino acid residue between the IGLV3-1 and IGLJ2 sequences, for example methionine. The Vλ3 protein framework encoded by IGLV3-1 may contain additional substitutions, for example a substitution of cysteine residue at position 33 of SEQ ID NO: 117 ("ACW") with for example asparagine; and substitution of residūes 1-3 of SEQ ID NO: 117 ("SYE") with an amino-terminal sequence common to other lambda chain families, such as "QSV" of IGLV1 family. Sequences from other exemplary functional Vλ3 and Jλ genes can be used for grafting mAb6785 light chain paratope residues with the insertion of zero, one, or two amino acid residues between the carboxy-terminus encoded by the Vλ3 genes and the amino terminus encoded by the Jλ genes, such that the length of the CDR3 region is 11 amino acids. For example, methionine and isoleucine can be inserted between IGLV3-22 (SEQ ID NO: 124) and IGLJ2 (SEq ID NO: 129). FIG. 2A shows alignment of exemplary light chain scaffolds that can be used for grafting. The mAb6785 heavy chain paratope residues can be grafted onto for example a Vh3 framework encoded by IGHV3-23 (SEQ ID NO: 142), that is joined to the J region FR4 sequence (11 C-terminal amino acids e.g. "WGQGTLVTVSS") of IGHJ1 (SEQ ID NO: 151), with the insertion of about about 5-7 residues, for example 6 residues, constituting HCDR3, between the V and the J regions. The inserted HCDR3 about 5-7 residues include insertion of glutamine, leucine and threonine, e.g. 3 of the paratope residues from mAb6785 Vh (Table 10). Sequences from other exemplary functional Vh3 and Jh genes can be used for grafting mAb6785 heavy chain paratope residues. In some cases, one C-terminal amino acid from the Vh3 gene may be deleted before insertion of the about 5-7 residues constituting the HCDR3 so that only FR3 sequences are included in the scaffold. Sequences from other Vh3 genes that encode a CDR2 of 17 residues (residues 50-66 of IGHV3-23 (SEQ Id NO: 142) can also be used, and the FR4 sequences of other Jh genes can be substituted in place of IGJH1.

The specific binding to human IL-17A and biological activity of the resulting antibody can be evaluated using standard methods. Alignments of the mAb6785 light chain variable regions and heavy chain variable regions with the exemplary Vh3, Vλ3, Jλ or Jh genes are shown in FIGS. 2A and 2B. Alternatively, the extended paratope residues of mAb6785, as defined in Table 10, can be used in place of the core paratope residues. The paratope-grafted engineered antibodies can further be modified by substitutions of the Vernier Zone residues (U.S. Pat. No. 6,639,055) or the Affinity Determining Residues (U.S. Pat. Appl. No. 2010/0261620; Cobaugh et al., J Mol Biol. 378:622-33, 2008) to improve antibody properties for example affinity. As long as the paratope-grafted antibody retains binding to IL-17A, the framework amino acid sequence in the paratope-grafted antibody may be 70%, 75%, 80%, 85%, 90%, 95%, 96%, 97%, 98%, or 99% identical to the mAb6785 framework sequences. Allelic variants of the exemplary germline gene frameworks can be used in place of the V and J region protein sequences. Th sequences of the allelic variants are well known and can be obtained at the International ImMunoGeneTics (IMGT) database (http_://_www_imgt_org).

Sequences from the antigen-binding sites can be grafted in addition to the paratope residues using standard methods. For example, a complete HCDR3 or LCDR3 may be grafted.

Another embodiment of the invention is an isolated antibody or fragment that binds specifically to human IL-17A that competes for human IL-17A binding with a monoclonal antibody comprising certain HCDR1, HCDR2 and HCDR3, and LCDR1, LCDR2 and LCDR3 amino acid sequences. Examplary monoclonal antibodies of the invention are an isolated antibody comprising HCDR1, HCDR2 and HCDR3 amino acid sequences as shown in SEQ ID NOs: 25, 43 and 60 and the LCDR1, LCDR2 and LCDR3 amino acid sequences as shown in SEQ ID NOs: 3, 6 and 18.

Competition between specific binding to IL-17A can be assayed in vitro using well known methods. For example, binding of MSD Sulfo-Tag™ NHS-ester -labeled antibody to IL-17A in the presence of an unlableled antibody can be assessed by ELISA.

Another embodiment of the invention is an isolated antibody or antibody or fragment thereof, wherein the antibody binds specifically to human IL-17A having the sequence shown in SEQ ID NO: 105 at amino acid residues 56-68 (SEQ ID NO: 157) and 100-116 (SEQ ID NO: 158); or at residues L26, R55, E57, P59, E60, R61, Y62, S64, V65, W67, R101, E102, P103 and F110.

Several well known methodologies can be employed to determine the binding epitope of the antibodies of the invention. For example, when the structures of both individual components are known, in silico protein-protein docking can be carried out to identify compatible sites of interaction. Hydrogen-deuterium (H/D) exchange can be carried out with the antigen and antibody complex to map regions on the antigen that may be bound by the antibody. Segment and point mutagenesis of the antigen can be used to locate amino acids important for antibody binding. Co-crystal structure of antibody-antigen complex is used to identify residues contributing to the epitope and paratope.

Previously described anti-IL-17A antibodies bind to epitopes on IL-17A distinct from the epitope for Fab6468 described in the present invention. Antibodies binding human IL-17A (SEQ ID NO: 105) residues 74-85, 46-53, 71-87, 80-86, 11-18, 29-41 or 54-62 have been described (PCT Publ. Nos. WO08/021156, WO07/106769, WO07/149032, WO07/070750; US Appl. No. US2008/095775, respectively). Conformational epitopes have been described in PCT Publ. No. WO09/130459 and Gerhardt et al., J. Mol. Biol: 394:901-21, 2009.

Another embodiment of the invention is an isolated antibody or fragment thereof, wherein the antibody binds specifically to a P2 pocket cavity on IL-17A, the P2 pocket cavity comprising of amino acid residues V22, V24, L26, I28, Y62, L99, R101, F110, and L112 of SEQ ID NO: 105.

Co-crystal structure of IL-17A homodimer with the anti-IL-17A Fab6468 identified a hydrophobic P2 pocket cavity on the surface of the IL-17A homodimer, which is likely to be involved in IL-17RA binding (see Examples). The "P2 pocket cavity" as used herein refers to a tertiary hydrophobic structural cavity on IL-17A homodimer, where the surface exposed residues in the P2 pocket are V24, L26, I28, Y62, L99, R101, F110 and L112 on monomer A and V22, V24 and L112 on monomer B, and vice versa. Select antibodies of the invention reactive with IL-17A, for example Fab6468, have direct contacts with the P2 pocket cavity residues L26, Y62, R101 and F110, which residues are also part of the Fab6468 epitope. While not wishing to be bound by any particular theory, it is assumed that the antibodies of the invention binding the select IL-17A P2 pocket cavity residues block interaction between IL-17A and IL-17RA. Based on co-crystal structure, the phenlylalanine motif (FF) at residues 93 and 94 in a light chain (SEQ ID NO: 79) of Fab6468 blocks the IL-17A/IL-17RA interaction, and thus is a P2 pocket cavity blocker. Other P2 pocket cavity blocker antagonists are also within the scope of this invention, such as novel peptides or small molecules. These can be modeled based on the IL-17A/Fab6468 co-structure, and screened for their ability to replace Fab6468 binding to IL-17A. For example, peptide inhibitors can be screened from random peptide libraries that have incorporated the FF motif (for example libraries of XXXXFFXX; X indicated any amino acid; F=phenylalanine) and displayed on bacteriophage as a fusion with for example pIII, pVII or pIX coat protein (U.S. Pat. No. 5,223,409; Gao et al., Proc. Natl. Acad. Sci. USA, 96:6025-30, 1999, Tornetta et al., J. Immunol. Methods. 360:39-46, 2010; Shi et al., J.

Mol. Biol. 397:385-96, 2010) and subsequently tested for their inhibition of Fab6468 binding to IL-17A, and inhibition of IL-17A activity.

Small molecules may be screened using libraries of synthetic or natural compounds, or any combination thereof, and the resulting primary positive hits can be readily modified to produce structural analogs of the agents. Methods of making peptide libraries and pIX fusions, and screening the resulting libraries are well known.

Another embodiment of the invention of a method of inhibiting interaction of human IL-17A with IL-17RA comprising:
  providing human IL-17A and IL-17RA; and
  contacting human IL-17A with an antagonist that specifically binds human IL-17A at at least one amino acid residue selected from the group consisting of: V22, V24, L26, I28, Y62, L99, R101, F110, and L112.

Another embodiment of the invention is a method of inhibiting human IL-17A biological activity, comprising:
  providing human IL17-A and IL-17RA; and
  contacting human IL-17A with an antagonist that specifically binds human IL-17A at at least one amino acid residue selected from the group consisting of: V22, V24, L26, I28, Y62, L99, R101, F110, and L112.

Human IL-17A and IL-17RA can be provided as isolated proteins or fusion proteins. Human IL-17A homodimer can be purified from media of activated Th17 cells prepared by in vitro stimulation of naive CD4 T cells by two anti-CD3/anti-CD28 stimulation in the presence of IL-2, IL-23 and IL-1β. The IL-17RA can be associated with cells or cell membranes, can be native or overexpressed, or can be a fragment of IL-17RA, for example the extracellular domain of the receptor. The IL-17RA can be a human IL-17RA, or IL-17RA from other species such as from mouse, rat or monkey. Antagonists binding to human IL-17A residues V22, V24, L26, I28, Y62, L99, R101, F110, and L112 can be identified by the ability of the antagonist to replace Fab6468 binding to IL-17A, by mutagenesis studies or by co-crystal structures. Fusion proteins of human IL-17A and IL-17RA can be made by well known methods. Exemplary fusion protein is a soluble IL-17RA fused to an immunoglobulin Fc domain.

Another aspect of the invention is an isolated polynucleotide encoding any of the antibody heavy chains or the antibody light chains or fragments thereof of the invention or their complement. Certain exemplary polynucleotides are disclosed herein, however, other polynucleotides which, given the degeneracy of the genetic code or codon preferences in a given expression system, encode the antibody antagonists of the invention are also within the scope of the invention. Exemplary polynuceotides are shown in SEQ ID NOs: 101, 102, 103 and 104.

Exemplary antibody antagonists may be antibodies of the IgG, IgD, IgE, IgA or IgM isotypes. Additionally, such antibody antagonists can be post-translationally modified by processes such as glycosylation, isomerization, deglycosylation or non-naturally occurring covalent modification such as the addition of polyethylene glycol (PEG) moieties (pegylation) and lipidation. Such modifications may occur in vivo or in vitro. For example, the antibodies of the invention can be conjugated to polyethylene glycol (PEGylated) to improve their pharmacokinetic profiles. Conjugation can be carried out by techniques known to those skilled in the art. Conjugation of therapeutic antibodies with PEG has been shown to enhance pharmacodynamics while not interfering with function. See Deckert et al., nt. J. Cancer 87:382-90, 2000; Knight et al., Platelets 15:409-18, 2004; Leong et al., Cytokine 16:106-19, 2001; and Yang et al., Protein Eng. 16:761-70, 2003.

Pharmacokinetic properties of the antibodies of the invention can be enhanced through Fc modifications by techniques known to those skilled in the art. The "Fc" of an antibody is not involved directly in binding of an antibody to an antigen, but exhibits various effector functions. An antibody "Fc" is a term well known and is defined on the basis of papain cleavage of antibodies. The Fc of an antibody is directly involved in ADCC (antibody-dependent cell-mediated cytotoxicity) and CDC (complement-dependent cytotoxicity) based on complement activation, Clq binding and Fc receptor binding. Such complement and Fc receptor binding sites are well known and include for example L234, L235, D270, N297, E318, K320, K322, P331, and P329 (numbering according to EU index of Kabat) (Brekke et al., Eur. J. Immunol. 24:2542-7, 1995; U.S. Pat. Nos. 5,624,821, 7,597,889, Canfield and Morrison, J. Exp. Med. 173:1483-91, 1991). For example, mutation of Leu234/Leu235 in the hinge region of IgG1 to L234A/L235A or Phe235/Leu236 in the hinge region of IgG4 to P235A/L236A minimizes FcR binding and reduces the ability of the immunoglobulin to mediate complement dependent cytotoxicity and ADCC. A Ser to Pro substitution in the Cys-Pro-Ser-Cys (CPSC) motif in the hinge region of IgG4 heavy chains capable of forming either inter- or intra-heavy chain disulfide bonds in vivo via action of isomerases (Aalberse and Schuurman, Immunology 105:9-19, 2002), results in "IgG1-like behavior", i.e., the Pro-substituted molecules are unable to form intra-heavy chain disulfide bonds. The location of the CPSC motif is typically found at residue 228 of a mature heavy chain but can change depending on CDR lengths. An exemplary IgG1 Fc region having the Leu234/Leu235 residues has an amino acid sequence shown in SEQ ID NO: 114, wherein the residues L117 and L118 correspond to the Leu234/Leu235 residues in the mature heavy chain. An exemplary IgG4 Fc region having the Cys-Pro-Ser-Cys (CPSC) motif and the Leu234/Leu235 residues has an amino acid sequence shown in SEQ ID NO: 115, where the CPSC motif is located at residues 106-109 and the Leu234/Leu235 residues at positions 122 and 123.

Antibodies or fragments thereof of the invention modified to improve stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (Worn et al., J. Mol. Biol. 305:989-1010, 2001). Potential structure destabilizing residues may be identified based upon the crystal structure of the antibody or by molecular modeling in certain caases, and the effect of the residues on antibody stability can be tested by generating and evaluating variants harboring mutations in the identified residues. One of the ways to increase antibody stability is to raise the thermal transition midpoint (Tm) as measured by differential scanning calorimetry (DSC). In general, the protein Tm is correlated with its stability and inversely correlated with its susceptibility to unfolding and denaturation in solution and the degradation processes that depend on the tendency of the protein to unfold (Remmele et al., Biopharm. 13:36-46, 2000). A number of studies have found correlation between the ranking of the physical stability of formulations measured as thermal stability by DSC and physical stability measured by other methods (Gupta et al., AAPS PharmSci. 5E8, 2003; Zhang et al., J. Pharm. Sci. 93:3076-89, 2004; Maa et al., Int.

J. Pharm., 140:155-68, 1996; Bedu-Addo et al., Pharm. Res., 21:1353-61, 2004; Remmele et al., Pharm. Res., 15:200-8, 1997). Formulation studies suggest that a Fab Tm has implication for long-term physical stability of a corresponding mAb. Differences in amino acids in either framework or within the CDRs could have significant effects on the thermal stability of the Fab domain (Yasui, et al., FEBS Lett. 353:143-6, 1994).

The antibody antagonists of the invention may bind IL-17A with a $K_d$ less than or equal to about $10^{-7}$, $10^{-8}$, $10^{-9}$, $10^{-10}$, $10^{-11}$ or $10^{-12}$ M. The affinity of a given molecule for IL-17A, such as an antibody can be determined experimentally using any suitable method. Such methods may utilize Biacore or KinExA instrumentation, ELISA or competitive binding assays known to those skilled in the art.

Antibody antagonists binding human IL-17A with a desired affinity can be selected from libraries of variants or fragments by techniques including antibody affinity maturation. Antibody antagonists can be identified based on their inhibition of IL-17A biological activity using any suitable method. Such methods may utilize reporter-gene assays or assays measuring cytokine production using well known methods and as described in the application.

Another embodiment of the invention is a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means.

Another embodiment of the invention is a host cell comprising any of the polynucleotides of the invention such as a polynucleotide encoding a polypeptide comprising an immunoglobulin heavy chain variable region having the amino acid sequence shown in SEQ ID NOs: 67-75 and 81-86 or an immunoglobulin light chain variable region having the amino acid sequence shown in SEQ ID NOs: 62-66 and 76-80 or an an immunoglobulin heavy chain having the amino acid sequence shown in SEQ ID NOs: 92-100 or an immunoglobulin light chain having the amino acid sequence shown in SEQ ID NOs: 87-91. Such host cells may be eukaryotic cells, bacterial cells, plant cells or archeal cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44.

Another embodiment of the invention is a method of making an antibody reactive with IL-17A comprising culturing a host cell of the invention and recovering the antibody produced by the host cell. Methods of making antibodies and purifying them are well known in the art. For expression, the engineered family 2, 6a, 6b, 19a and 19b heavy chain sequences can include an N-terminal leader sequence such as MAWVWTLLFLMAAAQSIQA (SEQ ID NO:109). Exemplary nucleotide sequences encoding the heavy chain of candidate mAb6785 (family 19) with a leader sequence and the mature form (without a leader sequence) are shown in SEQ ID NOs: 101 and 102, respectively. Likewise, for expression, the light chain sequences of the family 2, 6a, 6b antibodies of the invention can include an N-terminal leader sequence such as MGVPTQVLGLLLLWLTDARC (SEQ ID NO: 110)and the light chain sequences of the family 19a and 19b antibodies of the invention can include an N-terminal leader sequence such as MAWSPLLLTLLAHCTGSWA (SEQ ID NO: 116). Exemplary nucleotide sequences encoding the light chain of codon optimized mAb6785 with a leader sequence and the mature form (without a leader sequence) are shown in SEQ ID NOs: 103 and 104, respectively.

Another embodiment of the invention is a hybridoma cell line that produces an antibody of the invention.

Methods of Treatment

IL-17A antagonists of the invention, for example IL-17A antibody antagonists, may be utilized in any therapy where it is desired to reduce the effects of IL-17A in the animal patient. IL-17A may be circulating in the body or may be present in an undesirably high level localised at a particular site in the body, for example a site of inflammation. While not wishing to be bound by any particular theory, the antagonists of the invention provide beneficial therapy by preventing or reducing IL-17A binding to its receptor, or homo- or heterodimerization of IL-17A. The methods of the invention may be used to treat an animal patient belonging to any classification. Examples of such animals include mammals such as humans, rodents, dogs, cats and farm animals.

Antibodies of the invention may be useful for the prophylaxis and treatment of IL-17A mediated conditions, such as inflammatory conditions, allergies and allergic conditions, hypersensitivity reactions, autoimmune diseases, severe infections, and organ or tissue transplant rejection. The antibodies of the invention are also useful in the preparation of a medicament for such treatment, wherein the medicament is prepared for administration in dosages defined herein. Exemplary IL-17A mediated conditions are inflammatory conditions, immune and proliferative disorders, including rheumatoid arthritis (RA), ankylosing spondylitis, psoriatic arthritis, osteoarthritis, osteoporosis, uveitis, inflammatory fibrosis (e.g., scleroderma, lung fibrosis, and cirrhosis), inflammatory bowel disorders (e.g., Crohn's disease, ulcerative colitis and inflammatory bowel disease), asthma (including allergic asthma), allergies, COPD, multiple sclerosis, psoriasis, systemic lupus erythematosus, diabetes and cancer. Positive outcomes in patients treated with anti-human IL-17A therapies have been described in rheumatoid arthritis, psoriasis and non-infectious uveitis (Genovese et al., Arthritis Rheum. 62:929-39, 2010; Hueber et al., Sci. Transl. Med. 2: 52ra72., 2010).

Inflammatory pulmonary condition is an example of an inflammatory condition. Exemplary inflammatory pulmonary conditions include infection-induced pulmonary conditions including those associated with viral, bacterial, fungal, parasite or prion infections; allergen-induced pulmonary conditions; pollutant-induced pulmonary conditions such as asbestosis, silicosis, or berylliosis; gastric aspiration-induced pulmonary conditions, immune dysregulation, inflammatory conditions with genetic predisposition such as as cystic fibrosis, and physical trauma-induced pulmonary conditions, such as ventilator injury. These inflammatory conditions also include asthma, emphysema, bronchitis, chronic obstructive pulmonary disease (COPD), sarcoidosis, histiocytosis, lymphangiomyomatosis, acute lung injury, acute respiratory distress syndrome, chronic lung disease, bronchopulmonary dysplasia, community-acquired pneumonia, nosocomial pneumonia, ventilator-associated pneumonia, sepsis, viral pneumonia, influenza infection, parainfluenza infection, rotavirus infection, human metapneumovirus infection, respiratory syncitial virus infection and aspergillus or other fungal infections. Exemplary infection-associated inflammatory diseases may include viral or bacterial pneumonia, including severe pneumonia, cystic fibrosis, bronchitis, airway exacerbations and acute respiratory distress syndrome (ARDS). Such infection-associated conditions may involve multiple infections such as a primary viral infection and a secondary bacterial infection. Dysregulated IL-17A production may play a role in the pathology of pulmonary diseases such as asthma and Chronic Obstructive Pulmonary Disease (COPD) (reviewed in Alcorn et al., Annu. Rev. Physiol. 72:495-516, 2010). IL-17A has been shown to regulate neutrophilic inflammation in the lungs—a hallmark of severe asthma as well as COPD—owing to the capacity of IL-17A to induce factors important in neutrophil recruitment, survival and activation from lung resident epithelial cells (e.g, IL-6, IL-8, GM-CSF, G-CSF). The antibodies a of the present invention suppress IL-6, IL-8, and GM-CSF secretion from lung epithelial cells, and thus may be beneficial in the therapeutic or prophylactic treatment of subjects with pulmonary inflammatory conditions, such as asthma and COPD. Commonly used animal models for asthma and airway inflammation include the ovalbumin challenge model and methacholine sensitization models (Hessel et al., Eur. J. Pharmacol. 293:401-12, 1995). Inhibition of cytokine and chemokine production from cultured human bronchial epithelial cells, bronchial fibroblasts or airway smooth muscle cells can also be used as in vitro models. The administration of antagonists of the present invention to any of these models can be used to evaluate the use of those antagonists to ameliorate symptoms and alter the course of asthma, airway inflammation, COPD and the like.

Psoriasis is another example of an inflammatory condition. Psoriasis is characterized by T cell mediated hyperproliferation of keratinocytes coupled with an inflammatory infiltrate. The inflammation and hyperproliferation of psoriatic tissue is associated with a different histological, antigenic, and cytokine profile than normal skin. Among the cytokines associated with psoriasis are: TNFα, IL-19, IL-18, IL-15, IL-12, IL-7, IFNγ, IL-17A and IL-23 (Gudjonsson et al., Clin. Exp. Immunol. 135:1-8, 2004). IL-17A has been found overexpressed in psoriatic lesions (U.S. Pat. No. 7,776,540) and positive outcomes in patients treated with anti-human IL-17A therapies have been described (Hueber et al., Sci. Transl. Med. 2: 52ra72., 2010).

Arthritis, including osteoarthritis, rheumatoid arthritis, arthritic joints as a result of injury, and the like, are common inflammatory conditions, which would benefit from the therapeutic use of anti-inflammatory proteins, such as the antagonists of the present invention. Activation of IL-17A signaling may perpetuate inflammation and further tissue damage in the inflamed joint. Several animal models for rheumatoid arthritis are known. For example, in the collagen-induced arthritis (CIA) model, mice develop chronic inflammatory arthritis that closely resembles human rheumatoid arthritis. Administration of the IL-17A antibodies of the present invention to the CIA model mice can be used to evaluate the use of these antagonists to ameliorate symptoms and alter the course of diseases.

Exemplary gastrointestinal inflammatory conditions are inflammatory bowel disease (IBD), ulcerative colitis (UC) and Crohn's disease (CD), colitis induced by environmental insults (e.g., gastrointestinal inflammation (e.g., colitis) caused by or associated with (e.g., as a side effect) a therapeutic regimen, such as administration of chemotherapy, radiation therapy, and the like), infections colitis, ischemic colitis, collagenous or lymphocytic colitis, necrotizing enterocolitis, colitis in conditions such as chronic granulomatous disease or celiac disease, food allergies, gastritis, infectious gastritis or enterocolitis (e.g., Helicobacter pylori-infected chronic active gastritis) and other forms of gastrointestinal inflammation caused by an infectious agent. Several animal models for gastrointestinal inflammatory conditions exist. Some of the most widely used models are the 2,4,6-trinitrobenesulfonic acid/ethanol (TNBS)-induced colitis model or the oxazalone model, which induce chronic inflammation and ulceration in the colon (Neurath et al., Intern. Rev. Immunol 19:51-62, 2000). Another model uses dextran sulfate sodium (DSS), which induces an acute colitis manifested by bloody diarrhea, weight loss, shortening of the colon and mucosal ulceration with neutrophil infiltration. Another model involves the adoptive transfer of naive CD45RB$^{high}$ CD4 T cells to RAG or SCID mice. In this model, donor naive T cells attack the recipient gut causing chronic bowel inflammation and symptoms similar to human inflammatory bowel diseases (Read and Powrie, Curr. Protoc. Immunol. Chapter 15 unit 15.13, 2001). The administration of antagonists of the present invention in any of these models can be used to evaluate the potential efficacy of those antagonists to ameliorate symptoms and alter the course of diseases associated with inflammation in the gut, such as inflammatory bowel disease.

Renal fibrosis can develop from either an acute insult (ex. graft ischemia/reperfusion) (Freese et al., Nephrol. Dial. Transplant. 16:2401-6, 2001) or chronic condition (for example diabetes) (Ritz et al., Nephrol. Dial. Transplant. 11 Suppl 9:38-44, 1996). The pathogenesis is typically characterized by an initial inflammatory response followed by sustained fibrogenesis of the glomerular filtration apparatus and tubular interstitium (Liu, Kidney Int. 69:213-7, 2006). Tubulointerstitial fibrosis has been shown to play a critical role in the pathogenesis of renal injury to end-stage renal failure and the proximal tubule cell has been revealed as a central mediator (Phillips and Steadman, Histol. Histopathol. 17:247-52, 2002; Phillips, Chang Gung Med. J. 30:2-6, 2007). Fibrogenesis in the tubulointerstitial compartment is mediated in part by activation of resident fibroblasts, which secrete pro-inflammatory cytokines that stimulate the proximal tubule epithelium to secrete local inflammatory and fibrogenic mediators. Additionally, chemotactic cytokines are secreted by fibroblasts and epithelial cells and provide a directional gradient guiding the infiltration of monocytes/macrophages and T-cells into the tubulointerstitium. The inflammatory infiltrate produces additional fibrogenic and inflammatory cytokines that further activate fibroblast and epithelial cytokine release while also stimulating the epithelium to undergo a phenotypic transition in which the cells deposit excess extracellular matrix components (Simonson, Kidney Int. 71:846-54, 2007). IL-17A has been shown to be upregulated during human renal allograft rejection (Van Kooten et al., J. Am. Soc. Nephrol. 9:1526-34, 1998; Loong et al., J. Path. 197:322-32, 2002). IL-17A stimulates the production of the pro-inflammatory mediators IL-6, IL-8, complement component C3, and RANTES by proximal tubular epithelium (Van Kooten et al., J. Am. Soc. Nephrol. 9:1526-34, 1998; Woltman et al., J. Am. Nephrol. 11:2044-55, 2000). These factors, in turn, mediate the recruitment of other inflammatory cell-types into the interstitium that contribute to the maintenance of the inflammatory/immune response and, if not suppressed, the onset of fibrosis and chronic allograft nephropathy (Racusen et al., Kidney Int. 55:713-23, 1999; Mannon, Am. J. Transpl. 6:867-75, 2006).

Other exmplary fibrotic conditions may include liver fibrosis (including but not limited to alcohol-induced cirrhosis, viral-induced cirrhosis, autoimmune-induced hepatitis); lung fibrosis (including but not limited to scleroderma, idiopathic pulmonary fibrosis); kidney fibrosis (including but not limited to scleroderma, diabetic nephritis, glomerular nehpritis, lupus nephritis); dermal fibrosis (including but not limited to scleroderma, hypertrophic and keloid scarring, burns); myelofibrosis; neurofibromatosis; fibroma; intestinal fibrosis; and fibrotic adhesions resulting from surgical procedures. The fibrosis can be organ specific fibrosis or systemic fibrosis. The organ specific fibrosis can be associated with lung fibrosis, liver fibrosis, kidney fibrosis, heart fibrosis, vascular fibrosis, skin fibrosis, eye fibrosis or bone marrow fibrosis. The lung fibrosis can be associated with idiopathic pulmonary fibrosis, drug induced pulmonary fibrosis, asthma, sarcoidosis or chronic obstructive pulmonary disease. The liver fibrosis can be associated with cirrhosis, schistomasomiasis or cholangitis. The cirrhosis can be selected from alcoholic cirrhosis, post-hepatitis C cirrhosis, primary biliary cirrhosis. The cholangitis can be sclerosing cholangitis. The kidney fibrosis can be associated with diabetic nephropathy or lupus glomeruloschelerosis. The heart fibrosis can be associated with myocardial infarction. The vascular fibrosis can be associated with postangioplasty arterial restenosis or atherosclerosis. The skin fibrosis can be associated with burn scarring, hypertrophic scarring, keloid, or nephrogenic fibrosing dermatopathy. The eye fibrosis can be associated with retroorbital fibrosis, postcataract surgery or proliferative vitreoretinopathy. The bone marrow fibrosis can be associated with idiopathic myelofibrosis or drug induced myelofibrosis. The systemic fibrosis can be systemic sclerosis or graft versus host disease.

Other inflammatory conditions and neuropathies, which may be prevented or treated by the methods of the invention are those caused by autoimmune diseases. These conditions and neuropathies include multiple sclerosis, systemic lupus erythematous, and neurodegenerative and central nervous system (CNS) disorders including Alzheimer's disease, Parkinson's disease, Huntington's disease, bipolar disorder and Amyotrophic Lateral Sclerosis (ALS), liver diseases including primary biliary cirrhosis, primary sclerosing cholangitis, non-alcoholic fatty liver disease/steatohepatitis, fibrosis, hepatitis C virus (HCV) and hepatitis B virus (HBV), diabetes and insulin resistance, cardiovascular disorders including atherosclerosis, cerebral hemorrhage, stroke and myocardial infarction, arthritis, rheumatoid arthritis, psoriatic arthritis and juvenile rheumatoid arthritis (JRA), osteoporosis, osteoarthritis, pancreatitis, fibrosis, encephalitis, psoriasis, Giant cell arteritis, ankylosing spondolytis, autoimmune hepatitis, human immunodeficiency virus (HIV), inflammatory skin conditions, transplant, cancer, allergies, endocrine diseases, wound repair, other autoimmune disorders, airway hyperresponsiveness and cell, virus, or prion-mediated infections or disorders.

Administration/Pharmaceutical Compositions

The "therapeutically effective amount" of the agent effective in the treatment of conditions where suppression of IL-17A activity is desirable can be determined by standard research techniques. For example, the dosage of the agent that will be effective in the treatment of an inflammatory condition such as asthma, Crohn's Disease, ulcerative colitis or rheumatoid arthritis can be determined by administering the agent to relevant animal models, such as the models described herein.

In addition, in vitro assays can optionally be employed to help identify optimal dosage ranges. Selection of a particular effective dose can be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

The mode of administration for therapeutic use of the agent of the invention may be any suitable route that delivers the agent to the host. Pharmaceutical compositions of these agents are particularly useful for parenteral administration, e.g., intradermal, intramuscular, intraperitoneal, intravenous, subcutaneous or intranasal.

The agent of the invention may be prepared as pharmaceutical compositions containing an effective amount of the agent as an active ingredient in a pharmaceutically acceptable carrier. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the agent of the invention in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected.

Thus, a pharmaceutical composition of the invention for intramuscular injection could be prepared to contain 1 ml sterile buffered water, and between about 1 ng to about 100 mg, e.g. about 50 ng to about 30 mg or more preferably, about 5 mg to about 25 mg, of a IL-17A antibody antagonist of the invention. Similarly, a pharmaceutical composition of the invention for intravenous infusion could be made up to contain about 250 ml of sterile Ringer's solution, and about 1 mg to about 30 mg and preferably 5 mg to about 25 mg of an antagonist of the invention. Actual methods for preparing parenterally administrable compositions are well known and are described in more detail in, for example, "Remington's Pharmaceutical Science", 15th ed., Mack Publishing Company, Easton, Pa.

The antibody antagonists of the invention can be lyophilized for storage and reconstituted in a suitable carrier prior to use. This technique has been shown to be effective with conventional immunoglobulins and protein preparations and art-known lyophilization and reconstitution techniques can be employed.

The present invention will now be described with reference to the following specific, non-limiting examples.

EXAMPLE 1

Identification of Anti-human IL-17A Antagonistic mAbs

The MorphoSys Human Combinatorial Antibody Library (HuCAL®) Gold phage display library (Morphosys AG, Martinsried, Germany) was used as a source of human antibody fragments and was panned in subpools in solution. In the first round of panning, the sublibraries were selected against biotinylated mature His6-tagged IL-17A A132Q and A70Q variant (IL-17Amut6) (SEQ ID NO: 106). In the second round, the amplified output of round 1 was selected against biotinylated His6-tagged IL-17Amut6 in the presence or absence of other IL-17A family members as a competitor to bias against antibodies that were specific to IL-17A. The amplified output of round 2 was divided in two pools. The first pool was panned as in round 1. The clones in the second pool were further diversified in either HCDR2 or LCDR3, depending on the sublibrary used in the initial selections, and then carried through 2 additional rounds of panning against IL-17Amut6 to give a second source of clones for screening. Fabs from clone lysates were captured in ELISA plate wells coated with sheep anti-human Fd antibody and screened for binding to biotinylated IL-17Amut6. Crude lysates of positive clones were screened for inhibition of IL-17Amut6 binding to recombinant human IL-17RA receptor (SEQ ID NO: 107).

Select clones were chosen for further characterization as purified Fabs based on sequence scoring, affinity, and representation of all sequence families, and were designated with MOR numbers. Additional variants for MOR7708, MOR7785, MOR7706, MOR7775 and MOR7700 were generated to replace Trp or Met residing in HCDR2, HCDR3, or LCDR3. Table 3 shows the generated variants.

TABLE 3

| Family | Parent MOR# | Variant MOR# | HCDR2 | HCDR3 | LCDR3 |
|---|---|---|---|---|---|
| 2 | MOR7708 | MOR8297 | W57T | | |
| | | MOR8298 | W57Y | | |
| | MOR7785 | MOR8104 | W57T | | |
| | | MOR8105 | W57Y | | |
| 6b | MOR7706 | MOR8299 | | M106I | |
| | | MOR8300 | | M106L | |
| | | MOR8301 | | M106T | |
| | MOR7775 | MOR8101 | | M106I | |
| | | MOR8102 | | M106L | |
| | | MOR8103 | | M106T | |
| 19a | MOR7700 | MOR8095 | M53I | | |
| | | MOR8096 | M53L | | |
| | | MOR8097 | | M101L | |
| | | MOR8098 | | M101T | |
| | | MOR8141 | | | M96L |
| | | MOR8142 | | | M96T |
| | | MOR8143 | | | M96Y |
| | | MOR8160 | | M101T | M96L |
| | | MOR8161 | | M101T | M96T |
| | | MOR8162 | | M101T | M96Y |
| | | MOR8302 | M53L | M101T | |
| | | MOR8303 | M53L | M101T | M96T |

The Fabs were tested for their inhibition of IL-17Amut6 and cynoIL-17A binding to recombinant human IL-17RA receptor, and their binding to IL-17Amut6. All tested Fabs inhibited both IL-17Amut6 and cynoIL-17A binding to the IL-17RA. Affinity of the Fabs to IL-17Amut6 was measured using the SET assay (Table 4). From the identified Fabs, candidates from families 2, 6a, 6b, 19a and 19b were selected for further characterization.

TABLE 4

| Family | MOR# | Kd (SET) (pM) |
|---|---|---|
| 2 | 7702 | 11 |
| | 7701 | 45 |
| | 7708 | 90 |
| | 7785 | 6 |
| | 8104 | 150 |
| | 8105 | 130 |
| | 7786 | 20 |
| 6b | 7706 | 90 |
| | 7775 | 44 |
| | 8101 | 150 |
| | 8102 | 130 |
| | 8103 | 89 |
| 19a | 7700 | 30 |
| | 8095 | 77 |
| | 8096 | 28 |
| | 8097 | 69 |
| | 8098 | 47 |
| | 8141 | 30 |
| | 8142 | 90 |
| | 8143 | 130 |
| | 8160 | 70 |

EXAMPLE 2

Derivation, Engineering and Characterization of Anti-IL-17A Antagonistic mAbs

The selected MOR# Fabs were converted and expressed as mAbs in a human IgG1 format, and given corresponding MORmAb designation. The generated MORmAbs were tested for expression and aggregation, their ability to inhibit human and cyno IL-17A binding to human IL-17RA, and IL-8 secretion from NHDF cells. Table 5 shows IC50 values for select assays for the MORmAbs. None of the tested MORmAbs (MORmAb#s 7702, 7708, 7785, 7786, 7706, 7775, 7700, 8095, 8096, 8097, 8098, 7768) cross-reacted with other IL-17 family members.

TABLE 5

| | | Human IL-17, IC50 (pM) | | Cyno IL-17, |
|---|---|---|---|---|
| Family | MORmAb# | IL-17RA Inhibition | IL-8 secretion | IC50 (pM) IL-17RA Inhibition |
| 2 | 7702 | 297 | 6214 | 209 |
| | 7708 | 284 | 398 | 289 |
| | 7785 | 172 | 196 | 270 |
| | 8104 | 204 | 512 | 306 |
| | 8105 | 538 | 1168 | 498 |
| | 7786 | 140 | 368 | 59 |
| 6b | 7706 | 378 | 402 | 961 |
| | 7775 | 138 | 2244 | 541 |
| | 8101 | 108 | 1907 | 845 |
| | 8102 | 186 | 24520 | 838 |
| | 8103 | 167 | 929 | 491 |
| 19a | 7700 | 99 | 70 | 236 |
| | 8095 | 130 | 121 | 198 |
| | 8096 | 189 | 75 | 58 |
| | 8097 | 178 | 84 | 300 |
| | 8098 | 225 | 146 | 289 |
| | 8141 | 117 | 67 | 1435 |
| | 8142 | 129 | 79 | 139 |
| | 8143 | 191 | 61 | 252 |
| | 7768 | 456 | 229 | 388 |

Framework Engineering of Anti-IL-17A Antagonistic mAbs

Based on activity and biophysical and biochemical properties, select MORmAbs were further engineered in their variable regions to change certain framework residues to those present in a matching human germline and to change codons to those most frequently occurring in highly expressed mammalian proteins. In family 2 VL, L111V and V85T (linear sequence) substitutions were made, converting the framework to an exact match with the VK-1 germline Vb-L5 (IGKV1-12*01). An exemplary variable region with the V11V and V85T substitutions is the variable region having the amino acid sequence shown in SEQ ID NO: 76. In family 6a and 6b VL, D1E, V59I and T86V substitutions were made (linear sequence), converting the framework to exact match with the Vk-3 germline Vb-L6 (IGKV3-11*01). An exemplary variable region with the D1E, V59I and T86V substitutions is the variable region having the amino acid sequence shown in SEQ ID NO: 77. In family 6a and 6b VH, a G44S substitution was made (linear sequence) to match the Vh-6 germline Vb 6-01 (IGHV6-1*01). An exemplary variable region with the G44S substitution is the variable region having the amino acid sequence shown in SEQ ID NO: 81. In family 19a and 19b VL, amino acids 1-3 (DIE) were substituted with QSV to replace the artificial kappa N-terminus with that of a lambda chain. Exemplary variable region with the QSV substitution is a variable region having the amino acid sequence shown in SEQ ID NO: 79. In family 19a and 19b VH, a V5L substitution was made to give a close match the Vh-3 germline Vb 3-23 (IGHV3-23*01. Also, in this process the heavy chain constant region amino acid sequence residues 353-357 (REEMT) were substituted with RDELT. An exemplary variable region with the V5L substitution is a variable region having the amino acid sequence shown in SEQ ID NO: 86. An exemplary heavy chain with the constant region 353-357 REEMT->RDELT substitutions is a heavy chain having the amino acid sequence shown in SEQ ID NO: 100. The engineered antibodies were given mAb numbers.

The corresponding designations and the sequence listings of the engineered and original variable regions and full length antibodies are listed in Table 2. The sequences of the CDRs within each family are shown in FIG. 1.

The engineered mAbs were characterized as described above for the MORmAbs. The IC50 values (pM) measured using indicated assays are shown in Table 6.

TABLE 6

| Family | mAb# | IC50 (pM), human IL-17A | | | IC50 (pM), cynoIL-17A | | |
|---|---|---|---|---|---|---|---|
| | | IL-17RA inhi-bition | IL-8 pro-duction | IL-6 pro-duction | IL-17RA inhi-bition | IL-8 pro-duction | IL-6 pro-duction |
| 2 | mAb624 | 78 | 687 | 234 | 51 | 192 | 687 |
| | mAb3077 | 118 | 292 | 37 | 54 | 374 | 113 |
| | mAb7024 | 185 | 693 | 412 | 117 | 2979 | 999 |
| 6b | mAb4538 | 229 | 1483 | 264 | 636 | 1754 | 847 |
| | mAb3584 | 195 | 2388 | 370 | 489 | 1253 | 823 |
| | mAb732 | 327 | 2607 | 560 | 463 | 12527 | 2017 |
| | mAb4168 | 266 | 4878 | 732 | 764 | 3301 | 2172 |
| 19a | mAb1926 | 108 | 62 | 35 | 53 | 105 | 67 |
| | mAb7146 | 143 | 71 | 40 | 67 | 140 | 139 |
| | mAb6785 | 172 | 95 | 45 | 76 | 563 | 193 |

Affinity of select mAbs was assessed using Biacore. The results of the measurements are shown in Table 7.

TABLE 7

| Antibody | $k_a$ ($M^{-1}s^{-1}$) | $k_d$ ($s^{-1}$) | $K_D$ (pM) | Stoichiometry * |
|---|---|---|---|---|
| Binding to human IL-17Amut6 | | | | |
| mAb7146 | $4.67 \times 10^6$ | $5.57 \times 10^{-5}$ | 12 | 2.1 |
| mAb6785 | $3.80 \times 10^6$ | $6.98 \times 10^{-5}$ | 18 | 2.1 |
| Fab6486 | $3.14 \times 10^6$ | $1.23 \times 10^{-4}$ | 39 | 1.1 |
| mAb5548 | $3.63 \times 10^6$ | $1.45 \times 10^{-4}$ | 40 | 2.1 |
| mAb1926 | $4.43 \times 10^6$ | $3.41 \times 10^{-5}$ | 8 | 2.1 |
| Binding to cyno IL-17A | | | | |
| mAb7146 | $2.23 \times 10^6$ | $1.12 \times 10^{-4}$ | 50 | 2 |
| mAb6785 | $1.80 \times 10^6$ | $2.67 \times 10^{-4}$ | 148 | 2.2 |
| Fab6486 | $1.60 \times 10^6$ | $3.28 \times 10^{-4}$ | 205 | 1.1 |
| mAb5548 | $1.61 \times 10^6$ | $3.62 \times 10^{-4}$ | 225 | 1.9 |
| mAb1926 | $2.77 \times 10^6$ | $5.11 \times 10^{-5}$ | 18 | 2.3 |

* dimers per anti-IL-17

Anti-IL-17 Antibody Inhibits Cytokine Secretion in NHBE Cells

IL-17A has been shown to regulate neutrophilic inflammation in the lungs, a hallmark of severe asthma as well as COPD, owing to the capacity of IL-17A to induce factors important in neutrophil recruitment, survival and activation (e.g, IL-6, IL-8, GM-CSF). To determine whether anti-IL-17A antibodies of the invention can inhibit IL-17A-induced changes in lung resident cells, normal human bronchial epithelial (NHBE) cells were stimulated with human IL-17A for 48 hours in the presence of mAb6785. mAb6785 inhibited IL-17A-induced IL-6 and GM-CSF production by NHBE cells with IC50=619.0±64.0 pM and 564±86 pM, respectively.

Anti-IL-17 Antibody Inhibits the Biological Activity of IL-17A/F Heterodimer

Normal Human Dermal Fibroblasts (NHDF; Lonza) cells were seeded into a 48-well flat bottom tissue culture plate at 10,000 cells per well in FGM-$_2$ medium (Lonza) and incubated overnight (37°, 5% CO$_2$). Following incubation, 50 ng/mL final concentration (1.47 nM) of rhIL-17A/F heterodimer (R&D Systems) was pre-incubated with a dilution series (30 µg/mL-0.5 ng/mL) of mAb6785 or control antibodies for 10 minutes at room temperature, and added to cells. Cells were incubated for 48 h (37°, 5% CO$_2$) and culture supernatants were collected and assayed by ELISA for IL-6 content using Human IL-6 Duo Sets (R&D Systems, Inc.) according to manufacturer's instructions. IC50 values were determined by non-linear regression using GraphPad Prism software (GraphPad Software, Inc). mAb6785 inhibited IL-17A/F heterodimer-induced IL-6 production by NHDF with EC50 2±2.5 nM.

Methods

Determination of Picomolar Affinities Using Solution Equilibrium Titration (SET)

For $K_D$ determination by solution equilibrium titration (SET), monomer fractions (at least 90% monomer content, analyzed by analytical SEC; Superdex75 column, GE) of Fab protein were used.

Electrochemiluminescence (ECL) based affinity determination in solution and data evaluation were basically performed as described previously (Haenel et al., Anal Biochem 339:182-4, 2005). A defined fixed concentration of purified Fab (~10-100 pM) was incubated with increasing concentrations of IL-17Amut6 (highest concentration of 5 nM) in solution until chemical equilibrium was achieved. To quantify the unbound Fab in solution the samples were transferred to a Streptavidin MSD 384-well microtiter plate (Meso Scale Discovery, Gaithersburg, Md.) with coated biotinylated IL-17Amut6. For detection, a ruthenium complex-labeled anti-human Fab/IgG antibody was applied and the plates were read with the Sector™ Imager 6000 (MSD). Titration curves (concentration of free Fab as a function of antigen concentration) were plotted and fitted with Excel/XLfit software using the model described below.

For data evaluation for $K_D$ determination of Fab molecules, the following fit model was used (modified according to Abraham et al. J Mol Recognit. 9:456-461, 1996):

$$y = B\max - (B\max/(2*cFab)*(x+cFab+KD-\operatorname{sqrt}((x+cFab+KD)*(x+cFab+KD)-4*x*cFab)))$$

Whereas:
Bmax: maximum binding signal (at antigen concentration=0)
cFab: applied Fab concentration
x: applied total soluble antigen concentration (binding sites)
sqrt: square root
$K_D$: Equilibrium dissociation constant
Inhibition of IL-17A Binding to IL-17RA (e.g. "IL-17RA Inhibition" Assay Clear maxisorp plates were coated with 100 μl/well of 2.5 μg/ml human IL-17RA-Fc (R&D Systems, Minneapolis, Minn.) in 0.1 M sodium carbonate-bicarbonate buffer, pH 9.4 and incubated overnight at 4° C. After blocking and washes, 25 ng/ml of biotinylated human IL-17mut6 (SEQ ID NO: 106) or cynomolgus IL-17A (SEQ ID NO: 108) was pre-incubated with tested mAbs or control mAbs (30 to 0 μg/ml final concentration) in a combined volume of 100 μl for 5-10 minutes, and then added to plates. The signal was detected with 100 μl of 1:10,000 dilution of 1 mg/ml SA-HRP (Jackson Immunoresearch, West Grove, Pa.) for 20 minutes at room temperature (RT) followed by 100 μl/well of OPD substrate (Sigma-Aldrich Corp., St. Louis, Mo.). The plates were read at 492 nm (Envision, PerkinElmer, Waltham, Mass.). Fab binding to IL-17RA was tested as described for mAbs.
Inhibition of IL-8 and IL-6 Production from NHDF Cells (e.g. "IL-8 Production" and "IL-6 Production" Assays)

Effect of inhibition of anti-IL-17A mAbs on IL-8 and IL-6 production was assessed in normal human dermal fibroblasts (NHDF). Cells were plated in a 48-well flat bottom tissue culture plate at $0.1 \times 10^5$ cells per well, 250 μl per well in FGM-2 medium and incubated overnight (37°, 5% $CO_2$). Following incubation, 0.1 ng/ml human TNF-α was added to all wells. 10 ng/ml IL-17mut6 or 25 ng/ml cynomolgus IL-17A was pre-incubated with tested mAbs or control mAbs (30-0 μg/ml final concentration) in a combined volume of 250 μl for 10 minutes at RT, and then added to 250 μl of cells. In the assays, IL-17mut6 samples with no added antibody were included as control samples, while samples consisting of TNF-α or culture medium only were included as negative controls. Cells were incubated for 24 hours (37°, 5% $CO_2$) and conditioned media were collected and assayed by ELISA for IL-6 and IL-8 using human IL-6 & IL-8 ELISA Duo Sets according to the manufacturer's instructions (R&D Systems, Minneapolis, Minn.). The Fabs were assayed as described fro the mAbs.
Inhibition of IL-6 and G-CSF Production from NHBE Cells Normal human bronchial epithelial (NHBE; Lonza) cells were seeded at 20,000 cells per well in BEGM media (Lonza) and incubated overnight (37°, 5% $CO_2$). Following incubation, cells were stimulated with IL-17Amut6 for 48 hours in the presence of the tested antibodies at a range of concentrations (30 μg/mL-0.5 ng.mL). Supernatants were collected after the incubation and assayed for IL-6 or G-CSF content using a human IL-6- or G-CSF-specific ELISA (R&D Systems, Inc.). IC50 values were determined by non-linear regression using GraphPad Prism software (GraphPad Software, Inc).
Cross-reactivity with IL-17A Family Members Clear maxisorp plates were coated with 100 μl/well of 5 mg/ml mAbs or isotype control mAbs in PBS, and incubated overnight at 4° C. The plates were blocked with 200 μl/well for 1 hour with ELISA block buffer (1% BSA, 5% Sucrose in PBS with 0.05% $NaN_3$) and washed three times with wash buffer (PBS, 0.01% Tween-20). Competing cytokines were titrated in Assay Diluent Buffer (1% BSA in PBS) at 2× final concentration, and biotinylated cytokine was prepared at 2× final concentration. 100 μl of cytokines at 2× final concentration were mixed (30-0 μg/ml final concentration) with 100 μl of biotinylated IL-17mut6 at 2× final concentration (25 ng/ml final concentration) in assay buffer. Recombinant human IL-23 (R&D Systems, Minneapolis, Minn.) was used as a negative control, buffer only sample as background control, and IL-17mut6 as positive control. 100 μl per well in duplicate of cytokine/biotinylated IL-17mut6 mixture was added to the plate and incubated for 1-2 hours. Plates were washed three times with wash buffer, and incubated with 100 μl of 1:10,000 dilution of 1 mg/ml SA-HRP (Jackson Immunoresearch, West Grove, Pa.) for 20 minutes at RT. Plates were washed three times with ELISA wash buffer. Following wash, 100 μl/well of OPD substrate (Sigma-Aldrich Corp., St. Louis, Mo.) was added to each well and incubated until the appropriate color change was detected. The reaction was stopped with the addition of 50 μl of 2N sulfuric acid, and the plates were read 492 nm using the Envision instrument.
Affinity Measurements—Biacore Assay Affinity measurements using Surface Plasmon Resonance (SPR) were performed using a Biacore 3000 optical biosensor (Biacore). Selected Fabs (~30 RU) or mAbs (~50 RU) were captured onto the sensor chip surface using a sheep anti-Fd antibody or an anti-human Fc antibody for Fab or mAb capture, respectively. Capture of Fab or mAb was followed by injection of huIL-17mut6 or cyno IL-17A in solution (0.2 to 49 nM).

EXAMPLE 4

Epitope Mapping

Antibody epitopes were deduced by a combination of competition binding, H/D exchange analysis, and antibody-IL-17A co-structure (see Example 5). The following antibodies were used: mAb1926, MORmAb7700, MORmAb7706, MORmAb7708, mAb7357 (a mouse anti-human IL-17A neutralizing antibody derived from hybridoma C1863), mAb2832 (a mouse/human chimeric anti-human IL-17A neutralizing antibody derived from hybridoma C1861), mAb317 (mouse anti-human IL-17A antibody, R&D Systems, Minneapolis, Minn.) and mAb3171 (mouse anti-human IL-17A antibody, R&D Systems, Minneapolis, Minn.), and mAbeBIO16-7178 (a mouse anti-human IL-17A antibody, e-Bioscience, San Diego, Calif.). The three commercial antibodies showed varying degrees of neutralizing activity.
Competitive Epitope Binding For competitive ELISA, 5 μl (20 μg/ml) of IL-17Amut6 protein was coated on MSD HighBind plate (Meso Scale Discovery, Gaithersburg, Md.) per well for 2 hr at room temperature. 150 μl of 5% MSD Blocker A buffer (Meso Scale Discovery, Gaithersburg, Md.) was added to each well and incubated for 2 hr at room temperature. Plates were washed with 0.1 M HEPES buffer (pH 7.4). Labeled antibody (MDS fluorescence dye), 10 nM, was incubated with increasing concentrations of competitor antibodies (1 nM-2 µM), and 25 µl of the mixture was added to the designated wells. After 2-hour incubation with gentle shaking at RT, plates were washed as above, 150 µl diluted MSD Read Buffer T was added, and the plates were read with a MDS Sector Imager 6000.

Assays were carried out with labeled mAb1926, mAb317, mAb3171, or mAb7357 (FIG. 4). Based on competition assays, anti-IL-17A antibodies were assigned to four different bins. Bin A: mAb1926, MORmAb7706, and MORmAb7708; Bin B: eBio16-7178 and mAb7357; Bin C: mAb317; Bin D: mAb3171.

Figure 5A:
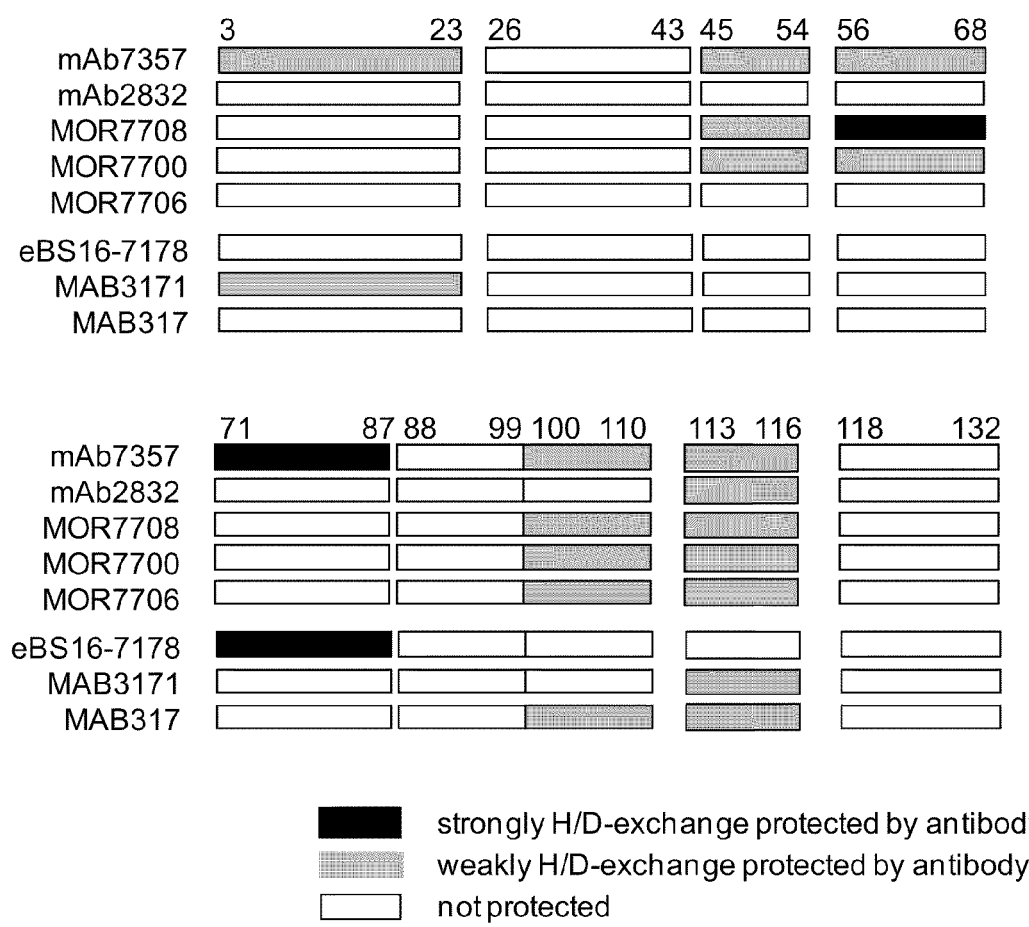
FIG. 5. A) H/D exchange maps of the IL-17A complexed with different anti-IL-17A mAbs. Numbering above the protective blocks corresponds to mature IL-17A (SEQ ID NO: 105) sequence numbering.

H/D Exchange Analysis:

For H/D exchange, the procedure used to analyze the antibody perturbation was similar to that described previously (Hamuro et al., J. Biomol. Techniques, 14:171-82, 2003; Horn et al., Biochemistry, 45: 8488-98, 2006) with some modification. Recombinant IL-17Amut6 (expressed in HEK293E cells with C-terminal His-tag) was incubated in a deuterated water solution for pre-determined times resulting in deuterium incorporation at exchangeable hydrogen atoms. The deuterated IL-17Amut6 was captured on a column containing immobilized individual anti-IL-17A mAbs and then washed with aqueous buffer. The back-exchanged IL-17Amut6 protein was eluted from the column and localization of deuterium containing fragments was determined by protease digestion and mass spec analysis. Regions bound to the antibody were inferred to be those sites relatively protected from exchange and thus containing a higher fraction of deuterium, compared to IL-17Amut6 not complexed with antibody. H/D exchange perturbation maps of IL-17Amut6 are shown in FIG. 5. The numbers on top of the bars refer to IL-17Amut6 resiudes.

MORmAb7700, MORmAb7706 and MORmAb7708 showed varying degrees of differential exchange for three segments of IL-17A (SEQ ID NO: 105) $_{45}$NRSTSPWNLH$_{54}$ (SEQ ID NO: 159), $_{56}$NEDPERYPSVIWE$_{68}$ (SEQ ID NO: 157) and $_{100}$RREPPHCPNSFRLEKIL$_{116}$ (SEQ ID NO: 158), indicating protection by the antibodies. The $_{56}$NEDPERYPSVIWE$_{68}$ (SEQ ID NO: 157) fragment was strongly protected by MORmAb7708, weakly protected by MORmAb7700, and not protected by MORmAb7706. The overlap in the fragment protection patterns of these antibodies is consistent with their cross-inhibition in the competition assays described above.

For both mAb7357 and mAbeBio16-7178, strong protection was observed for $_{71}$CRHLGCINADGNVDYHM$_{87}$ (SEQ ID NO: 160) consistent with their cross-inhibition in the competition assays described above. Weak, and therefore inconclusive, differential exchange was observed for other fragments with mAb7357, mAb2832, mAb317 and mAb3171.

The H/D exchange studies localized the binding sites for two of the four competition groups defined above. Bin A antibodies (MORmAb7700, MORmAb7706 and MORmAb7708) bound in the region of peptide segments $_{45}$NRSTSPWNLH$_{54}$, (SEQ ID NO: 159), $_{56}$NEDPERYPSVIWE$_{68}$ (SEQ ID NO: 157) and $_{100}$RREPPHCPNSFRLEKIL$_{116}$ (SEQ ID NO: 158), of SEQ ID NO: 105, and Bin B antibodies (mAb7357 and mAbeBio16-7178) bound in region of peptide segment $_{71}$CRHLGCINADGNVDYHM$_{87}$ (SEQ ID NO: 160). mAb317 and mAb3171 bound to sites distinct from each other and from the bin A and bin B antibodies. However, the weak signals in the H/D exchange studies with both antibodies did not provide sufficient evidence to localize their epitopes on IL-17A.

EXAMPLE 5

Co-crystal Structure of IL-17A and Anti-IL-17A Antibody

The co-structure of IL-17Amut6 with the Fab6468, a recombinant His6-tagged Fab of mAb6785, was determined by X-ray crystallography. The amino acid sequence of the light chain of Fab6468 is shown in SEQ ID NO: 90, and the heavy chain amino acid sequence is shown in SEQ ID NO: 111. In the Example 5, the IL-17A amino acid residues referred to indicate residues according to SEQ ID NO: 105, and the Fab6468 residues referred to indicate light chain variable region residues according to SEQ ID NO: 79 and heavy chain variable region residues according to SEQ ID NO: 86. The expression, refolding and purification of recombinant human IL-17Amut6 has been described (Wu et al., Cytokine, ePub ahead of print July 29). Fab6468 was expressed in HEK-293F cells and purified using a similar method as described (Zhao et al., Protein Expr Purif, 67:182-9, 2009).

Crystallization of IL-17A/Fab6468 Complex

The IL-17A/Fab6468 complex was prepared by mixing IL-17Amut6 and Fab6468 in 1:1.1 molar ratio in 20 mM MES pH 6.5, 0.2 M NaCl, and 10% glycerol and incubated over night at 4° C. The complex was purified from excess uncomplexed Fab using size exclusion chromatography (SEC) on a Superdex 200 10/300 GL column (GE Healthcare, Piscataway, N.J.) in 20 mM MES pH 6.5, 0.2 M NaCl, and 10% glycerol. Fractions corresponding to the complex were pooled and concentrated with an Amicon Ultra 10000 MWCO device to 4.6 mg/ml.

Automated crystallization screening was performed using the Oryx4 automatic protein crystallization robot (Douglas Instruments, East Garston, UK) dispensing equal volumes of protein and reservoir solution in a sitting drop format using Corning plate 3550 (Corning Inc., Corning, N.Y.). Initial screening was performed with Hampton Crystal Screen HT (HR2-130, Hampton Research) and produced needle-like crystals from several conditions containing ammonium sulfate, PEGs at pH 4.5-4.6. These small crystals were used to produce a seed stock for microseed-matrix screening (MMS) (D'Arcy et al., Acta Crystallographica Section D, 63:550-4, 2007). Diffraction quality crystals were obtained from the MMS screen in 0.1 M Sodium Acetate pH 5.5, 12% PEG MME 5000 and 0.2 M Lithium Sulfate.

X-ray Data Collection of IL-17A/Fab6468 Complex

For X-ray data collection, the crystal was soaked for a few seconds in the mother liquor supplemented with 24% glycerol, and flash frozen in the stream of nitrogen at 95° K. X-ray diffraction data were collected and processed using a Rigaku MicroMax™-007HF microfocus X-ray generator equipped with an Osmic™ VariMax™ confocal optics, Saturn 944 CCD detector, and an X-stream™ 2000 cryocooling system (Rigaku, Woodlands, Tex.). Diffraction intensities were detected over a 254° crystal rotation with the exposure time of 3 min per half-degree image to the maximum resolution of 2.2 Å. The X-ray data were processed with the program D*TREK (Pflugrath, J., Acta Crystallographica Section D, 55:1718-25, 1999). The crystal belonged to the monoclinic space group P2$_1$ with a=73.40 Å, b=64.04 Å, c=145.61 Å and β=95.39°. The X-ray data statistics are given in Table 8.

TABLE 8

| | |
|---|---|
| Wavelength (Å) | 1.5418 |
| Temperature (K) | 95 |
| Rotation range (°) | 254 |
| Space group | $P2_1$ |
| Unit cell axes (Å) | 73.40, 64.04, 145.61 |
| Unit cell angles (°) | 90, 95.39, 90 |
| Molecules/asymmetric unit | IL-17 dimer + 2 Fabs |
| $V_m$ (Å³/Da) | 2.76 |
| Solvent content (%) | 55 |
| Resolution (Å) | 73-2.2 (2.28-2.20)* |
| No. measured reflections | 251,653 (16,276) |
| No. unique reflections | 61,776 (5,947) |
| Completeness (%) | 89.8 (86.9) |
| Redundancy | 4.1 (2.7) |
| R-merge | 0.151 (0.353) |
| $<I/\sigma>$ | 5.6 (1.9) |
| B-factor (Wilson) (Å²) | 33.3 |

*Values for highest resolution shell are in ( )'s.

Structure Determination

The crystal structure of IL-17A/Fab6468 was determined by molecular replacement using Phaser (Read, Acta Crystallogr D Biol Crystallogr, 57:1373-82, 2001). The search models were IL-17F (PDB ID 1JPY) (Hymowitz et al., EMBO J., 20:5332-41, 2001) and a homology model for the Fv (VH/VL), which was constructed based upon the anti-IL-13 antibody CNTO607 (PDB ID 3G6A) (Teplyakov et al., J. Mol. Biol. 389:115-23, 2009) for both the VH and VL, using Modeller (Accelrys, Calif.). The two constant domains CL/CH1 were taken from PDB ID 8FAB (Strong et al., Biochemistry, 30:3739-48, 1991). The structure refinement was carried with PHENIX (Adams et al., J. Synchrotron. Radiat. 11:53-5, 2004). The two-fold non-crystallographic symmetry was initially imposed in early stages of refinement but was relaxed in the final stages based upon $R_{free}$. Model adjustment and manual rebuilding were done using COOT (Emsley et al., Acta Crystallogr. D. Biol. Crystallogr. 60:2126-32, 2004). The final $R_{cryst}$ and $R_{free}$ were 23.4% and 29.7%, respectively, for all 61,706 independent reflections to 2.2 Å. The refinement statistics are given in Table 9.

TABLE 9

| Structure refinement | |
|---|---|
| Resolution (Å) | 73-2.2 (2.234-2.2) |
| $R_{cryst}/R_{free}$ (%)$^b$ | 23.4/29.7 (27.2/37.7) |
| No. of reflections | |
| Working set | 58,570 |
| Test set (5% data) | 3,136 |
| Rmsd from ideal values | |
| Bond length (Å) | 0.007 |
| Bond angels (°) | 1.1 |
| Average B-factor (Å²) | 28.0 |
| Number of protein atoms | 7,994 |
| Number of Solvent (water + ions) | 864 |
| Ramachandran plot$^c$ | |
| Most Favored regions (%) | 90.5 |
| Additional Allowed (%) | 8.6 |
| Generously allowed | 0.2 |
| Disallowed (%) | 0.7 |

The IL-17A/Fab6468 Complex Structure

The structure of the complex was determined to high resolution (~2.2 Å). IL-17A was a nearly symmetrical homodimer in the crystal and bound two Fab molecules. The antibody-antigen interactions were largely hydrophobic and in contrast to most antibodies, the light chain CDRs made a number of the important contacts. The overall molecular structure of IL-17A/Fab6468 complex is shown in FIG. 6A. The monomer of the IL-17A dimer adopted the overall topology of a cystine knot (FIG. 6B). The two monomers were very similar with a Cα RMSD of 0.54 Å for 77 backbone Cα atoms. The overall architecture of IL-17A monomer cystine knot was very similar to that of IL-17F with an rmsd of 0.71 Å for 76 Cα atoms (FIG. 6B). Each IL-17A monomer was stabilized by three disulfide bonds. For chain B, three intra-chain disulfide bonds were observed ($C^{10}$-$C^{106}$, $C^{71}$-$C^{121}$, $C^{76}$-$C^{123}$), whereas for chain A the $C^{10}$-$C^{106}$ disulfide bond was not observed due to disorder in these segments of the monomer. The latter two disulfide bonds ($C^{71}$-$C^{121}$, $C^{76}$-$C^{123}$) stabilized the cystine knot architecture, analogous to IL-17F and NGF. The structural model for chain B of IL-17A included all residues 10-128 (residues 1-9 were disordered), whereas for chain A residues only residues 21-29, 41-104 and 109-127 were observed and the other residues 1-20, 30-40, 105-108 and 128 were missing due to disorder in the structure. For the two Fabs, residues 1-2 of both the light chains were disordered or had poor electron density. The C-terminal 3 residues of both the heavy and light chains, including the inter-chain disulfide bonds as well as the His tag on the heavy chain were disordered.

The ordered N-terminal segment of IL-17A (chain B) contained a short helical element (residues 8-12). It folded back towards the loop 3-4 of the same monomer and formed an intra-chain disulfide bond ($C^{10}$-$C^{106}$). In contrast, the equivalent segment of IL-17F reached over to the other monomer of the dimer and formed an inter-chain disulfide bond and linked the two monomers covalently. The ordered parts of the segments 17-39 of the two IL-17A monomers were swapped, as in IL-17F. This swapping resulted in a cross-over for these parts of the IL-17A dimer. Combined with the intra-molecular disulfide bond ($C^{10}$-$C^{106}$), the two N-terminal segments of IL-17A formed two inter-locked monomers, which also gave rise to an apparent dimer of 26 kD on non-reducing SDS-PAGE.

The dimer of the IL-17A was nearly symmetrical for the four main β-strands (strands 1-4) (FIG. 6C). The Cα rmsd for 76 residues is 0.71 Å. The slight asymmetry came from two sources. First, the chain A contained a number of disordered segments, mainly in N-terminus. Only a short β-strand (strand 0, residues 22-26) was apparently ordered, whereas residues 10-40 of chain B were ordered with a helical segment (residues 12-16) and a β-strand (strand 0, residues 21-25). Second, while the cystine knotted four main β-strands of the two monomers (40-128) of the IL-17A were related by a two-fold symmetry of rotation, the ordered parts of strand 0 did not superimpose well when the main body is overlaid (not shown). Whether this was an artifact of protein refolding or such an arrangement exists in nature is not clear without further investigation. The bioactivity of this species was similar to that of a reference IL-17A from a commercial source (also produced in *E. coli*) (R&D Systems, Minneapolis, Minn.) suggesting that the inter- or intra-chain disulfide linkage for the $C^{10}$-$C^{106}$ is not important for its receptor binding. Nevertheless, the current structure suggests that the N-terminal segments (1-20) and (30-39) are very flexible and their structures do not impact the activity of the folded IL-17A dimer.

The Epitope and the Paratope

Figure 7:
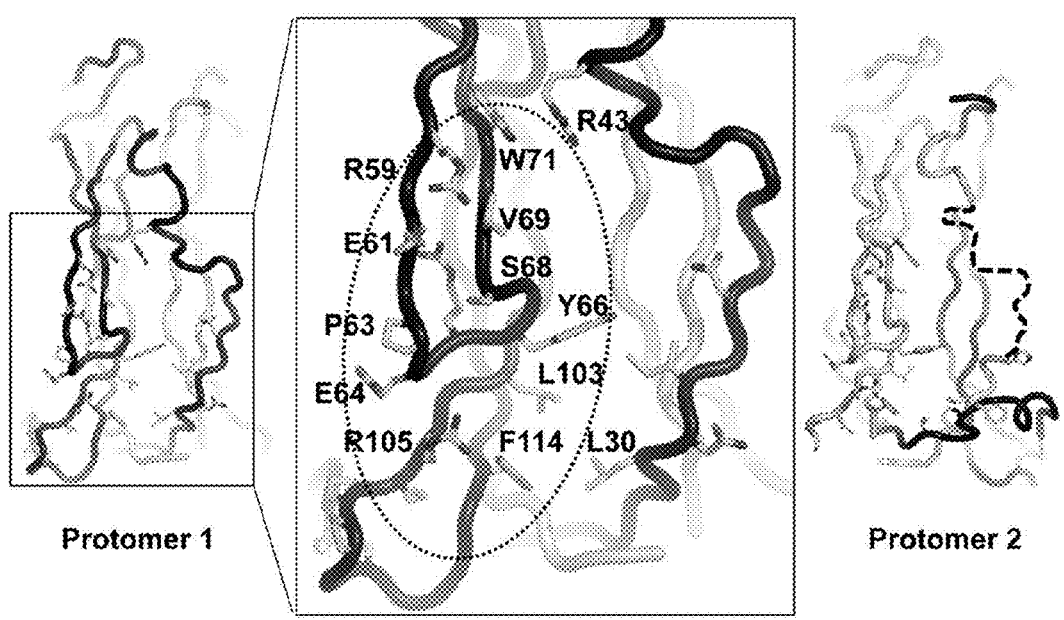
FIG. 7. The two binding sites and the core epitope on IL-17A for Fab6468. Protomers 1 and 2 are dark and light gray, respectively. The core epitope is indicated by the black oval. The broken line represents disordered residues.

The residues involved in binding between IL-17A and Fab6468 are listed in Table 10. Due to the missing residues in protomer A in the IL-17A dimer and the slight asymmetrical nature of the IL-17A dimer, all epitope residues from the two contact sites were not identical (Table 10 and FIG. 7). However, there was a core set of residues as well as their interactions that were identical. These residues were L26, R55, E57, P59, E60, R61, Y62, S64, V65, W67, R101, E102, P103 and F110 of IL-17A SEQ ID NO: 105 (highlighted black in Table 10), and they constitute the core epitope for Fab6468.

N-terminal region of VH (see Example 1), 3 residues at the N-terminus of VL (see Example 1), and 3 CDR residues (one each in H2, H3 and L3, Table 1a), none of which are part of the antibody paratope.

TABLE 10

Core epitope residues are highlighted in black. Core paratope residues are bolded. Extended paratope residues are shown in parenthesis.

| VL | Il-17A epitope on monomer B | VH | VL | IL-17A epitope on monomer A | VH |
|---|---|---|---|---|---|
| (D25) | F18 | | | | |
| (F93) | P19 | | | | |
| (F93) | V22 | | | | |
| F93 | L26 | | F93 | L26 | |
| | | | (N26) | N27 | |
| | | | (D29), (F93) | I28 | |
| (D29) | H29 | | (G28) | N30 | |
| | | | (D50), (I51), (Y31) | N36 | |
| | | | (I51), (D52), (D49), (Y31) | R39 | |
| D49 | R55 | T101, Q99 | (Y48), D49 | R55 | T101, Q99 |
| | E57 | L100, Q99, T101 | | E57 | L100, Q99, T101 |
| Y90, F92 | P59 | Y59, (L100) | Y90, F92 | P59 | (S52), Y59 |
| F92 | E60 | Y59, F57, S52, T54 | F92 | E60 | Y59, F57, S52, T54 |
| F92 | R61 | | F92 | R61 | |
| F92 | Y62 | | F92, (F93), (D29) | Y62 | |
| Y90 | S64 | | Y90 | S64 | (L100) |
| Y31 | V65 | | Y31, (D49) | V65 | |
| D49, (Y31) | W67 | | D49, (D52), (Y48) | W67 | |
| | L99 | | (F93) | L99 | |
| F92, Y90 | R101 | F57, Y59 | Y90, F92 | R101 | F57, Y59 |
| | E102 | F57 | | E102 | F57 |
| | P103 | F57 | | P103 | F57 |
| | P104 | | | P104 | (G56) |
| F92 | F110 | | F92, (F93) | F110 | |

Similarly, the contact residues from the antibodies in the two sites were not all identical. The residues involved in identical contacts to the core epitope residues are referred to as the "core paratope", which was composed of the following residues: Light Chain (LC): Y31, D49, Y90, F92, F93 (SEQ ID NO: 79); and heavy chain (HC): S52, T54, F57, Y59, Q99, L100 and T101 (SEQ ID NO: 86) (Table 10). The core paratope residues are shown in bold in Table 10. The additional "extended paratope" residues identified in one monomer binding a specific IL-17A residue are shown in parenthesis.

The H/D protection data for the MORmAb7700 was in agreement with the co-crystal studies, as all core epitope residues identified in the co-crystal structure except L26 were within or at the borders of two of the protected segments identified by H/D exchange, $_{56}$NEDPERYPSVIWE$_{68}$ (SEQ ID NO: 157) and $_{100}$RREPPHCPNSFRLEKIL$_{116}$ (SEQ ID NO: 158) for the MORmAb7700. All of the MORmAb7700 antibody derivatives, including MORmAb8302 and mAb1926, are assumed to have the same binding specificity as Fab6468 since they differ at most by one residue in the The IL-17A structure characterized in this invention is very similar to the previously published structure, except that due to missing segments, the P2 pocket cavity (see below) was not identified in the previous work (structure 2VXS, available at the Protein DataBank http_//www_rcsb_org/pdb/home/home_do; Gerhardt et al., J. Mol. Biol. 394:905-21, 2009).

The crystal structure of the human IL-17F in complex with IL-17RA has been reported (Ely et al., Nat. Immunology, 10:1245-51, 2009). Because of the sequence and structural similarities between IL-17A and IL-17F, it is likely that IL-17A will interact with the IL-17RA in a similar manner to IL-17F. Molecular modeling by overlaying the IL-17A structure in complex with Fab6468 obtained in this study onto the IL-17F in the reported IL-17F/IL-17RA complex showed that segments of Fab6468 would have steric clashes with IL-17RA. One of these segments localize around the FF motif (residues 92 and 93 of SEQ ID NO: 79) in the light chain CDR3 of Fab6468. Thus, not wishing to be bound by any particular theory, it is suggested that Fab6468 would inhibit IL-17A function by blocking its interactions with IL-17RA and by analogy, IL-17RC, though the mode of interaction between IL-17RC and IL-17A is not known at the molecular level.

The significant differences in the affinities of IL-17A and IL-17F for IL-17RA suggest there may be significant differences in the details of IL-17A and IL-17RA interactions, the extent of which will only be available when the co-crystal structure of IL-17A/IL-17RA is determined. This is implicated by the identification of the P2 pocket cavity in this study, which is only partially identified in IL-17F analogous region in the reported IL-17F/IL-17RA crystal structure (Ely et al., Nat. Immunology, 10:1245-51, 2009).

Two deep, largely hydrophobic pockets were identified on the surface of IL-17A along the dimer interface (FIG. 8A, 5B). The P1 pocket, which is analogous to a pocket first discovered in IL-17F (Hymowitz et al., EMBO J, 20: 5332-41, 2001), is composed of residues Q94, E95, L97 and K114 of monomer A and L53, Y62, P63, V65, 166, W67, 196, V117 and V119 of monomer B, and vice versa. On one side of the dimer, the P1 pocket is partially covered by the segment 30-40, whereas on the other side it was completely open due to the segment being disordered. Since this segment appears to be flexible, the P1 pocket would be accessible by other molecules. The P2 pocket is also composed of residues from both chains: V24, L26, I28, Y62, L99, R101, F110 and L112 of monomer A and V22, V24 and L112 of monomer B, and vice versa.

Though the details of the P2 pockets are slightly different due to the asymmetry of the IL-17A dimer as described above, the overall geometry of the two P2 pockets is very similar. The two sets of residues lining the P1 and P2 pockets are very well conserved between IL-17A and IL-17F (FIG. 8C). However, in the IL-17F structure, the P2 pocket is occupied by residues F10 and F11 ($F_{10}F_{11}$ motif) (FIG. 8B) (Hymowitz et al., EMBO J, 20: 5332-41, 2001). The FF motif is absent in human IL-17A; instead, the corresponding amino acid residues are 14 and P5 (residues 4 and 5 in SEQ ID NO: 105) (FIG. 8C). These residues are not likely to bind in the P2 pocket as well as the FF motif because they are much smaller than the phenylalanine residues, and most likely will not have sufficient affinity for the P2 pocket. Thus, the FF motif of IL-17F is likely a structural discriminant for human IL-17A and IL-17F interactions with receptors IL-17RA and IL-17RC. It is likely that both of these largely hydrophobic pockets (P1 and P2) are required for IL-17A binding to IL-17RA. The recent crystal structure of IL-17F/IL-17RA complex shows that the FF motif is displaced by IL-17RA (Ely et al., Nat. Immunology 10:1245-51, 2009). The energetic penalty of FF motif eviction from P2 likely results in lower binding affinity. This is consistent with the observations that IL-17RA binds IL-17A with high affinity but IL-17F with low affinity in humans (Kuestner et al., J Immunol, 179:5462-73, 2007), and potentially could explain the differences in IL-17A and IL-17F potencies. In mice, the FF motif is absent in both IL-17A and IL-17F, and is replaced by residues IP and AL, respectively. The AL and IP residue pairs are small and likely to have low affinity for the P2 pocket. Thus, P2 would be available in mouse IL-17A and IL-17F for IL-17RA binding. Both mouse IL-17A and IL-17F bind mouse IL-17RA with similar affinity (Kuestner et al., J Immunol, 179:5462-73, 2007), consistent with the present suggestion that availability of P2 pocket for binding increases affinity of the ligands.

Overall, the structural differences observed between IL-17A and IL-17F provides a basis for dissecting their interactions with respective receptors. Furthermore, it is conceivable that peptides, peptidomimetics and small molecules can be designed to bind in either or both pockets to block IL-17A and/or IL-17F from interacting with their receptors. Since the FF motif present in Fab6468 (residues F92 and F93 in SEQ ID NO: 79) binds P2 pocket residues L26, R61, L99, R101 and R102, the Fab 6468 structure could be used to select and optimize additional IL-17A antagonists, such as peptides from randomized or designed peptide libraries using phage display.

The residues lining the P1 and P2 pockets are well conserved between IL-17A and IL-17F and molecular modeling suggests that an IL-17A/F heterodimer would adopt a nearly identical overall structure when compared to the IL-17A homodimer alone. Therefore, it is likely that the P1 and P2 pockets are present in the IL-17A/F heterodimer with similar overall topology and constitute its receptor binding sites. Thus IL-17A antagonists binding to the P2 pocket residues could bind and antagonize the IL-17A/F heterodimer.

EXAMPLE 6

Cross-species Binding Specificity

Figure 9:
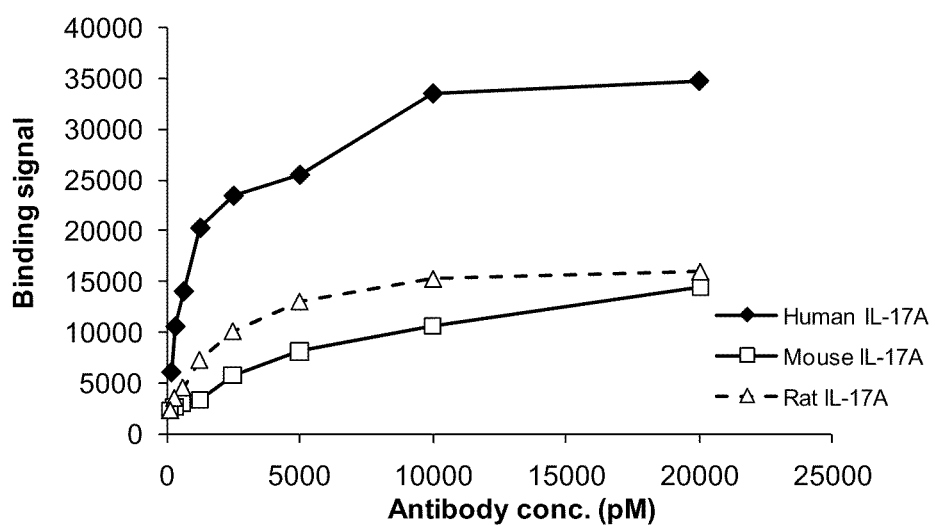
FIG. 9. Binding specificity of mAb1926 to different species of IL-17A proteins in an ELISA format.

To evaluate cross-species binding specificity of mAbtr1926, a binding ELISA was performed with different IL-17A proteins coated on micro-titer plates. Human, mouse and rat IL-17A proteins were coated on the micro-titer plates. Serial dilutions of labeled mAb1926 were incubated at 37° C. for 2 hours. Following incubation, micro-titer plates were washed thoroughly, and bound labeled mAb1926 was detected. mAb 1926 bound to human IL-17A much stronger than to rat or mouse IL-17A proteins (FIG. 9). This reduced binding to rat and mouse IL-17A is consistent with these proteins both differing from human IL-17A at 7 positions of the Fab6468 extended epitope (Table 10). In addition, there is a one amino acid insertion in rat and mouse IL-17A between residues 40 and 41 of human IL-17A, a position close to part of the Fab 6468 epitope.

The invention claimed is:

1. An isolated antibody or fragment thereof that binds specifically to human IL-17A, comprising a heavy chain variable region (VH) and a light chain variable region (VL), wherein the VH region comprises the HCDR1, HCDR2 and HCDR3 having the amino acid sequences as shown in SEQ ID NOs:25, 46 and 61, respectively; and the VL region comprises the LCDR1, LCDR2, and LCDR3 having the amino acid sequences as shown in SEQ ID NOs:3, 6 and 22, respectively; and wherein in SEQ ID NO:46,
Xaa1 may be Ala, Gly, Thr or Val;
Xaa3 may be Asn or Ser;
Xaa4 may be Gly, Met, Lys, Ile, Leu or His;
Xaa5 may be Leu, Asp, Ala, His, Thr, Gly or Ser;
Xaa6 may be Gly or Ser;
Xaa7 may be Thr, Gly, Tyr or Asp;
Xaa8 may be His, Trp, Tyr or Phe;
Xaa9 may be Lys, Thr or Ile; and
Xaa10 may be Tyr, Phe or Asn;
in SEQ ID NO:61,
Xaa may be Met, Leu or Thr; and
in SEQ ID NO:22,
Xaa is Met, Leu, Thr or Tyr.

2. The isolated antibody or fragment of claim 1, wherein the antibody comprises the HCDR1, HCDR2 and HCDR3 amino acid sequences as shown in:
a. SEQ ID NOs: 25, 37 and 58, respectively;
b. SEQ ID NOs: 25, 38 and 58, respectively;
c. SEQ ID NOs: 25, 39 and 58, respectively;
d. SEQ ID NOs: 25, 40 and 58, respectively;
e. SEQ ID NOs: 25, 41 and 58, respectively;
f. SEQ ID NOs: 25, 42 and 58, respectively;
g. SEQ ID NOs: 25, 43 and 58, respectively;
h. SEQ ID NOs: 25, 41 and 59, respectively;
i. SEQ ID NOs: 25, 41 and 60, respectively;
j. SEQ ID NOs: 25, 43 and 60, respectively;
k. SEQ ID NOs: 25, 44 and 58, respectively; or
l. SEQ ID NOs: 25, 45 and 58, respectively; and
the LCDR1, LCDR2, and LCDR3 amino acid sequences as shown in:
m. SEQ ID NOs: 3, 6 and 18, respectively;
n. SEQ ID NOs: 3, 6 and 19, respectively;
o. SEQ ID NOs: 3, 6 and 20, respectively; or
p. SEQ ID NOs: 3, 6 and 21, respectively.

3. An isolated monoclonal antibody or fragment thereof that binds specifically to human IL-17A that competes for human IL-17A binding with a monoclonal antibody comprising the heavy chain CDR 1, 2 and 3 (HCDR1, HCDR2 and HCDR3) amino acid sequences as shown in SEQ ID NOs: 25, 43 and 60, respectively, and the light chain CDR 1, 2 and 3 (LCDR1, LCDR2 and LCDR3) amino acid sequences as shown in SEQ ID NOs: 3, 6 and 18, respectively.

4. The isolated antibody or fragment of claim 3 or 1, wherein the antibody is fully human.

5. The isolated antibody or fragment of claim 3 or 1, wherein the antibody is conjugated to polyethylene glycol.

6. The isolated antibody or fragment of claim 3 or 1, having an IgG1 or IgG4 isotype.

7. The isolated antibody or fragment of claim 3 or 1, wherein the Fc domain comprises S229P, P235A or L236A mutations in the Fc domain.

8. A pharmaceutical composition comprising the isolated antibody or fragment of claim 3 or 1 and a pharmaceutically acceptable carrier.

9. An isolated antibody or fragment thereof that binds specifically to human IL-17A comprising a VH and a VL, wherein the antibody comprises:
a. the HCDR1, HCDR2 and HCDR3 amino acid sequences as shown in SEQ ID NOs: 25, 43 and 60, respectively and
the LCDR1, LCDR2, and LCDR3 amino acid sequences as shown in SEQ ID NOs: 3, 6 and 18, respectively; or
b. the VH of SEQ ID NO: 86; or
c. the VL of SEQ ID NO: 79; or
d. the VH of SEQ ID NO: 86 and the VL of SEQ ID NO: 79.

10. An isolated antibody or fragment thereof that binds specifically to human IL-17A, comprising a VH and a VL, wherein the antibody comprises the VH having the amino acid sequence shown in SEQ ID NO: 86.

11. The isolated antibody or fragment of claim 10, wherein the antibody comprises the VL having the amino acid sequence shown in SEQ ID NO: 79.

12. An isolated antibody or fragment thereof that binds specifically to human IL-17A, comprising a VH and a VL, wherein the antibody comprises the VL having the amino acid sequence shown in SEQ ID NO: 79.

13. An isolated antibody or fragment thereof that binds specifically to human IL-17A, comprising a VH and a VL, wherein the antibody comprises the VH which is at least 95% identical to the VH having the amino acid sequence shown in SEQ ID NO: 86.

14. An isolated antibody or fragment thereof that binds specifically to human IL-17A, comprising a VH and a VL, wherein the antibody comprises the VL which is at least 95% identical to the variable region having the amino acid sequence shown in SEQ ID NO: 79.

15. An isolated antibody or fragment thereof that binds specifically to human IL-17A, comprising an antibody heavy chain having the amino acid sequence shown in SEQ ID NO: 100.

16. An isolated antibody or fragment thereof that binds specifically to IL-17A, comprising an antibody light chain having the amino acid sequence shown in SEQ ID NO: 90.

* * * * *

SEQUENCE LISTING

<160> NUMBER OF SEQ ID NOS: 160

<210> SEQ ID NO 1
<211> LENGTH: 11
<212> TYPE: PRT
<213> ORGANISM: Artificial Sequence
<220> FEATURE:
<223> OTHER INFORMATION: LCDR1 of Family 2 antibodies

<400> SEQUENCE: 1

Arg Ala Ser Gln Gly Ile Ser Asn Trp Leu Asn
1               5                   10

```
<210> SEQ ID NO 2
<211> LENGTH: 12
<212> TYPE: PRT
<213> ORGANISM: Artificial Sequence
<220> FEATURE:
<223> OTHER INFORMATION: LCDR1 of Family 6a and 6b antibodies

<400> SEQUENCE: 2

Arg Ala Ser Gln Asn Val Trp Ala Phe Tyr Leu Ala
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: LCDR1 of Family 19a and 19b antibodies

<400> SEQUENCE: 3

Ser Gly Asp Asn Leu Gly Asp Lys Tyr Ala Asn
 1               5                  10

<210> SEQ ID NO 4
<211> LENGTH: 7
<212> TYPE: PRT
<213> ORGANISM: Artificial Sequence
<220> FEATURE:
<223> OTHER INFORMATION: LCDR2 of Family 2 antibodies

<400> SEQUENCE: 4

Ala Ala Ser Ser Leu Gln Ser
 1               5

<210> SEQ ID NO 5
<211> LENGTH: 7
<212> TYPE: PRT
<213> ORGANISM: Artificial Sequence
<220> FEATURE:
<223> OTHER INFORMATION: LCDR2 of Family 6a and 6b antibodies

<400> SEQUENCE: 5

Gly Ala Ser Asn Arg Ala Thr
 1               5

<210> SEQ ID NO 6
<211> LENGTH: 7
<212> TYPE: PRT
<213> ORGANISM: Artificial Sequence
<220> FEATURE:
<223> OTHER INFORMATION: LCDR2 of Family 19a and 19b antibodies

<400> SEQUENCE: 6

Asp Asp Ile Asp Arg Pro Ser
 1               5

<210> SEQ ID NO 7
<211> LENGTH: 8
<212> TYPE: PRT
<213> ORGANISM: Artificial Sequence
<220> FEATURE:
<223> OTHER INFORMATION: LCDR3 of Family 2 antibodies

<400> SEQUENCE: 7

Gln Gln Tyr Ser Asp Asp Pro Thr
 1               5
```

```
<210> SEQ ID NO 8
<211> LENGTH: 9
<212> TYPE: PRT
<213> ORGANISM: Artificial Sequence
<220> FEATURE:
<223> OTHER INFORMATION: LCDR3 of Family 6a clone 10 antibody

<400> SEQUENCE: 8

His Gln Phe Thr Ile Pro Ser His Thr
 1               5

<210> SEQ ID NO 9
<211> LENGTH: 9
<212> TYPE: PRT
<213> ORGANISM: Artificial Sequence
<220> FEATURE:
<223> OTHER INFORMATION: LCDR3 of Family 6a clone 11 antibody

<400> SEQUENCE: 9

Gln Gln Phe Val Thr Pro Ser Phe Thr
 1               5

<210> SEQ ID NO 10
<211> LENGTH: 9
<212> TYPE: PRT
<213> ORGANISM: Artificial Sequence
<220> FEATURE:
<223> OTHER INFORMATION: LCDR3 of Family 6a clone 12 antibody

<400> SEQUENCE: 10

Gln Gln Gly Asn Tyr Arg Pro Leu Thr
 1               5

<210> SEQ ID NO 11
<211> LENGTH: 8
<212> TYPE: PRT
<213> ORGANISM: Artificial Sequence
<220> FEATURE:
<223> OTHER INFORMATION: Consensus LCDR3 of Family 6a antibodies,
      Formula II
<220> FEATURE:
<221> NAME/KEY: VARIANT
<222> LOCATION: 1
<223> OTHER INFORMATION: Xaa may be His or Gln
<220> FEATURE:
<221> NAME/KEY: VARIANT
<222> LOCATION: 3
<223> OTHER INFORMATION: Xaa may be Phe or Gly
<220> FEATURE:
<221> NAME/KEY: VARIANT
<222> LOCATION: 4
<223> OTHER INFORMATION: Xaa may be Thr, Val or Asn
<220> FEATURE:
<221> NAME/KEY: VARIANT
<222> LOCATION: 5
<223> OTHER INFORMATION: Xaa may be Ile, Thr or Tyr
<220> FEATURE:
<221> NAME/KEY: VARIANT
<222> LOCATION: 6
<223> OTHER INFORMATION: Xaa may be Pro or Arg
<220> FEATURE:
<221> NAME/KEY: VARIANT
<222> LOCATION: 7
<223> OTHER INFORMATION: Xaa may be Ser or Pro
<220> FEATURE:
<221> NAME/KEY: VARIANT
<222> LOCATION: 8
<223> OTHER INFORMATION: Xaa may be His, Phe or Leu

<400> SEQUENCE: 11

Xaa Gln Xaa Xaa Xaa Xaa Xaa Xaa
 1               5
```

<210> SEQ ID NO 12
<211> LENGTH: 10
<212> TYPE: PRT
<213> ORGANISM: Artificial Sequence
<220> FEATURE:
<223> OTHER INFORMATION: LCDR3 of Family 6b clone 13

<400> SEQUENCE: 12

Gln Gln Ser Asn His Ile Pro Pro Ala Thr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: LCDR3 of Family 6b MOR7706, 8299, 8300, 8301

<400> SEQUENCE: 13

Gln Gln Tyr Arg Ser Thr Leu Ser Leu Thr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: LCDR3 of Family 6b clone 15

<400> SEQUENCE: 14

Gln Gln Tyr Val Ser Leu Ser Phe Asp Thr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: LCDR3 of Family 6b clone 16

<400> SEQUENCE: 15

Gln Gln Tyr Tyr Ser Ala Pro Leu Leu Thr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: LCDR3 of Family 6b MOR7775, 8101, 8102, 8103

<400> SEQUENCE: 16

Thr Gln Tyr Tyr Ser Ser Pro Ser Leu Thr
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Consensus LCDR3 of Family 6b antibodies,
      Formula III
<220> FEATURE:
<221> NAME/KEY: VARIANT
<222> LOCATION: 1
<223> OTHER INFORMATION: Xaa may be Gln or Thr
<220> FEATURE:
<221> NAME/KEY: VARIANT
<222> LOCATION: 3

```
<223> OTHER INFORMATION: Xaa may be Ser or Tyr
<220> FEATURE:
<221> NAME/KEY: VARIANT
<222> LOCATION: 4
<223> OTHER INFORMATION: Xaa may be Asn, Arg, Val or Tyr
<220> FEATURE:
<221> NAME/KEY: VARIANT
<222> LOCATION: 5
<223> OTHER INFORMATION: Xaa may be His or Ser
<220> FEATURE:
<221> NAME/KEY: VARIANT
<222> LOCATION: 6
<223> OTHER INFORMATION: Xaa may be Ile, Thr, Leu, Ala or Ser
<220> FEATURE:
<221> NAME/KEY: VARIANT
<222> LOCATION: 7
<223> OTHER INFORMATION: Xaa may be Pro, Leu or Ser
<220> FEATURE:
<221> NAME/KEY: VARIANT
<222> LOCATION: 8
<223> OTHER INFORMATION: Xaa may be Pro, Ser, Phe or Leu
<220> FEATURE:
<221> NAME/KEY: VARIANT
<222> LOCATION: 9
<223> OTHER INFORMATION: Xaa may be Ala, Leu or Asp

<400> SEQUENCE: 17

Xaa Gln Xaa Xaa Xaa Xaa Xaa Xaa Xaa Thr
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: LCDR3 of Family 19a clone 178, 179, 181, 184,
      MOR 7709, 7700, 8095, 8097, 8098, 8302, 8096, 7768 and
      Family 19b

<400> SEQUENCE: 18

Gly Ser Tyr Asp Phe Phe Leu Gly Met Ile Val
 1               5                  10

<210> SEQ ID NO 19
<211> LENGTH: 11
<212> TYPE: PRT
<213> ORGANISM: Artificial Sequence
<220> FEATURE:
<223> OTHER INFORMATION: LCDR3 of Family 19a clone MOR 8141, 8160, mAb
      5548

<400> SEQUENCE: 19

Gly Ser Tyr Asp Phe Phe Leu Gly Leu Ile Val
 1               5                  10

<210> SEQ ID NO 20
<211> LENGTH: 11
<212> TYPE: PRT
<213> ORGANISM: Artificial Sequence
<220> FEATURE:
<223> OTHER INFORMATION: LCDR3 of Family 19a clone MOR 8142, 8161, 8303

<400> SEQUENCE: 20

Gly Ser Tyr Asp Phe Phe Leu Gly Thr Ile Val
 1               5                  10

<210> SEQ ID NO 21
<211> LENGTH: 11
<212> TYPE: PRT
<213> ORGANISM: Artificial Sequence
<220> FEATURE:
<223> OTHER INFORMATION: LCDR3 of Family 19a clone MOR 8143, 8162
```

```
<400> SEQUENCE: 21

Gly Ser Tyr Asp Phe Phe Leu Gly Tyr Ile Val
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Consensus LCDR3 of Family 19a antibodies,
      Formula V
<220> FEATURE:
<221> NAME/KEY: VARIANT
<222> LOCATION: 9
<223> OTHER INFORMATION: Xaa may be Met, Leu, Thr or Tyr

<400> SEQUENCE: 22

Gly Ser Tyr Asp Phe Phe Leu Gly Xaa Ile Val
1               5                   10

<210> SEQ ID NO 23
<211> LENGTH: 5
<212> TYPE: PRT
<213> ORGANISM: Artificial Sequence
<220> FEATURE:
<223> OTHER INFORMATION: HCDR1 of Family 2

<400> SEQUENCE: 23

Ser Tyr Ala Ile Ser
1               5

<210> SEQ ID NO 24
<211> LENGTH: 7
<212> TYPE: PRT
<213> ORGANISM: Artificial Sequence
<220> FEATURE:
<223> OTHER INFORMATION: HCDR1 of Family 6a and 6b

<400> SEQUENCE: 24

Ser Ser Ser Ala Ala Trp Gly
1               5

<210> SEQ ID NO 25
<211> LENGTH: 5
<212> TYPE: PRT
<213> ORGANISM: Artificial Sequence
<220> FEATURE:
<223> OTHER INFORMATION: HCDR1 of Family 19a and 19b

<400> SEQUENCE: 25

Ser Tyr Ala Met Ser
1               5

<210> SEQ ID NO 26
<211> LENGTH: 17
<212> TYPE: PRT
<213> ORGANISM: Artificial Sequence
<220> FEATURE:
<223> OTHER INFORMATION: HCDR2 of Family 2 7702

<400> SEQUENCE: 26

His Ile Ile Pro Trp Phe Gly Trp Thr Tyr Tyr Ala Gln Lys Phe Gln
1               5                   10                  15

Gly

<210> SEQ ID NO 27
```

```
<211> LENGTH: 17
<212> TYPE: PRT
<213> ORGANISM: Artificial Sequence
<220> FEATURE:
<223> OTHER INFORMATION: HCDR2 of Family 2 7701

<400> SEQUENCE: 27

Met Ile Ile Pro Trp Phe Gly Thr Thr Phe Tyr Ala Gln Lys Phe Gln
 1               5                  10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: HCDR2 of Family 2 7708

<400> SEQUENCE: 28

Arg Ile Ile Pro Trp Phe Gly Trp Thr Ser Tyr Ala Gln Lys Phe Gln
 1               5                  10                  15

Gly

<210> SEQ ID NO 29
<211> LENGTH: 17
<212> TYPE: PRT
<213> ORGANISM: Artificial Sequence
<220> FEATURE:
<223> OTHER INFORMATION: HCDR2 of Family 2 8297

<400> SEQUENCE: 29

Arg Ile Ile Pro Trp Phe Gly Thr Thr Ser Tyr Ala Gln Lys Phe Gln
 1               5                  10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: HCDR2 of Family 2 8298

<400> SEQUENCE: 30

Arg Ile Ile Pro Trp Phe Gly Tyr Thr Ser Tyr Ala Gln Lys Phe Gln
 1               5                  10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: HCDR2 of Family 2 7785

<400> SEQUENCE: 31

Ser Ile Ile Pro Trp Phe Gly Trp Thr Asn Tyr Ala Gln Lys Phe Gln
 1               5                  10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: HCDR2 of Family 2 8104
```

```
<400> SEQUENCE: 32

Ser Ile Ile Pro Trp Phe Gly Thr Thr Asn Tyr Ala Gln Lys Phe Gln
 1               5                  10                  15

Gly

<210> SEQ ID NO 33
<211> LENGTH: 17
<212> TYPE: PRT
<213> ORGANISM: Artificial Sequence
<220> FEATURE:
<223> OTHER INFORMATION: HCDR2 of Family 2 8105

<400> SEQUENCE: 33

Ser Ile Ile Pro Trp Phe Gly Tyr Thr Asn Tyr Ala Gln Lys Phe Gln
 1               5                  10                  15

Gly

<210> SEQ ID NO 34
<211> LENGTH: 17
<212> TYPE: PRT
<213> ORGANISM: Artificial Sequence
<220> FEATURE:
<223> OTHER INFORMATION: HCDR2 of Family 2 7786

<400> SEQUENCE: 34

Tyr Ile Ile Pro Trp Phe Gly Trp Thr Asn Tyr Ala Gln Lys Phe Gln
 1               5                  10                  15

Gly

<210> SEQ ID NO 35
<211> LENGTH: 17
<212> TYPE: PRT
<213> ORGANISM: Artificial Sequence
<220> FEATURE:
<223> OTHER INFORMATION: Consensus HCDR2 of Family 2 Formula I
<220> FEATURE:
<221> NAME/KEY: VARIANT
<222> LOCATION: 1
<223> OTHER INFORMATION: Xaa may be His, Met, Arg, Ser or Tyr
<220> FEATURE:
<221> NAME/KEY: VARIANT
<222> LOCATION: 8
<223> OTHER INFORMATION: Xaa may be Trp, Thr or Tyr
<220> FEATURE:
<221> NAME/KEY: VARIANT
<222> LOCATION: 10
<223> OTHER INFORMATION: Xaa may be Tyr, Phe, Ser or Asp

<400> SEQUENCE: 35

Xaa Ile Ile Pro Trp Phe Gly Xaa Thr Xaa Tyr Ala Gln Lys Phe Gln
 1               5                  10                  15

Gly

<210> SEQ ID NO 36
<211> LENGTH: 18
<212> TYPE: PRT
<213> ORGANISM: Artificial Sequence
<220> FEATURE:
<223> OTHER INFORMATION: HCDR2 of Family 6a

<400> SEQUENCE: 36

Arg Ile Ser Tyr Arg Ser Lys Trp Tyr Asn Asp Tyr Ala Val Ser Val
 1               5                  10                  15

Lys Ser
```

```
<210> SEQ ID NO 37
<211> LENGTH: 17
<212> TYPE: PRT
<213> ORGANISM: Artificial Sequence
<220> FEATURE:
<223> OTHER INFORMATION: HCDR2 of Family 19a clone 179

<400> SEQUENCE: 37

Ala Ile Asn Gly Leu Gly Thr His Lys Tyr Tyr Ala Asp Ser Val Lys
 1               5                  10                  15

Gly

<210> SEQ ID NO 38
<211> LENGTH: 17
<212> TYPE: PRT
<213> ORGANISM: Artificial Sequence
<220> FEATURE:
<223> OTHER INFORMATION: HCDR2 of Family 19a clone 180

<400> SEQUENCE: 38

Ala Ile Ser Met Asp Gly Gly Trp Thr Tyr Tyr Ala Asp Ser Val Lys
 1               5                  10                  15

Gly

<210> SEQ ID NO 39
<211> LENGTH: 17
<212> TYPE: PRT
<213> ORGANISM: Artificial Sequence
<220> FEATURE:
<223> OTHER INFORMATION: HCDR2 of Family 19a MOR 7709

<400> SEQUENCE: 39

Gly Ile Asn Lys Ala Gly Tyr Tyr Thr Tyr Tyr Ala Asp Ser Val Lys
 1               5                  10                  15

Gly

<210> SEQ ID NO 40
<211> LENGTH: 17
<212> TYPE: PRT
<213> ORGANISM: Artificial Sequence
<220> FEATURE:
<223> OTHER INFORMATION: HCDR2 of Family 19a clone 182

<400> SEQUENCE: 40

Gly Ile Ser Gly His Gly Gly Tyr Lys Phe Tyr Ala Asp Ser Val Lys
 1               5                  10                  15

Gly

<210> SEQ ID NO 41
<211> LENGTH: 17
<212> TYPE: PRT
<213> ORGANISM: Artificial Sequence
<220> FEATURE:
<223> OTHER INFORMATION: HCDR2 of Family 19a MOR 7700, 8097, 8098, 8141,
      8142, 8143, 8160, 8161, 8162

<400> SEQUENCE: 41

Thr Ile Ser Met Thr Ser Gly Phe Thr Tyr Tyr Ala Asp Ser Val Lys
 1               5                  10                  15

Gly

<210> SEQ ID NO 42
<211> LENGTH: 17
<212> TYPE: PRT
```

```
<213> ORGANISM: Artificial Sequence
<220> FEATURE:
<223> OTHER INFORMATION: HCDR2 of Family 19a MOR 8095

<400> SEQUENCE: 42

Thr Ile Ser Ile Thr Ser Gly Phe Thr Tyr Tyr Ala Asp Ser Val Lys
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: HCDR2 of Family 19a MOR 8096, 8302, 8303, mAb
      5548

<400> SEQUENCE: 43

Thr Ile Ser Leu Thr Ser Gly Phe Thr Tyr Tyr Ala Asp Ser Val Lys
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: HCDR2 of Family 19a MOR 7768

<400> SEQUENCE: 44

Val Ile Asn Lys Gly Gly Asp Phe Lys Tyr Tyr Ala Asp Ser Val Lys
1               5                   10                  15

Gly

<210> SEQ ID NO 45
<211> LENGTH: 17
<212> TYPE: PRT
<213> ORGANISM: Artificial Sequence
<220> FEATURE:
<223> OTHER INFORMATION: HCDR2 of Family 19a clone 185

<400> SEQUENCE: 45

Val Ile Ser His Ser Gly Gly Trp Ile Asn Tyr Ala Asp Ser Val Lys
1               5                   10                  15

Gly

<210> SEQ ID NO 46
<211> LENGTH: 17
<212> TYPE: PRT
<213> ORGANISM: Artificial Sequence
<220> FEATURE:
<223> OTHER INFORMATION: Consensus HCDR2 of Family 19a, Formula VI
<220> FEATURE:
<221> NAME/KEY: VARIANT
<222> LOCATION: 1
<223> OTHER INFORMATION: Xaa may be Ala, Gly, Thr or Val
<220> FEATURE:
<221> NAME/KEY: VARIANT
<222> LOCATION: 3
<223> OTHER INFORMATION: Xaa may be Asn or Ser
<220> FEATURE:
<221> NAME/KEY: VARIANT
<222> LOCATION: 4
<223> OTHER INFORMATION: Xaa may be Gly, Met, Lys, Ile, Leu or His
<220> FEATURE:
<221> NAME/KEY: VARIANT
<222> LOCATION: 5
<223> OTHER INFORMATION: Xaa may be Leu, Asp, Ala, His, Thr, Gly or Ser
```

```
<220> FEATURE:
<221> NAME/KEY: VARIANT
<222> LOCATION: 6
<223> OTHER INFORMATION: Xaa may be Gly or Ser
<220> FEATURE:
<221> NAME/KEY: VARIANT
<222> LOCATION: 7
<223> OTHER INFORMATION: Xaa may be Thr, Gly, Tyr or Asp
<220> FEATURE:
<221> NAME/KEY: VARIANT
<222> LOCATION: 8
<223> OTHER INFORMATION: Xaa may be His, Trp, Tyr or Phe
<220> FEATURE:
<221> NAME/KEY: VARIANT
<222> LOCATION: 9
<223> OTHER INFORMATION: Xaa may be Lys, Thr or Ile
<220> FEATURE:
<221> NAME/KEY: VARIANT
<222> LOCATION: 10
<223> OTHER INFORMATION: Xaa may be Tyr, Phe or Asn

<400> SEQUENCE: 46

Xaa Ile Xaa Xaa Xaa Xaa Xaa Xaa Xaa Xaa Tyr Ala Asp Ser Val Lys
 1               5                   10                  15

Gly

<210> SEQ ID NO 47
<211> LENGTH: 16
<212> TYPE: PRT
<213> ORGANISM: Artificial Sequence
<220> FEATURE:
<223> OTHER INFORMATION: HCDR2 of Family 19b clone 186

<400> SEQUENCE: 47

Val Thr Ser Ala Asn Gly Arg Thr Tyr Tyr Ala Asp Ser Val Lys Gly
 1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: HCDR2 of Family 19b clone 187

<400> SEQUENCE: 48

Val Thr Ser Lys Met Gly His Thr Tyr Tyr Ala Asp Ser Val Lys Gly
 1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: HCDR2 of Family 19b clone 188

<400> SEQUENCE: 49

Val Thr Ser Met Thr Gly Asn Thr Tyr Tyr Ala Asp Ser Val Lys Gly
 1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: HCDR2 of Family 19b clone 189

<400> SEQUENCE: 50

Val Thr Ser His Arg Asp Asn Thr Tyr Tyr Ala Gly Ser Val Lys Gly
 1               5                   10                  15
```

```
<210> SEQ ID NO 51
<211> LENGTH: 16
<212> TYPE: PRT
<213> ORGANISM: Artificial Sequence
<220> FEATURE:
<223> OTHER INFORMATION: Consensus HCDR2 of Family 19b, Formula VIII
<220> FEATURE:
<221> NAME/KEY: VARIANT
<222> LOCATION: 4
<223> OTHER INFORMATION: Xaa may be Ala, Lys, Met or His
<220> FEATURE:
<221> NAME/KEY: VARIANT
<222> LOCATION: 5
<223> OTHER INFORMATION: Xaa may be Asn, Met, Thr or Arg
<220> FEATURE:
<221> NAME/KEY: VARIANT
<222> LOCATION: 6
<223> OTHER INFORMATION: Xaa may be Gly or Asp
<220> FEATURE:
<221> NAME/KEY: VARIANT
<222> LOCATION: 7
<223> OTHER INFORMATION: Xaa may be Arg, His or Asn
<220> FEATURE:
<221> NAME/KEY: VARIANT
<222> LOCATION: 12
<223> OTHER INFORMATION: Xaa may be Asp or Gly

<400> SEQUENCE: 51

Val Thr Ser Xaa Xaa Xaa Xaa Thr Tyr Tyr Ala Xaa Ser Val Lys Gly
 1               5                  10                  15

<210> SEQ ID NO 52
<211> LENGTH: 8
<212> TYPE: PRT
<213> ORGANISM: Artificial Sequence
<220> FEATURE:
<223> OTHER INFORMATION: HCDR3 of Family 2

<400> SEQUENCE: 52

Asp Ser Glu Tyr Tyr Phe Asp His
 1               5

<210> SEQ ID NO 53
<211> LENGTH: 12
<212> TYPE: PRT
<213> ORGANISM: Artificial Sequence
<220> FEATURE:
<223> OTHER INFORMATION: HCDR3 of Family 6a, 6b clones 13, 15, 16, Mor
      7706, 7775

<400> SEQUENCE: 53

Glu Val Asp Ser Met Tyr Tyr Ser Tyr Phe Asp Ile
 1               5                  10

<210> SEQ ID NO 54
<211> LENGTH: 12
<212> TYPE: PRT
<213> ORGANISM: Artificial Sequence
<220> FEATURE:
<223> OTHER INFORMATION: HCDR3 of Family 6b MOR 8299, 8101

<400> SEQUENCE: 54

Glu Val Asp Ser Ile Tyr Tyr Ser Tyr Phe Asp Ile
 1               5                  10

<210> SEQ ID NO 55
<211> LENGTH: 12
<212> TYPE: PRT
<213> ORGANISM: Artificial Sequence
<220> FEATURE:
<223> OTHER INFORMATION: HCDR3 of Family 6b MOR 8300, 8102
```

```
<400> SEQUENCE: 55

Glu Val Asp Ser Leu Tyr Tyr Ser Tyr Phe Asp Ile
1               5                   10

<210> SEQ ID NO 56
<211> LENGTH: 12
<212> TYPE: PRT
<213> ORGANISM: Artificial Sequence
<220> FEATURE:
<223> OTHER INFORMATION: HCDR3 of Family 6b MOR 8301, 8103

<400> SEQUENCE: 56

Glu Val Asp Ser Thr Tyr Tyr Ser Tyr Phe Asp Ile
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Consensus HCDR3 of Family 6b, Formula IV
<220> FEATURE:
<221> NAME/KEY: VARIANT
<222> LOCATION: 5
<223> OTHER INFORMATION: Xaa may be Met, Ile, Leu or Thr

<400> SEQUENCE: 57

Glu Val Asp Ser Xaa Tyr Tyr Ser Tyr Phe Asp Ile
1               5                   10

<210> SEQ ID NO 58
<211> LENGTH: 6
<212> TYPE: PRT
<213> ORGANISM: Artificial Sequence
<220> FEATURE:
<223> OTHER INFORMATION: HCDR3 of Family 19a clone  179, 180, 182, MOR
      7709, 7700, 8095, 8096, 8141, 8142, 8143, 7768,
      Family 19b

<400> SEQUENCE: 58

Gln Leu Met Leu Asp Val
1               5

<210> SEQ ID NO 59
<211> LENGTH: 6
<212> TYPE: PRT
<213> ORGANISM: Artificial Sequence
<220> FEATURE:
<223> OTHER INFORMATION: HCDR3 of Family 19a MOR 8097

<400> SEQUENCE: 59

Gln Leu Leu Leu Asp Val
1               5

<210> SEQ ID NO 60
<211> LENGTH: 6
<212> TYPE: PRT
<213> ORGANISM: Artificial Sequence
<220> FEATURE:
<223> OTHER INFORMATION: HCDR3 of Family 19a MOR 8098, 8160, 8161, 8162,
      8302, 8303, mAb5548

<400> SEQUENCE: 60

Gln Leu Thr Leu Asp Val
1               5

<210> SEQ ID NO 61
```

```
<211> LENGTH: 6
<212> TYPE: PRT
<213> ORGANISM: Artificial Sequence
<220> FEATURE:
<223> OTHER INFORMATION: Consensus HCDR3 of Family 19a, Formula VII
<220> FEATURE:
<221> NAME/KEY: VARIANT
<222> LOCATION: 3
<223> OTHER INFORMATION: Xaa may be Met, Leu or Thr

<400> SEQUENCE: 61

Gln Leu Xaa Leu Asp Val
 1               5

<210> SEQ ID NO 62
<211> LENGTH: 106
<212> TYPE: PRT
<213> ORGANISM: Artificial Sequence
<220> FEATURE:
<223> OTHER INFORMATION: VL or Family 2

<400> SEQUENCE: 62

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Trp
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Tyr Ser Asp Asp Pro Thr
                 85                  90                  95

Phe Gly Gln Gly Thr Lys Val Glu Ile Lys
            100                 105

<210> SEQ ID NO 63
<211> LENGTH: 109
<212> TYPE: PRT
<213> ORGANISM: Artificial Sequence
<220> FEATURE:
<223> OTHER INFORMATION: VL or Family 6b MOR 7706, 8299, 8300, 8301

<400> SEQUENCE: 63

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Asn Val Trp Ala Phe
             20                  25                  30

Tyr Leu Ala Trp Tyr Gln Gln Lys Pro Gly Gln Ala Pro Arg Leu Leu
         35                  40                  45

Ile Tyr Gly Ala Ser Asn Arg Ala Thr Gly Val Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Gln Gln Tyr Arg Ser Thr Leu
                 85                  90                  95

Ser Leu Thr Phe Gly Gln Gly Thr Lys Val Glu Ile Lys
            100                 105

<210> SEQ ID NO 64
<211> LENGTH: 109
```

```
<212> TYPE: PRT
<213> ORGANISM: Artificial Sequence
<220> FEATURE:
<223> OTHER INFORMATION: VL of Family 6b MOR 7775, 8010, 8102, 8103

<400> SEQUENCE: 64

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Asn Val Trp Ala Phe
             20                  25                  30

Tyr Leu Ala Trp Tyr Gln Gln Lys Pro Gly Gln Ala Pro Arg Leu Leu
         35                  40                  45

Ile Tyr Gly Ala Ser Asn Arg Ala Thr Gly Val Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Thr Tyr Tyr Cys Thr Gln Tyr Tyr Ser Ser Pro
                 85                  90                  95

Ser Leu Thr Phe Gly Gln Gly Thr Lys Val Glu Ile Lys
            100                 105

<210> SEQ ID NO 65
<211> LENGTH: 108
<212> TYPE: PRT
<213> ORGANISM: Artificial Sequence
<220> FEATURE:
<223> OTHER INFORMATION: VL or family 19a clone 179, 180, 182, MOR 7709,
      7700, 8095, 8096, 8097, 8098, 8302, 7768, Family
      19b

<400> SEQUENCE: 65

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Gly Asp Lys Tyr Ala
             20                  25                  30

Asn Trp Tyr Gln Gln Lys Pro Gly Gln Ala Pro Val Leu Val Ile Tyr
         35                  40                  45

Asp Asp Ile Asp Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gly Ser Tyr Asp Phe Phe Leu Gly Met
                 85                  90                  95

Ile Val Phe Gly Gly Gly Thr Lys Leu Thr Val Leu
            100                 105

<210> SEQ ID NO 66
<211> LENGTH: 108
<212> TYPE: PRT
<213> ORGANISM: Artificial Sequence
<220> FEATURE:
<223> OTHER INFORMATION: VL or Family 19a MOR 8016, mAb 5548

<400> SEQUENCE: 66

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Gly Asp Lys Tyr Ala
             20                  25                  30

Asn Trp Tyr Gln Gln Lys Pro Gly Gln Ala Pro Val Leu Val Ile Tyr
         35                  40                  45
```

-continued

```
Asp Asp Ile Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gly Ser Tyr Asp Phe Phe Leu Gly Leu
                 85                  90                  95

Ile Val Phe Gly Gly Gly Thr Lys Leu Thr Val Leu
                100                 105

<210> SEQ ID NO 67
<211> LENGTH: 117
<212> TYPE: PRT
<213> ORGANISM: Artificial Sequence
<220> FEATURE:
<223> OTHER INFORMATION: VH or Family 2 MOR 7708

<400> SEQUENCE: 67

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Arg Ile Ile Pro Trp Phe Gly Trp Thr Ser Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ser Glu Tyr Tyr Phe Asp His Trp Gly Gln Gly Thr Leu
                100                 105                 110

Val Thr Val Ser Ser
            115

<210> SEQ ID NO 68
<211> LENGTH: 117
<212> TYPE: PRT
<213> ORGANISM: Artificial Sequence
<220> FEATURE:
<223> OTHER INFORMATION: VH or Family 2 MOR 7785

<400> SEQUENCE: 68

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Ser Ile Ile Pro Trp Phe Gly Trp Thr Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ser Glu Tyr Tyr Phe Asp His Trp Gly Gln Gly Thr Leu
                100                 105                 110

Val Thr Val Ser Ser
            115
```

-continued

```
<210> SEQ ID NO 69
<211> LENGTH: 117
<212> TYPE: PRT
<213> ORGANISM: Artificial Sequence
<220> FEATURE:
<223> OTHER INFORMATION: VH or Family 2 MOR 8104

<400> SEQUENCE: 69

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Ser Ile Ile Pro Trp Phe Gly Thr Thr Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Ser Glu Tyr Tyr Phe Asp His Trp Gly Gln Gly Thr Leu
            100                 105                 110

Val Thr Val Ser Ser
        115

<210> SEQ ID NO 70
<211> LENGTH: 124
<212> TYPE: PRT
<213> ORGANISM: Artificial Sequence
<220> FEATURE:
<223> OTHER INFORMATION: VH or Family 6b MOR 7706, 7775

<400> SEQUENCE: 70

Gln Val Gln Leu Gln Ser Gly Pro Gly Leu Val Lys Pro Ser Gln
  1               5                  10                  15

Thr Leu Ser Leu Thr Cys Ala Ile Ser Gly Asp Ser Val Ser Ser
             20                  25                  30

Ser Ala Ala Trp Gly Trp Ile Arg Gln Ser Pro Gly Arg Gly Leu Glu
         35                  40                  45

Trp Leu Gly Arg Ile Ser Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Glu Val Asp Ser Met Tyr Tyr Ser Tyr Phe Asp
            100                 105                 110

Ile Trp Gly Gln Gly Thr Leu Val Thr Val Ser Ser
        115                 120

<210> SEQ ID NO 71
<211> LENGTH: 124
<212> TYPE: PRT
<213> ORGANISM: Artificial Sequence
<220> FEATURE:
<223> OTHER INFORMATION: VH or Family 6b MOR 8299, 8101

<400> SEQUENCE: 71

Gln Val Gln Leu Gln Ser Gly Pro Gly Leu Val Lys Pro Ser Gln
  1               5                  10                  15
```

```
Thr Leu Ser Leu Thr Cys Ala Ile Ser Gly Asp Ser Val Ser Ser
            20                  25                  30

Ser Ala Ala Trp Gly Trp Ile Arg Gln Ser Pro Gly Arg Gly Leu Glu
        35                  40                  45

Trp Leu Gly Arg Ile Ser Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Asp Ser Ile Tyr Tyr Ser Tyr Phe Asp
            100                 105                 110

Ile Trp Gly Gln Gly Thr Leu Val Thr Val Ser Ser
        115                 120

<210> SEQ ID NO 72
<211> LENGTH: 124
<212> TYPE: PRT
<213> ORGANISM: Artificial Sequence
<220> FEATURE:
<223> OTHER INFORMATION: VH or Family 6b MOR 8103, 8301

<400> SEQUENCE: 72

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser
            20                  25                  30

Ser Ala Ala Trp Gly Trp Ile Arg Gln Ser Pro Gly Arg Gly Leu Glu
        35                  40                  45

Trp Leu Gly Arg Ile Ser Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Asp Ser Thr Tyr Tyr Ser Tyr Phe Asp
            100                 105                 110

Ile Trp Gly Gln Gly Thr Leu Val Thr Val Ser Ser
        115                 120

<210> SEQ ID NO 73
<211> LENGTH: 115
<212> TYPE: PRT
<213> ORGANISM: Artificial Sequence
<220> FEATURE:
<223> OTHER INFORMATION: VH or Family 19a MOR 7700, 8141, 8142, 8143

<400> SEQUENCE: 73

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Met Thr Ser Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

Leu Gln Met Asn Ser Leu Arg Ala Glu Asp Thr Ala Val Tyr Tyr Cys
                85                  90                  95

Ala Arg Gln Leu Met Leu Asp Val Trp Gly Gln Gly Thr Leu Val Thr
            100                 105                 110

Val Ser Ser
        115

<210> SEQ ID NO 74
<211> LENGTH: 115
<212> TYPE: PRT
<213> ORGANISM: Artificial Sequence
<220> FEATURE:
<223> OTHER INFORMATION: VH or Family 19a MOR 8096, 8160, 8161, 8162

<400> SEQUENCE: 74

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Met Thr Ser Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Thr Leu Asp Val Trp Gly Gln Gly Thr Leu Val Thr
            100                 105                 110

Val Ser Ser
        115

<210> SEQ ID NO 75
<211> LENGTH: 115
<212> TYPE: PRT
<213> ORGANISM: Artificial Sequence
<220> FEATURE:
<223> OTHER INFORMATION: VH or Family 19a MOR 8302, 8303, mAb 5548

<400> SEQUENCE: 75

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Leu Thr Ser Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Thr Leu Asp Val Trp Gly Gln Gly Thr Leu Val Thr
            100                 105                 110

Val Ser Ser
        115

<210> SEQ ID NO 76

```
<211> LENGTH: 106
<212> TYPE: PRT
<213> ORGANISM: Artificial Sequence
<220> FEATURE:
<223> OTHER INFORMATION: VL or Family 2 mAbs

<400> SEQUENCE: 76

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Asp Asp Pro Thr
                85                  90                  95

Phe Gly Gln Gly Thr Lys Val Glu Ile Lys
            100                 105

<210> SEQ ID NO 77
<211> LENGTH: 109
<212> TYPE: PRT
<213> ORGANISM: Artificial Sequence
<220> FEATURE:
<223> OTHER INFORMATION: VL or Family 6b mAbs 4538, 3584

<400> SEQUENCE: 77

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Val Trp Ala Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Arg Ser Thr Leu
                85                  90                  95

Ser Leu Thr Phe Gly Gln Gly Thr Lys Val Glu Ile Lys
            100                 105

<210> SEQ ID NO 78
<211> LENGTH: 109
<212> TYPE: PRT
<213> ORGANISM: Artificial Sequence
<220> FEATURE:
<223> OTHER INFORMATION: VL of Family 6b mAbs 732, 4168

<400> SEQUENCE: 78

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Val Trp Ala Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Ala Arg Phe Ser
```

```
                    50                  55                  60
Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Thr Gln Tyr Tyr Ser Ser Pro
                 85                  90                  95

Ser Leu Thr Phe Gly Gln Gly Thr Lys Val Glu Ile Lys
            100                 105
```

<210> SEQ ID NO 79
<211> LENGTH: 108
<212> TYPE: PRT
<213> ORGANISM: Artificial Sequence
<220> FEATURE:
<223> OTHER INFORMATION: VL or family 19a mAbs 1926, 6785, Family 19b

<400> SEQUENCE: 79

```
Gln Ser Val Leu Thr Gln Pro Pro Ser Val Ser Val Ala Pro Gly Gln
  1               5                  10                  15

Thr Ala Arg Ile Ser Cys Ser Gly Asp Asn Leu Gly Asp Lys Tyr Ala
             20                  25                  30

Asn Trp Tyr Gln Gln Lys Pro Gly Gln Ala Pro Val Leu Val Ile Tyr
         35                  40                  45

Asp Asp Ile Asp Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gly Ser Tyr Asp Phe Phe Leu Gly Met
                 85                  90                  95

Ile Val Phe Gly Gly Gly Thr Lys Leu Thr Val Leu
            100                 105
```

<210> SEQ ID NO 80
<211> LENGTH: 108
<212> TYPE: PRT
<213> ORGANISM: Artificial Sequence
<220> FEATURE:
<223> OTHER INFORMATION: VL or Family 19a mAbs 7146, 5584

<400> SEQUENCE: 80

```
Gln Ser Val Leu Thr Gln Pro Pro Ser Val Ser Val Ala Pro Gly Gln
  1               5                  10                  15

Thr Ala Arg Ile Ser Cys Ser Gly Asp Asn Leu Gly Asp Lys Tyr Ala
             20                  25                  30

Asn Trp Tyr Gln Gln Lys Pro Gly Gln Ala Pro Val Leu Val Ile Tyr
         35                  40                  45

Asp Asp Ile Asp Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gly Ser Tyr Asp Phe Phe Leu Gly Leu
                 85                  90                  95

Ile Val Phe Gly Gly Gly Thr Lys Leu Thr Val Leu
            100                 105
```

<210> SEQ ID NO 81
<211> LENGTH: 124
<212> TYPE: PRT
<213> ORGANISM: Artificial Sequence
<220> FEATURE:
<223> OTHER INFORMATION: VH or Family 6b mAb 4583, 732

<400> SEQUENCE: 81

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Ser
            20                  25                  30

Ser Ala Ala Trp Gly Trp Ile Arg Gln Ser Pro Ser Arg Gly Leu Glu
        35                  40                  45

Trp Leu Gly Arg Ile Ser Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Asp Ser Met Tyr Tyr Ser Tyr Phe Asp
            100                 105                 110

Ile Trp Gly Gln Gly Thr Leu Val Thr Val Ser Ser
        115                 120

<210> SEQ ID NO 82
<211> LENGTH: 123
<212> TYPE: PRT
<213> ORGANISM: Artificial Sequence
<220> FEATURE:
<223> OTHER INFORMATION: VH or Family 6b mAb 3584

<400> SEQUENCE: 82

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Ser
            20                  25                  30

Ser Ala Ala Trp Gly Trp Ile Arg Gln Ser Pro Arg Gly Leu Glu Trp
        35                  40                  45

Leu Gly Arg Ile Ser Tyr Arg Ser Lys Trp Tyr Asn Asp Tyr Ala Val
    50                  55                  60

Ser Val Lys Ser Arg Ile Thr Ile Asn Pro Asp Thr Ser Lys Asn Gln
65                  70                  75                  80

Phe Ser Leu Gln Leu Asn Ser Val Thr Pro Glu Asp Thr Ala Val Tyr
                85                  90                  95

Tyr Cys Ala Arg Glu Val Asp Ser Ile Tyr Tyr Ser Tyr Phe Asp Ile
            100                 105                 110

Trp Gly Gln Gly Thr Leu Val Thr Val Ser Ser
        115                 120

<210> SEQ ID NO 83
<211> LENGTH: 123
<212> TYPE: PRT
<213> ORGANISM: Artificial Sequence
<220> FEATURE:
<223> OTHER INFORMATION: VH or Family 6b mAb 4168

<400> SEQUENCE: 83

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Ser
            20                  25                  30

Ser Ala Ala Trp Gly Trp Ile Arg Gln Ser Pro Arg Gly Leu Glu Trp
        35                  40                  45

-continued

```
Leu Gly Arg Ile Ser Tyr Arg Ser Lys Trp Tyr Asn Asp Tyr Ala Val
    50                  55                  60

Ser Val Lys Ser Arg Ile Thr Ile Asn Pro Asp Thr Ser Lys Asn Gln
65                  70                  75                  80

Phe Ser Leu Gln Leu Asn Ser Val Thr Pro Glu Asp Thr Ala Val Tyr
                85                  90                  95

Tyr Cys Ala Arg Glu Val Asp Ser Thr Tyr Tyr Ser Tyr Phe Asp Ile
            100                 105                 110

Trp Gly Gln Gly Thr Leu Val Thr Val Ser Ser
        115                 120
```

<210> SEQ ID NO 84
<211> LENGTH: 115
<212> TYPE: PRT
<213> ORGANISM: Artificial Sequence
<220> FEATURE:
<223> OTHER INFORMATION: VH or Family 19a mAb 1926

<400> SEQUENCE: 84

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Met Thr Ser Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Met Leu Asp Val Trp Gly Gln Gly Thr Leu Val Thr
            100                 105                 110

Val Ser Ser
        115
```

<210> SEQ ID NO 85
<211> LENGTH: 115
<212> TYPE: PRT
<213> ORGANISM: Artificial Sequence
<220> FEATURE:
<223> OTHER INFORMATION: VH or Family 19a mAb 7146

<400> SEQUENCE: 85

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Met Thr Ser Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Thr Leu Asp Val Trp Gly Gln Gly Thr Leu Val Thr
            100                 105                 110
```

-continued

Val Ser Ser
    115

<210> SEQ ID NO 86
<211> LENGTH: 115
<212> TYPE: PRT
<213> ORGANISM: Artificial Sequence
<220> FEATURE:
<223> OTHER INFORMATION: VH or Family 19a mAb 6785, 5548

<400> SEQUENCE: 86

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Leu Thr Ser Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Thr Leu Asp Val Trp Gly Gln Gly Thr Leu Val Thr
            100                 105                 110

Val Ser Ser
    115

<210> SEQ ID NO 87
<211> LENGTH: 212
<212> TYPE: PRT
<213> ORGANISM: Artificial Sequence
<220> FEATURE:
<223> OTHER INFORMATION: Light chain of mAb 624, 3077, 7024 Family 2

<400> SEQUENCE: 87

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Asp Asp Pro Thr
                85                  90                  95

Phe Gly Gln Gly Thr Lys Val Glu Ile Lys Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
                180                 185                 190

Cys Gln Val Thr His Glu Gly Ser Thr Val Glu Lys Thr Val Ala Pro
            195                 200                 205

Thr Glu Cys Ser
        210

<210> SEQ ID NO 88
<211> LENGTH: 215
<212> TYPE: PRT
<213> ORGANISM: Artificial Sequence
<220> FEATURE:
<223> OTHER INFORMATION: Light chain of mAb Family 6b mAb 4538, 3584

<400> SEQUENCE: 88

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Val Trp Ala Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Arg Ser Thr Leu
                85                  90                  95

Ser Leu Thr Phe Gly Gln Gly Thr Lys Val Glu Ile Lys Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 89
<211> LENGTH: 215
<212> TYPE: PRT
<213> ORGANISM: Artificial Sequence
<220> FEATURE:
<223> OTHER INFORMATION: Light chain of mAb Family 6b mAb 732, 4168

<400> SEQUENCE: 89

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Val Trp Ala Phe
            20                  25                  30

Tyr Leu Ala Trp Tyr Gln Gln Lys Pro Gly Gln Ala Pro Arg Leu Leu
        35                  40                  45

```
Ile Tyr Gly Ala Ser Asn Arg Ala Thr Gly Ile Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Thr Gln Tyr Tyr Ser Ser Pro
                 85                  90                  95

Ser Leu Thr Phe Gly Gln Gly Thr Lys Val Glu Ile Lys Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
        210                 215

<210> SEQ ID NO 90
<211> LENGTH: 214
<212> TYPE: PRT
<213> ORGANISM: Artificial Sequence
<220> FEATURE:
<223> OTHER INFORMATION: Light chain of mAb Family 19a mAb 1926, 6785

<400> SEQUENCE: 90

Gln Ser Val Leu Thr Gln Pro Pro Ser Val Ser Val Ala Pro Gly Gln
 1               5                  10                  15

Thr Ala Arg Ile Ser Cys Ser Gly Asp Asn Leu Gly Asp Lys Tyr Ala
             20                  25                  30

Asn Trp Tyr Gln Gln Lys Pro Gly Gln Ala Pro Val Leu Val Ile Tyr
         35                  40                  45

Asp Asp Ile Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gly Ser Tyr Asp Phe Phe Leu Gly Met
                 85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
```

Ala Pro Thr Glu Cys Ser
    210

<210> SEQ ID NO 91
<211> LENGTH: 214
<212> TYPE: PRT
<213> ORGANISM: Artificial Sequence
<220> FEATURE:
<223> OTHER INFORMATION: Light chain of mAb Family 19a mAb 7146, 5548

<400> SEQUENCE: 91

Gln Ser Val Leu Thr Gln Pro Pro Ser Val Ser Val Ala Pro Gly Gln
 1               5                  10                  15

Thr Ala Arg Ile Ser Cys Ser Gly Asp Asn Leu Gly Asp Lys Tyr Ala
            20                  25                  30

Asn Trp Tyr Gln Gln Lys Pro Gly Gln Ala Pro Val Leu Val Ile Tyr
        35                  40                  45

Asp Asp Ile Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Ser Tyr Asp Phe Phe Leu Gly Leu
                85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 92
<211> LENGTH: 447
<212> TYPE: PRT
<213> ORGANISM: Artificial Sequence
<220> FEATURE:
<223> OTHER INFORMATION: Heavy chain of Family 2 mAb 624

<400> SEQUENCE: 92

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Trp Phe Gly Trp Thr Ser Tyr Ala Gln Lys Phe
    50                  55                  60

Gln Gly Arg Val Thr Ile Thr Ala Asp Glu Ser Thr Ser Thr Ala Tyr

```
                65                  70                  75                  80
            Met Glu Leu Ser Ser Leu Arg Ser Glu Asp Thr Ala Val Tyr Tyr Cys
                                85                  90                  95

Ala Arg Asp Ser Glu Tyr Tyr Phe Asp His Trp Gly Gln Gly Thr Leu
                            100                 105                 110

Val Thr Val Ser Ser Ala Ser Thr Lys Gly Pro Ser Val Phe Pro Leu
                        115                 120                 125

Ala Pro Ser Ser Lys Ser Thr Ser Gly Gly Thr Ala Ala Leu Gly Cys
                    130                 135                 140

Leu Val Lys Asp Tyr Phe Pro Glu Pro Val Thr Val Ser Trp Asn Ser
            145                 150                 155                 160

Gly Ala Leu Thr Ser Gly Val His Thr Phe Pro Ala Val Leu Gln Ser
                            165                 170                 175

Ser Gly Leu Tyr Ser Leu Ser Ser Val Val Thr Val Pro Ser Ser Ser
                        180                 185                 190

Leu Gly Thr Gln Thr Tyr Ile Cys Asn Val Asn His Lys Pro Ser Asn
                    195                 200                 205

Thr Lys Val Asp Lys Lys Val Glu Pro Lys Ser Cys Asp Lys Thr His
                210                 215                 220

Thr Cys Pro Pro Cys Pro Ala Pro Glu Leu Leu Gly Gly Pro Ser Val
            225                 230                 235                 240

Phe Leu Phe Pro Pro Lys Pro Lys Asp Thr Leu Met Ile Ser Arg Thr
                            245                 250                 255

Pro Glu Val Thr Cys Val Val Val Asp Val Ser His Glu Asp Pro Glu
                        260                 265                 270

Val Lys Phe Asn Trp Tyr Val Asp Gly Val Glu Val His Asn Ala Lys
                    275                 280                 285

Thr Lys Pro Arg Glu Glu Gln Tyr Asn Ser Thr Tyr Arg Val Val Ser
                290                 295                 300

Val Leu Thr Val Leu His Gln Asp Trp Leu Asn Gly Lys Glu Tyr Lys
            305                 310                 315                 320

Cys Lys Val Ser Asn Lys Ala Leu Pro Ala Pro Ile Glu Lys Thr Ile
                            325                 330                 335

Ser Lys Ala Lys Gly Gln Pro Arg Glu Pro Gln Val Tyr Thr Leu Pro
                        340                 345                 350

Pro Ser Arg Asp Glu Leu Thr Lys Asn Gln Val Ser Leu Thr Cys Leu
                    355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
            385                 390                 395                 400

Asp Gly Ser Phe Phe Leu Tyr Ser Lys Leu Thr Val Asp Lys Ser Arg
                            405                 410                 415

Trp Gln Gln Gly Asn Val Phe Ser Cys Ser Val Met His Glu Ala Leu
                        420                 425                 430

His Asn His Tyr Thr Gln Lys Ser Leu Ser Leu Ser Pro Gly Lys
                    435                 440                 445

<210> SEQ ID NO 93
<211> LENGTH: 447
<212> TYPE: PRT
<213> ORGANISM: Artificial Sequence
<220> FEATURE:
<223> OTHER INFORMATION: Heavy chain of Family 2 mAb 3077

<400> SEQUENCE: 93
```

```
Gln Val Gln Leu Val Gln Ser Gly Ala Glu Val Lys Lys Pro Gly Ser
 1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Ser Ile Ile Pro Trp Phe Gly Trp Thr Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Ser Glu Tyr Tyr Phe Asp His Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
```

His Asn His Tyr Thr Gln Lys Ser Leu Ser Leu Ser Pro Gly Lys
            435                 440                 445

<210> SEQ ID NO 94
<211> LENGTH: 447
<212> TYPE: PRT
<213> ORGANISM: Artificial Sequence
<220> FEATURE:
<223> OTHER INFORMATION: Heavy chain of Family 2 mAb 7024

<400> SEQUENCE: 94

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Trp Phe Gly Thr Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Glu Tyr Tyr Phe Asp His Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

```
Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 95
<211> LENGTH: 454
<212> TYPE: PRT
<213> ORGANISM: Artificial Sequence
<220> FEATURE:
<223> OTHER INFORMATION: Heavy chain of Family 6b mAb 4538, 732

<400> SEQUENCE: 95

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Ser
                20                  25                  30

Ser Ala Ala Trp Gly Trp Ile Arg Gln Ser Pro Ser Arg Gly Leu Glu
                35                  40                  45

Trp Leu Gly Arg Ile Ser Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Asp Ser Met Tyr Tyr Ser Tyr Phe Asp
                100                 105                 110

Ile Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Lys Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270
```

```
Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
450

<210> SEQ ID NO 96
<211> LENGTH: 454
<212> TYPE: PRT
<213> ORGANISM: Artificial Sequence
<220> FEATURE:
<223> OTHER INFORMATION: Heavy chain of Family 6b mAb 3584

<400> SEQUENCE: 96

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Ser
            20                  25                  30

Ser Ala Ala Trp Gly Trp Ile Arg Gln Ser Pro Ser Arg Gly Leu Glu
        35                  40                  45

Trp Leu Gly Arg Ile Ser Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Asp Ser Ile Tyr Tyr Ser Tyr Phe Asp
            100                 105                 110

Ile Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
```

```
                    180                 185                 190
Val Thr Val Pro Ser Ser Leu Gly Thr Gln Thr Tyr Ile Cys Asn
            195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 97
<211> LENGTH: 454
<212> TYPE: PRT
<213> ORGANISM: Artificial Sequence
<220> FEATURE:
<223> OTHER INFORMATION: Heavy chain of Family 6b mAb 4168

<400> SEQUENCE: 97

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Ser
            20                  25                  30

Ser Ala Ala Trp Gly Trp Ile Arg Gln Ser Pro Ser Arg Gly Leu Glu
        35                  40                  45

Trp Leu Gly Arg Ile Ser Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95
```

Tyr Tyr Cys Ala Arg Glu Val Asp Ser Thr Tyr Tyr Ser Tyr Phe Asp
            100                 105                 110

Ile Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 98
<211> LENGTH: 445
<212> TYPE: PRT
<213> ORGANISM: Artificial Sequence
<220> FEATURE:
<223> OTHER INFORMATION: Heavy chain of Family 19a mAb 1926

<400> SEQUENCE: 98

-continued

```
Gln Val Gln Leu Leu Glu Ser Gly Gly Gly Leu Val Gln Pro Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Met Thr Ser Gly Phe Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gln Leu Met Leu Asp Val Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430
```

His Tyr Thr Gln Lys Ser Leu Ser Leu Ser Pro Gly Lys
        435                 440                 445

<210> SEQ ID NO 99
<211> LENGTH: 445
<212> TYPE: PRT
<213> ORGANISM: Artificial Sequence
<220> FEATURE:
<223> OTHER INFORMATION: Heavy chain of Family 19a mAb 7146

<400> SEQUENCE: 99

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Met Thr Ser Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Thr Leu Asp Val Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

-continued

```
Arg Asp Glu Leu Thr Lys Asn Gln Val Ser Leu Thr Cys Leu Val Lys
            355                 360                 365
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 100
<211> LENGTH: 445
<212> TYPE: PRT
<213> ORGANISM: Artificial Sequence
<220> FEATURE:
<223> OTHER INFORMATION: Heavy chain of mAb family 19a mAb 6785, 5548

<400> SEQUENCE: 100

Gln Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Thr Ile Ser Leu Thr Ser Gly Phe Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gln Leu Thr Leu Asp Val Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
```

```
          275                 280                 285
Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 101
<211> LENGTH: 1392
<212> TYPE: DNA
<213> ORGANISM: Artificial Sequence
<220> FEATURE:
<223> OTHER INFORMATION: cDNA codon optimized mAb 6785 heavy chain with
      leader sequence

<400> SEQUENCE: 101
atggcttggg tgtggacctt gctattcctg atggcagctg cccaaagtat acaggcccaa      60
gtgcagctgc tggagagcgg cggcggcctg gtgcagcccg gcggcagcct gcggctgagc     120
tgcgccgcca gcggcttcac cttcagcagc tacgccatga gctgggtgcg gcaggccccc     180
ggcaagggcc tggagtgggt gagcaccatc agcctgacca gcggcttcac ctactacgcc     240
gacagcgtga agggccggtt caccatcagc cgggacaaca gcaagaacac cctgtacctg     300
cagatgaaca gcctgcgggc cgaggacacc gccgtgtact actgcgcccg gcagctgacc     360
ctggacgtgt ggggccaggg caccctggtg accgtgagca gcgcctccac caagggccca     420
tcggtcttcc ccctggcacc ctcctccaag agcacctctg ggggcacagc ggccctgggc     480
tgcctggtca aggactactt ccccgaaccg gtgacggtgt cgtggaactc aggcgccctg     540
accagcggcg tgcacacctt cccggctgtc ctacagtcct caggactcta ctccctcagc     600
agcgtggtga ccgtgccctc cagcagcttg ggcacccaga cctacatctg caacgtgaat     660
cacaagccca gcaacaccaa ggtggacaag aaagttgagc ccaaatcttg tgacaaaact     720
cacacatgcc caccgtgccc agcacctgaa ctcctggggg gaccgtcagt cttcctcttc     780 ccccccaaaac ccaaggacac cctcatgatc tcccggaccc ctgaggtcac atgcgtggtg     840
gtggacgtga gccacgaaga ccctgaggtc aagttcaact ggtacgtgga cggcgtggag     900
gtgcataatg ccaagacaaa gccgcgggag gagcagtaca acagcacgta ccgtgtggtc     960
agcgtcctca ccgtcctgca ccaggactgg ctgaatggca aggagtacaa gtgcaaggtc    1020
tccaacaaag ccctcccagc ccccatcgag aaaaccatct ccaaagccaa agggcagccc    1080
cgagaaccac aggtgtacac cctgccccca tcccgggatg agctgaccaa gaaccaggtc    1140
```

-continued

| | |
|---|---|
| agcctgacct gcctggtcaa aggcttctat cccagcgaca tcgccgtgga gtgggagagc | 1200 |
| aatgggcagc ggagaacaa ctacaagacc acgcctccg tgctggactc cgacggctcc | 1260 |
| ttcttcctct acagcaagct caccgtggac aagagcaggt ggcagcaggg gaacgtcttc | 1320 |
| tcatgctccg tgatgcatga ggctctgcac aaccactaca cgcagaagag cctctccctg | 1380 |
| tctccgggta aa | 1392 |

<210> SEQ ID NO 102
<211> LENGTH: 1335
<212> TYPE: DNA
<213> ORGANISM: Artificial Sequence
<220> FEATURE:
<223> OTHER INFORMATION: cDNA codon optimized mAb 6785 heavy chain without leader sequence

<400> SEQUENCE: 102

| | |
|---|---|
| caagtgcagc tgctggagag cggcggcggc ctggtgcagc ccggcggcag cctgcggctg | 60 |
| agctgcgccg ccagcggctt caccttcagc agctacgcca tgagctgggt gcggcaggcc | 120 |
| cccggcaagg gcctggagtg ggtgagcacc atcagcctga ccagcggctt cacctactac | 180 |
| gccgacagcg tgaagggccg gttcaccatc agccgggaca acagcaagaa caccctgtac | 240 |
| ctgcagatga acagcctgcg ggccgaggac accgccgtgt actactgcgc ccggcagctg | 300 |
| accctggacg tgtggggcca gggcaccctg gtgaccgtga gcagcgcctc caccaagggc | 360 |
| ccatcggtct tccccctggc accctcctcc aagagcacct ctgggggcac agcggccctg | 420 |
| ggctgcctgg tcaaggacta cttccccgaa ccggtgacgg tgtcgtggaa ctcaggcgcc | 480 |
| ctgaccagcg gcgtgcacac cttcccggct gtcctacagt cctcaggact ctactccctc | 540 |
| agcagcgtgg tgaccgtgcc ctccagcagc ttgggcaccc agacctacat ctgcaacgtg | 600 |
| aatcacaagc ccagcaacac caaggtggac aagaaagttg agcccaaatc ttgtgacaaa | 660 |
| actcacacat gcccaccgtg cccagcacct gaactcctgg ggggaccgtc agtcttcctc | 720 |
| ttccccccaa aacccaagga caccctcatg atctcccgga cccctgaggt cacatgcgtg | 780 |
| gtggtggacg tgagccacga agaccctgag gtcaagttca actggtacgt ggacggcgtg | 840 |
| gaggtgcata atgccaagac aaagccgcgg gaggagcagt acaacagcac gtaccgtgtg | 900 |
| gtcagcgtcc tcaccgtcct gcaccaggac tggctgaatg gcaaggagta caagtgcaag | 960 |
| gtctccaaca agccctccc agccccatc gagaaaacca tctccaaagc caagggcag | 1020 |
| ccccgagaac acaggtgta caccctgccc ccatcccggg atgagctgac caagaaccag | 1080 |
| gtcagcctga cctgcctggt caaaggcttc tatcccagcg acatcgccgt ggagtgggag | 1140 |
| agcaatgggc agccggagaa caactacaag accacgcctc ccgtgctgga ctccgacggc | 1200 |
| tccttcttcc tctacagcaa gctcaccgtg gacaagagca ggtggcagca ggggaacgtc | 1260 |
| ttctcatgct ccgtgatgca tgaggctctg cacaaccact acacgcagaa gagcctctcc | 1320 |
| ctgtctccgg gtaaa | 1335 |

<210> SEQ ID NO 103
<211> LENGTH: 699
<212> TYPE: DNA
<213> ORGANISM: Artificial Sequence
<220> FEATURE:
<223> OTHER INFORMATION: cDNA codon optimized mAb 6785 light chain with leader sequence

<400> SEQUENCE: 103

| | |
|---|---|
| atggcctggt ctcctctcct cctcactctc ctcgctcact gcacagggtc ctgggcccag | 60 |

```
agcgtgctga cccagccccc cagcgtgagc gtggcccccg gccagaccgc ccggatcagc    120
tgcagcggcg acaacctggg cgacaagtac gccaactggt accagcagaa gcccggccag    180
gcccccgtgc tggtgatcta cgacgacatc gaccggccca gcggcatccc cgagcggttc    240
agcggcagca acagcggcaa caccgccacc ctgaccatca gcggcaccca ggccgaggac    300
gaggccgact actactgcgg cagctacgac ttcttcctgg gcatgatcgt gttcggcggc    360
ggcaccaagc tgaccgtgct gggtcagccc aaggctgcac ccagtgtcac tctgttccCg    420
ccctcctctg aggagcttca agccaacaag gccacactgg tgtgtctcat aagtgacttc    480
tacccgggag ccgtgacagt ggcctggaag gccgatagca gccccgtcaa ggcgggagtg    540
gagaccacca cccctccaa acaaagcaac aacaagtacg cggccagcag ctatctgagc    600
ctgacgcctg agcagtggaa gtcccacaga agctacagct gccaggtcac gcatgaaggg    660
agcaccgtgg agaagacagt ggcccctaca gaatgttca                          699

<210> SEQ ID NO 104
<211> LENGTH: 642
<212> TYPE: DNA
<213> ORGANISM: Artificial Sequence
<220> FEATURE:
<223> OTHER INFORMATION: cDNA codon optimized mAb 6785 light chain
      without leader sequence

<400> SEQUENCE: 104
cagagcgtgc tgacccagcc ccccagcgtg agcgtggccc ccggccagac cgcccggatc     60
agctgcagcg gcgacaacct gggcgacaag tacgccaact ggtaccagca gaagcccggc    120
caggcccccg tgctggtgat ctacgacgac atcgaccggc cagcggcat ccccgagcgg    180 ttcagcggca gcaacagcgg caacaccgcc accctgacca tcagcggcac ccaggccgag    240
gacgaggccg actactactg cggcagctac gacttcttcc tgggcatgat cgtgttcggc    300
ggcggcacca agctgaccgt gctgggtcag cccaaggctg cacccagtgt cactctgttc    360 ccgcccctcct ctgaggagct tcaagccaac aaggccacac tggtgtgtct cataagtgac    420
ttctacccgg gagccgtgac agtggcctgg aaggccgata gcagccccgt caaggcggga    480
gtggagacca ccacccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca                      642

<210> SEQ ID NO 105
<211> LENGTH: 132
<212> TYPE: PRT
<213> ORGANISM: Homo sapiens

<400> SEQUENCE: 105

Gly Ile Thr Ile Pro Arg Asn Pro Gly Cys Pro Asn Ser Glu Asp Lys
 1               5                  10                  15

Asn Phe Pro Arg Thr Val Met Val Asn Leu Asn Ile His Asn Arg Asn
            20                  25                  30

Thr Asn Thr Asn Pro Lys Arg Ser Ser Asp Tyr Tyr Asn Arg Ser Thr
        35                  40                  45

Ser Pro Trp Asn Leu His Arg Asn Glu Asp Pro Glu Arg Tyr Pro Ser
    50                  55                  60

Val Ile Trp Glu Ala Lys Cys Arg His Leu Gly Cys Ile Asn Ala Asp
65                  70                  75                  80

Gly Asn Val Asp Tyr His Met Asn Ser Val Pro Ile Gln Gln Glu Ile
```

```
                85                  90                  95
Leu Val Leu Arg Arg Glu Pro Pro His Cys Pro Asn Ser Phe Arg Leu
            100                 105                 110

Glu Lys Ile Leu Val Ser Val Gly Cys Thr Cys Val Thr Pro Ile Val
            115                 120                 125

His His Val Ala
            130

<210> SEQ ID NO 106
<211> LENGTH: 132
<212> TYPE: PRT
<213> ORGANISM: Artificial Sequence
<220> FEATURE:
<223> OTHER INFORMATION: Mature IL-17Amut6

<400> SEQUENCE: 106

Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
            20                  25                  30

Thr Asn Thr Asn Pro Lys Arg Ser Ser Asp Tyr Tyr Asn Arg Ser Thr
        35                  40                  45

Ser Pro Trp Asn Leu His Arg Asn Glu Asp Pro Glu Arg Tyr Pro Ser
    50                  55                  60

Val Ile Trp Glu Ala Gln Cys Arg His Leu Gly Cys Ile Asn Ala Asp
65                  70                  75                  80

Gly Asn Val Asp Tyr His Met Asn Ser Val Pro Ile Gln Gln Glu Ile
                85                  90                  95

Leu Val Leu Arg Arg Glu Pro Pro His Cys Pro Asn Ser Phe Arg Leu
            100                 105                 110

Glu Lys Ile Leu Val Ser Val Gly Cys Thr Cys Val Thr Pro Ile Val
            115                 120                 125

His His Val Gln
            130

<210> SEQ ID NO 107
<211> LENGTH: 866
<212> TYPE: PRT
<213> ORGANISM: Homo sapiens

<400> SEQUENCE: 107

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
            115                 120                 125
```

-continued

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                    165                 170                 175

Ser Lys Asn Phe Leu Val Pro Asp Cys Glu His Ala Arg Met Lys Val
                180                 185                 190

Thr Thr Pro Cys Met Ser Ser Gly Ser Leu Trp Asp Pro Asn Ile Thr
                195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                    245                 250                 255

Pro Glu Glu Phe His Gln Arg Ser Asn Val Thr Leu Thr Leu Arg Asn
                260                 265                 270

Leu Lys Gly Cys Cys Arg His Gln Val Gln Ile Gln Pro Phe Phe Ser
                275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Val Tyr Trp Phe Ile Thr Gly Ile Ser Ile Leu Leu Val Gly Ser Val
                    325                 330                 335

Ile Leu Leu Ile Val Cys Met Thr Trp Arg Leu Ala Gly Pro Gly Ser
                340                 345                 350

Glu Lys Tyr Ser Asp Asp Thr Lys Tyr Thr Asp Gly Leu Pro Ala Ala
                355                 360                 365

Asp Leu Ile Pro Pro Pro Leu Lys Pro Arg Lys Val Trp Ile Ile Tyr
    370                 375                 380

Ser Ala Asp His Pro Leu Tyr Val Asp Val Val Leu Lys Phe Ala Gln
385                 390                 395                 400

Phe Leu Leu Thr Ala Cys Gly Thr Glu Val Ala Leu Asp Leu Leu Glu
                    405                 410                 415

Glu Gln Ala Ile Ser Glu Ala Gly Val Met Thr Trp Val Gly Arg Gln
                420                 425                 430

Lys Gln Glu Met Val Glu Ser Asn Ser Lys Ile Ile Val Leu Cys Ser
                435                 440                 445

Arg Gly Thr Arg Ala Lys Trp Gln Ala Leu Leu Gly Arg Gly Ala Pro
    450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
                    485                 490                 495

Gly Thr Tyr Val Val Cys Tyr Phe Ser Glu Val Ser Cys Asp Gly Asp
                500                 505                 510

Val Pro Asp Leu Phe Gly Ala Ala Pro Arg Tyr Pro Leu Met Asp Arg
                515                 520                 525

Phe Glu Glu Val Tyr Phe Arg Ile Gln Asp Leu Glu Met Phe Gln Pro
    530                 535                 540

Gly Arg Met His Arg Val Gly Glu Leu Ser Gly Asp Asn Tyr Leu Arg
545                 550                 555                 560

```
Ser Pro Gly Gly Arg Gln Leu Arg Ala Ala Leu Asp Arg Phe Arg Asp
            565                 570                 575

Trp Gln Val Arg Cys Pro Asp Trp Phe Glu Cys Glu Asn Leu Tyr Ser
            580                 585                 590

Ala Asp Asp Gln Asp Ala Pro Ser Leu Asp Glu Glu Val Phe Glu Glu
            595                 600                 605

Pro Leu Leu Pro Pro Gly Thr Gly Ile Val Lys Arg Ala Pro Leu Val
            610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
            645                 650                 655

Arg Gly Gln Pro Ala Pro Gln Pro Leu His Thr Leu Val Leu Ala Ala
            660                 665                 670

Glu Glu Gly Ala Leu Val Ala Ala Val Glu Pro Gly Pro Leu Ala Asp
            675                 680                 685

Gly Ala Ala Val Arg Leu Ala Leu Ala Gly Glu Gly Glu Ala Cys Pro
            690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
            725                 730                 735

Pro Asp Leu Leu Pro Glu Asp Val Arg Glu His Leu Glu Gly Leu Met
            740                 745                 750

Leu Ser Leu Phe Glu Gln Ser Leu Ser Cys Gln Ala Gln Gly Gly Cys
            755                 760                 765

Ser Arg Pro Ala Met Val Leu Thr Asp Pro His Thr Pro Tyr Glu Glu
            770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu Glu
            805                 810                 815

Glu Glu Gln Asp Pro Gly Lys Pro Ala Leu Pro Leu Ser Pro Glu Asp
            820                 825                 830

Leu Glu Ser Leu Arg Ser Leu Gln Arg Gln Leu Leu Phe Arg Gln Leu
            835                 840                 845

Gln Lys Asn Ser Gly Trp Asp Thr Met Gly Ser Glu Ser Glu Gly Pro
850                 855                 860

Ser Ala
865

<210> SEQ ID NO 108
<211> LENGTH: 155
<212> TYPE: PRT
<213> ORGANISM: Cynocephalus monkey

<400> SEQUENCE: 108

Met Thr Pro Gly Lys Thr Ser Leu Val Ser Leu Leu Leu Leu Leu Ser
  1               5                  10                  15

Leu Glu Ala Ile Val Lys Ala Gly Ile Ala Ile Pro Arg Asn Ser Gly
                 20                  25                  30

Cys Pro Asn Ser Glu Asp Lys Asn Phe Pro Arg Thr Val Met Val Asn
             35                  40                  45

Leu Asn Ile His Asn Arg Asn Thr Ser Thr Asn Pro Lys Arg Ser Ser
         50                  55                  60
```

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
            85                  90                  95

Leu Gly Cys Val Lys Ala Asp Gly Asn Val Asp Tyr His Met Asn Ser
            100                 105                 110

Val Pro Ile Gln Gln Glu Ile Leu Val Leu Arg Arg Glu Pro Arg His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 109
<211> LENGTH: 19
<212> TYPE: PRT
<213> ORGANISM: Artificial Sequence
<220> FEATURE:
<223> OTHER INFORMATION: N-terminal leader for expression of heavy
      chains

<400> SEQUENCE: 109

Met Ala Trp Val Trp Thr Leu Leu Phe Leu Met Ala Ala Ala Gln Ser
1               5                   10                  15

Ile Gln Ala

<210> SEQ ID NO 110
<211> LENGTH: 20
<212> TYPE: PRT
<213> ORGANISM: Artificial Sequence
<220> FEATURE:
<223> OTHER INFORMATION: N-terminal leader for expression of light
      chains

<400> SEQUENCE: 110

Met Gly Val Pro Thr Gln Val Leu Gly Leu Leu Leu Leu Trp Leu Thr
1               5                   10                  15

Asp Ala Arg Cys
            20

<210> SEQ ID NO 111
<211> LENGTH: 224
<212> TYPE: PRT
<213> ORGANISM: Artificial Sequence
<220> FEATURE:
<223> OTHER INFORMATION: Fab6468 heavy chain with His tag

<400> SEQUENCE: 111

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Leu Thr Ser Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

```
Ala Arg Gln Leu Thr Leu Asp Val Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys His His His His His His
            210                 215                 220
```

<210> SEQ ID NO 112
<211> LENGTH: 399
<212> TYPE: DNA
<213> ORGANISM: Artificial Sequence
<220> FEATURE:
<223> OTHER INFORMATION: Mature IL-17Amut6 cDNA sequence (2 aa mutations vs. WT IL-17A)

<400> SEQUENCE: 112

```
ggcataacca tacccggaa ccccggctgt cccaacagcg aagataaaaa ttttccacgt      60
accgttatgg tgaatctcaa tattcacaat cgaaacacta acactaaccc taagcggagc    120
agcgactatt ataatcggag cactagcccc tggaacctgc atcggaacga agatcccgaa    180
cggtaccccca gcgtaatttg gaagcccaa tgtcggcatc tgggttgtat taatgccgac    240
ggcaatgtcg attatcatat gaatagcgtg cctattcaac aggaaattct agtgctacgg    300
cgggaacccc cccattgtcc taatagcttt cgcctcgaaa aaatcctcgt cagcgtcggg    360
tgtacgtgcg tgacgcccat cgtgcatcac gtccaatga                          399
```

<210> SEQ ID NO 113
<211> LENGTH: 791
<212> TYPE: PRT
<213> ORGANISM: Homo sapiens

<400> SEQUENCE: 113

```
Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Val Ser Leu Glu Pro Trp Gly Asp Glu Arg Leu Arg
            35                  40                  45

Val Gln Phe Leu Ala Gln Gln Ser Leu Ser Leu Ala Pro Val Thr Ala
        50                  55                  60

Ala Thr Ala Arg Thr Ala Leu Ser Gly Leu Ser Gly Ala Asp Gly Arg
65                  70                  75                  80

Arg Glu Glu Arg Gly Arg Gly Lys Ser Trp Val Cys Leu Ser Leu Gly
                85                  90                  95

Gly Ser Gly Asn Thr Glu Pro Gln Lys Lys Gly Leu Ser Cys Arg Leu
            100                 105                 110

Trp Asp Ser Asp Ile Leu Cys Leu Pro Gly Asp Ile Val Pro Ala Pro
            115                 120                 125
```

```
Gly Pro Val Leu Ala Pro Thr His Leu Gln Thr Glu Leu Val Leu Arg
    130                 135                 140

Cys Gln Lys Glu Thr Asp Cys Asp Leu Cys Leu Arg Val Ala Val His
145                 150                 155                 160

Leu Ala Val His Gly His Trp Glu Glu Pro Glu Asp Glu Glu Lys Phe
                165                 170                 175

Gly Gly Ala Ala Asp Ser Gly Val Glu Glu Pro Arg Asn Ala Ser Leu
            180                 185                 190

Gln Ala Gln Val Val Leu Ser Phe Gln Ala Tyr Pro Thr Ala Arg Cys
        195                 200                 205

Val Leu Leu Glu Val Gln Val Pro Ala Ala Leu Val Gln Phe Gly Gln
    210                 215                 220

Ser Val Gly Ser Val Val Tyr Asp Cys Phe Glu Ala Ala Leu Gly Ser
225                 230                 235                 240

Glu Val Arg Ile Trp Ser Tyr Thr Gln Pro Arg Tyr Glu Lys Glu Leu
                245                 250                 255

Asn His Thr Gln Gln Leu Pro Asp Cys Arg Gly Leu Glu Val Trp Asn
            260                 265                 270

Ser Ile Pro Ser Cys Trp Ala Leu Pro Trp Leu Asn Val Ser Ala Asp
        275                 280                 285

Gly Asp Asn Val His Leu Val Leu Asn Val Ser Glu Glu Gln His Phe
    290                 295                 300

Gly Leu Ser Leu Tyr Trp Asn Gln Val Gln Gly Pro Pro Lys Pro Arg
305                 310                 315                 320

Trp His Lys Asn Leu Thr Gly Pro Gln Ile Ile Thr Leu Asn His Thr
                325                 330                 335

Asp Leu Val Pro Cys Leu Cys Ile Gln Val Trp Pro Leu Glu Pro Asp
            340                 345                 350

Ser Val Arg Thr Asn Ile Cys Pro Phe Arg Glu Asp Pro Arg Ala His
        355                 360                 365

Gln Asn Leu Trp Gln Ala Ala Arg Leu Arg Leu Leu Thr Leu Gln Ser
    370                 375                 380

Trp Leu Leu Asp Ala Pro Cys Ser Leu Pro Ala Glu Ala Ala Leu Cys
385                 390                 395                 400

Trp Arg Ala Pro Gly Gly Asp Pro Cys Gln Pro Leu Val Pro Pro Leu
                405                 410                 415

Ser Trp Glu Asn Val Thr Val Asp Lys Val Leu Glu Phe Pro Leu Leu
            420                 425                 430

Lys Gly His Pro Asn Leu Cys Val Gln Val Asn Ser Ser Glu Lys Leu
        435                 440                 445

Gln Leu Gln Glu Cys Leu Trp Ala Asp Ser Leu Gly Pro Leu Lys Asp
    450                 455                 460

Asp Val Leu Leu Leu Glu Thr Arg Gly Pro Gln Asp Asn Arg Ser Leu
465                 470                 475                 480

Cys Ala Leu Glu Pro Ser Gly Cys Thr Ser Leu Pro Ser Lys Ala Ser
                485                 490                 495

Thr Arg Ala Ala Arg Leu Gly Glu Tyr Leu Leu Gln Asp Leu Gln Ser
            500                 505                 510

Gly Gln Cys Leu Gln Leu Trp Asp Asp Leu Gly Ala Leu Trp Ala
        515                 520                 525

Cys Pro Met Asp Lys Tyr Ile His Lys Arg Trp Ala Leu Val Trp Leu
530                 535                 540

Ala Cys Leu Leu Phe Ala Ala Ala Leu Ser Leu Ile Leu Leu Leu Lys
```

```
                545                 550                 555                 560
Lys Asp His Ala Lys Gly Trp Leu Arg Leu Leu Lys Gln Asp Val Arg
                    565                 570                 575

Ser Gly Ala Ala Ala Arg Gly Arg Ala Ala Leu Leu Leu Tyr Ser Ala
                580                 585                 590

Asp Asp Ser Gly Phe Glu Arg Leu Val Gly Ala Leu Ala Ser Ala Leu
                595                 600                 605

Cys Gln Leu Pro Leu Arg Val Ala Val Asp Leu Trp Ser Arg Arg Glu
            610                 615                 620

Leu Ser Ala Gln Gly Pro Val Ala Trp Phe His Ala Gln Arg Arg Gln
625                 630                 635                 640

Thr Leu Gln Glu Gly Gly Val Val Leu Leu Phe Ser Pro Gly Ala
                    645                 650                 655

Val Ala Leu Cys Ser Glu Trp Leu Gln Asp Gly Val Ser Gly Pro Gly
                660                 665                 670

Ala His Gly Pro His Asp Ala Phe Arg Ala Ser Leu Ser Cys Val Leu
                675                 680                 685

Pro Asp Phe Leu Gln Gly Arg Ala Pro Gly Ser Tyr Val Gly Ala Cys
            690                 695                 700

Phe Asp Arg Leu Leu His Pro Asp Ala Val Pro Ala Leu Phe Arg Thr
705                 710                 715                 720

Val Pro Val Phe Thr Leu Pro Ser Gln Leu Pro Asp Phe Leu Gly Ala
                    725                 730                 735

Leu Gln Gln Pro Arg Ala Pro Arg Ser Gly Arg Leu Glu Arg Ala
                740                 745                 750

Glu Gln Val Ser Arg Ala Leu Gln Pro Ala Leu Asp Ser Tyr Phe His
                755                 760                 765

Pro Pro Gly Thr Pro Ala Pro Gly Arg Gly Val Gly Pro Gly Ala Gly
            770                 775                 780

Pro Gly Ala Gly Asp Gly Thr
785                 790

<210> SEQ ID NO 114
<211> LENGTH: 330
<212> TYPE: PRT
<213> ORGANISM: Homo sapiens

<400> SEQUENCE: 114

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
              130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 115
<211> LENGTH: 327
<212> TYPE: PRT
<213> ORGANISM: Homo sapiens

<400> SEQUENCE: 115

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
```

```
                    180                 185                 190
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 116
<211> LENGTH: 19
<212> TYPE: PRT
<213> ORGANISM: Artificial Sequence
<220> FEATURE:
<223> OTHER INFORMATION: Leader sequence for light chain expression

<400> SEQUENCE: 116

Met Ala Trp Ser Pro Leu Leu Leu Thr Leu Leu Ala His Cys Thr Gly
1               5                   10                  15

Ser Trp Ala

<210> SEQ ID NO 117
<211> LENGTH: 98
<212> TYPE: PRT
<213> ORGANISM: Homo sapiens

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 118
<211> LENGTH: 99
<212> TYPE: PRT
<213> ORGANISM: Homo sapiens

<400> SEQUENCE: 118
```

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 119
<211> LENGTH: 98
<212> TYPE: PRT
<213> ORGANISM: Homo sapiens

<400> SEQUENCE: 119

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 120
<211> LENGTH: 98
<212> TYPE: PRT
<213> ORGANISM: Homo sapiens

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Ala Arg Lys Ala Pro Gly Lys Gly Leu Glu Trp Val
        35                  40                  45

Ser Gly Val Ser Trp Asn Gly Ser Arg Thr His Tyr Val Asp Ser Val
    50                  55                  60

Lys Arg Arg Phe Ile Ile Ser Arg Asp Asn Ser Arg Asn Ser Leu Tyr
65                  70                  75                  80

Leu Gln Lys Asn Arg Arg Arg Ala Glu Asp Met Ala Val Tyr Tyr Cys
                85                  90                  95

Val Arg

<210> SEQ ID NO 121
<211> LENGTH: 98
<212> TYPE: PRT
```

-continued

<213> ORGANISM: Homo sapiens

<400> SEQUENCE: 121

Thr Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Val Arg Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Ile Ile Ser Arg Asp Asn Ser Arg Asn Phe Leu Tyr
65                  70                  75                  80

Gln Gln Met Asn Ser Leu Arg Pro Glu Asp Met Ala Val Tyr Tyr Cys
                85                  90                  95

Val Arg

<210> SEQ ID NO 122
<211> LENGTH: 98
<212> TYPE: PRT
<213> ORGANISM: Homo sapiens

<400> SEQUENCE: 122

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg

<210> SEQ ID NO 123
<211> LENGTH: 98
<212> TYPE: PRT
<213> ORGANISM: Homo sapiens

<400> SEQUENCE: 123

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

```
<210> SEQ ID NO 124
<211> LENGTH: 98
<212> TYPE: PRT
<213> ORGANISM: Homo sapiens

<400> SEQUENCE: 124

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 125
<211> LENGTH: 98
<212> TYPE: PRT
<213> ORGANISM: Homo sapiens

<400> SEQUENCE: 125

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 126
<211> LENGTH: 98
<212> TYPE: PRT
<213> ORGANISM: Homo sapiens

<400> SEQUENCE: 126

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
<210> SEQ ID NO 127
<211> LENGTH: 98
<212> TYPE: PRT
<213> ORGANISM: Homo sapiens

<400> SEQUENCE: 127

Gln Val Gln Leu Val Glu Ser Gly Gly Gly Val Val Gln Pro Gly Arg
  1               5                  10                  15
Ser Leu Arg Leu Ser Cys Ala Ala Ser Gly Phe Thr Phe Ser Ser Tyr
             20                  25                  30
Gly Met His Trp Val Arg Gln Ala Pro Gly Lys Gly Leu Glu Trp Val
         35                  40                  45
Ala Val Ile Trp Tyr Asp Gly Ser Asn Lys Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg

<210> SEQ ID NO 128
<211> LENGTH: 98
<212> TYPE: PRT
<213> ORGANISM: Homo sapiens

<400> SEQUENCE: 128

Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Asn Ser
             20                  25                  30
Asp Met Asn Trp Val His Gln Ala Pro Gly Lys Gly Leu Glu Trp Val
         35                  40                  45
Ser Gly Val Ser Trp Asn Gly Ser Arg Thr His Tyr Ala Asp Ser Val
     50                  55                  60
Lys Gly Arg Phe Ile Ile Ser Arg Asp Asn Ser Arg Asn Thr Leu Tyr
 65                  70                  75                  80
Leu Gln Thr Asn Ser Leu Arg Ala Glu Asp Thr Ala Val Tyr Tyr Cys
                 85                  90                  95
Val Arg

<210> SEQ ID NO 129
<211> LENGTH: 99
<212> TYPE: PRT
<213> ORGANISM: Homo sapiens

<400> SEQUENCE: 129

Glu Val Gln Leu Val Glu Ser Gly Gly Gly Val Val Gln Pro Gly Gly
  1               5                  10                  15
Ser Leu Arg Leu Ser Cys Ala Ala Ser Gly Phe Thr Phe Asp Asp Tyr
             20                  25                  30
Thr Met His Trp Val Arg Gln Ala Pro Gly Lys Gly Leu Glu Trp Val
         35                  40                  45
Ser Leu Ile Ser Trp Asp Gly Gly Ser Thr Tyr Tyr Ala Asp Ser Val
     50                  55                  60
```

```
Lys Gly Arg Phe Thr Ile Ser Arg Asp Asn Ser Lys Asn Ser Leu Tyr
 65                  70                  75                  80

Leu Gln Met Asn Ser Leu Arg Thr Glu Asp Thr Ala Leu Tyr Tyr Cys
                 85                  90                  95

Ala Lys Asp

<210> SEQ ID NO 130
<211> LENGTH: 98
<212> TYPE: PRT
<213> ORGANISM: Homo sapiens

<400> SEQUENCE: 130

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Tyr Ile Ser Ser Ser Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 131
<211> LENGTH: 98
<212> TYPE: PRT
<213> ORGANISM: Homo sapiens

<400> SEQUENCE: 131

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Tyr Val
         35                  40                  45

Ser Ala Ile Ser Ser Asn Gly Gly Ser Thr Tyr Tyr Ala Asn Ser Val
     50                  55                  60

Lys Gly Arg Phe Thr Ile Ser Arg Asp Asn Ser Lys Asn Thr Leu Tyr
 65                  70                  75                  80

Leu Gln Met Gly Ser Leu Arg Ala Glu Asp Met Ala Val Tyr Tyr Cys
                 85                  90                  95

Ala Arg

<210> SEQ ID NO 132
<211> LENGTH: 98
<212> TYPE: PRT
<213> ORGANISM: Homo sapiens

<400> SEQUENCE: 132

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Trp Met His Trp Val Arg Gln Ala Pro Gly Lys Gly Leu Val Trp Val
         35                  40                  45
```

```
Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 133
<211> LENGTH: 17
<212> TYPE: PRT
<213> ORGANISM: Homo sapiens

<400> SEQUENCE: 133

Ala Glu Tyr Phe Gln His Trp Gly Gln Gly Thr Leu Val Thr Val Ser
  1               5                  10                  15

Ser

<210> SEQ ID NO 134
<211> LENGTH: 17
<212> TYPE: PRT
<213> ORGANISM: Homo sapiens

<400> SEQUENCE: 134

Tyr Trp Tyr Phe Asp Leu Trp Gly Arg Gly Thr Leu Val Thr Val Ser
  1               5                  10                  15

Ser

<210> SEQ ID NO 135
<211> LENGTH: 15
<212> TYPE: PRT
<213> ORGANISM: Homo sapiens

<400> SEQUENCE: 135

Ala Phe Asp Val Trp Gly Gln Gly Thr Met Val Thr Val Ser Ser
  1               5                  10                  15

<210> SEQ ID NO 136
<211> LENGTH: 15
<212> TYPE: PRT
<213> ORGANISM: Homo sapiens

<400> SEQUENCE: 136

Tyr Phe Asp Tyr Trp Gly Gln Gly Thr Leu Val Thr Val Ser Ser
  1               5                  10                  15

<210> SEQ ID NO 137
<211> LENGTH: 16
<212> TYPE: PRT
<213> ORGANISM: Homo sapiens

<400> SEQUENCE: 137

Asn Trp Phe Asp Ser Trp Gly Gln Gly Thr Leu Val Thr Val Ser Ser
  1               5                  10                  15

<210> SEQ ID NO 138
<211> LENGTH: 20
<212> TYPE: PRT
<213> ORGANISM: Homo sapiens

<400> SEQUENCE: 138

Tyr Tyr Tyr Tyr Tyr Gly Met Asp Val Trp Gly Gln Gly Thr Thr Val
```

```
            1               5                   10                  15
Thr Val Ser Ser
            20
```

<210> SEQ ID NO 139
<211> LENGTH: 95
<212> TYPE: PRT
<213> ORGANISM: Homo sapiens

<400> SEQUENCE: 139

```
Ser Tyr Glu Leu Thr Gln Pro Pro Ser Val Ser Val Ser Pro Gly Gln
 1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala
                85                  90                  95
```

<210> SEQ ID NO 140
<211> LENGTH: 95
<212> TYPE: PRT
<213> ORGANISM: Homo sapiens

<400> SEQUENCE: 140

```
Ser Tyr Glu Leu Thr Gln Pro Leu Ser Val Ser Val Ala Leu Gly Gln
 1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala
                85                  90                  95
```

<210> SEQ ID NO 141
<211> LENGTH: 96
<212> TYPE: PRT
<213> ORGANISM: Homo sapiens

<400> SEQUENCE: 141

```
Ser Tyr Glu Leu Thr Gln Pro Pro Ser Val Ser Val Ser Pro Gly Gln
 1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80
```

```
Asp Glu Ala Asp Tyr Tyr Cys Tyr Ser Thr Asp Ser Ser Gly Asn His
                85                  90                  95
```

<210> SEQ ID NO 142
<211> LENGTH: 96
<212> TYPE: PRT
<213> ORGANISM: Homo sapiens

<400> SEQUENCE: 142

```
Ser Tyr Glu Leu Thr Gln Pro His Ser Val Ser Val Ala Thr Ala Gln
 1               5                  10                  15

Met Ala Arg Ile Thr Cys Gly Gly Asn Asn Ile Gly Ser Lys Ala Val
                20                  25                  30

His Trp Tyr Gln Gln Lys Pro Gly Gln Asp Pro Val Leu Val Ile Tyr
                35                  40                  45

Ser Asp Ser Asn Arg Pro Ser Gly Ile Pro Glu Arg Phe Ser Gly Ser
            50                  55                  60

Asn Pro Gly Asn Thr Thr Thr Leu Thr Ile Ser Arg Ile Glu Ala Gly
 65                  70                  75                  80

Asp Glu Ala Asp Tyr Tyr Cys Gln Val Trp Asp Ser Ser Ser Asp His
                85                  90                  95
```

<210> SEQ ID NO 143
<211> LENGTH: 96
<212> TYPE: PRT
<213> ORGANISM: Homo sapiens

<400> SEQUENCE: 143

```
Ser Tyr Glu Leu Thr Gln Pro Pro Ser Val Ser Val Ser Leu Gly Gln
 1               5                  10                  15

Met Ala Arg Ile Thr Cys Ser Gly Glu Ala Leu Pro Lys Lys Tyr Ala
                20                  25                  30

Tyr Trp Tyr Gln Gln Lys Pro Gly Gln Phe Pro Val Leu Val Ile Tyr
                35                  40                  45

Lys Asp Ser Glu Arg Pro Ser Gly Ile Pro Glu Arg Phe Ser Gly Ser
            50                  55                  60

Ser Ser Gly Thr Ile Val Thr Leu Thr Ile Ser Gly Val Gln Ala Glu
 65                  70                  75                  80

Asp Glu Ala Asp Tyr Tyr Cys Leu Ser Ala Asp Ser Ser Gly Thr Tyr
                85                  90                  95
```

<210> SEQ ID NO 144
<211> LENGTH: 96
<212> TYPE: PRT
<213> ORGANISM: Homo sapiens

<400> SEQUENCE: 144

```
Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
                35                  40                  45

Gly Lys Asn Asn Arg Pro Ser Gly Ile Pro Asp Arg Phe Ser Gly Ser
            50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                85                  90                  95
```

```
<210> SEQ ID NO 145
<211> LENGTH: 96
<212> TYPE: PRT
<213> ORGANISM: Homo sapiens

<400> SEQUENCE: 145

Ser Tyr Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Ile Tyr
         35                  40                  45

Tyr Asp Ser Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

<210> SEQ ID NO 146
<211> LENGTH: 94
<212> TYPE: PRT
<213> ORGANISM: Homo sapiens

<400> SEQUENCE: 146

Ser Tyr Glu Leu Thr Gln Leu Pro Ser Val Ser Val Ser Pro Gly Gln
 1               5                  10                  15

Thr Ala Arg Ile Thr Cys Ser Gly Asp Val Leu Gly Glu Asn Tyr Ala
             20                  25                  30

Asp Trp Tyr Gln Gln Lys Pro Gly Gln Ala Pro Glu Leu Val Ile Tyr
         35                  40                  45

Glu Asp Ser Glu Arg Tyr Pro Gly Ile Pro Glu Arg Phe Ser Gly Ser
     50                  55                  60

Thr Ser Gly Asn Thr Thr Thr Leu Thr Ile Ser Arg Val Leu Thr Glu
 65                  70                  75                  80

Asp Glu Ala Asp Tyr Tyr Cys Leu Ser Gly Asp Glu Asp Asn
                 85                  90

<210> SEQ ID NO 147
<211> LENGTH: 96
<212> TYPE: PRT
<213> ORGANISM: Homo sapiens

<400> SEQUENCE: 147

Ser Tyr Glu Leu Met Gln Pro Pro Ser Val Ser Val Ser Pro Gly Gln
 1               5                  10                  15

Thr Ala Arg Ile Thr Cys Ser Gly Asp Ala Leu Pro Lys Gln Tyr Ala
             20                  25                  30

Tyr Trp Tyr Gln Gln Lys Pro Gly Gln Ala Pro Val Leu Val Ile Tyr
         35                  40                  45

Lys Asp Ser Glu Arg Pro Ser Gly Ile Pro Glu Arg Phe Ser Gly Ser
     50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                 85                  90                  95
```

<210> SEQ ID NO 148
<211> LENGTH: 94
<212> TYPE: PRT
<213> ORGANISM: Homo sapiens

<400> SEQUENCE: 148

Ser Tyr Glu Leu Thr Gln Pro Ser Ser Val Ser Val Ser Pro Gly Gln
1               5                   10                  15

Thr Ala Arg Ile Thr Cys Ser Gly Asp Val Leu Ala Lys Lys Tyr Ala
            20                  25                  30

Arg Trp Phe Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Asp Tyr Tyr Cys Tyr Ser Ala Ala Asp Asn Asn
                85                  90

<210> SEQ ID NO 149
<211> LENGTH: 94
<212> TYPE: PRT
<213> ORGANISM: Homo sapiens

<400> SEQUENCE: 149

Ser Ser Gly Pro Thr Gln Val Pro Ala Val Ser Val Ala Leu Gly Gln
1               5                   10                  15

Met Ala Arg Ile Thr Cys Gln Gly Asp Ser Met Glu Gly Ser Tyr Glu
            20                  25                  30

His Trp Tyr Gln Gln Lys Pro Gly Gln Ala Pro Val Leu Val Ile Tyr
        35                  40                  45

Asp Ser Ser Asp Arg Pro Ser Arg Ile Pro Glu Arg Phe Ser Gly Ser
    50                  55                  60

Lys Ser Gly Asn Thr Thr Thr Leu Thr Ile Thr Gly Ala Gln Ala Glu
65                  70                  75                  80

Asp Glu Ala Asp Tyr Tyr Tyr Gln Leu Ile Asp Asn His Ala
                85                  90

<210> SEQ ID NO 150
<211> LENGTH: 12
<212> TYPE: PRT
<213> ORGANISM: Homo sapiens

<400> SEQUENCE: 150

Tyr Val Phe Gly Thr Gly Thr Lys Val Thr Val Leu
1               5                   10

<210> SEQ ID NO 151
<211> LENGTH: 12
<212> TYPE: PRT
<213> ORGANISM: Homo sapiens

<400> SEQUENCE: 151

Val Val Phe Gly Gly Gly Thr Lys Leu Thr Val Leu
1               5                   10

<210> SEQ ID NO 152
<211> LENGTH: 12
<212> TYPE: PRT
<213> ORGANISM: Homo sapiens

<400> SEQUENCE: 152

```
Val Val Phe Gly Gly Gly Thr Lys Leu Thr Val Leu
1               5                   10

<210> SEQ ID NO 153
<211> LENGTH: 12
<212> TYPE: PRT
<213> ORGANISM: Homo sapiens

<400> SEQUENCE: 153

Phe Val Phe Gly Gly Gly Thr Gln Leu Ile Ile Leu
1               5                   10

<210> SEQ ID NO 154
<211> LENGTH: 12
<212> TYPE: PRT
<213> ORGANISM: Homo sapiens

<400> SEQUENCE: 154

Trp Val Phe Gly Glu Gly Thr Glu Leu Thr Val Leu
1               5                   10

<210> SEQ ID NO 155
<211> LENGTH: 12
<212> TYPE: PRT
<213> ORGANISM: Homo sapiens

<400> SEQUENCE: 155

Asn Val Phe Gly Ser Gly Thr Lys Val Thr Val Leu
1               5                   10

<210> SEQ ID NO 156
<211> LENGTH: 12
<212> TYPE: PRT
<213> ORGANISM: Homo sapiens

<400> SEQUENCE: 156

Ala Val Phe Gly Gly Gly Thr Gln Leu Thr Val Leu
1               5                   10

<210> SEQ ID NO 157
<211> LENGTH: 13
<212> TYPE: PRT
<213> ORGANISM: Homo sapiens
<220> FEATURE:
<223> OTHER INFORMATION: Residues 56-68 of mature human IL-17A

<400> SEQUENCE: 157

Asn Glu Asp Pro Glu Arg Tyr Pro Ser Val Ile Trp Glu
1               5                   10

<210> SEQ ID NO 158
<211> LENGTH: 17
<212> TYPE: PRT
<213> ORGANISM: Artificial Sequence
<220> FEATURE:
<223> OTHER INFORMATION: Residues 100-116 of mature human IL-17A

<400> SEQUENCE: 158

Arg Arg Glu Pro Pro His Cys Pro Asn Ser Phe Arg Leu Glu Lys Ile
1               5                   10                  15

Leu

<210> SEQ ID NO 159
<211> LENGTH: 10
<212> TYPE: PRT
```

```
<213> ORGANISM: Artificial Sequence
<220> FEATURE:
<223> OTHER INFORMATION: Residues 45-54 of mature human IL-17A

<400> SEQUENCE: 159

Asn Arg Ser Thr Ser Pro Trp Asn Leu His
 1               5                  10

<210> SEQ ID NO 160
<211> LENGTH: 17
<212> TYPE: PRT
<213> ORGANISM: Artificial Sequence
<220> FEATURE:
<223> OTHER INFORMATION: Residues 71-87 of mature human IL-17A

<400> SEQUENCE: 160

Cys Arg His Leu Gly Cys Ile Asn Ala Asp Gly Asn Val Asp Tyr His
 1               5                  10                  15

Met
```